(12) United States Patent
Illig et al.

(10) Patent No.: US 8,759,347 B2
(45) Date of Patent: Jun. 24, 2014

(54) INHIBITORS OF C-FMS KINASE

(71) Applicant: Janssen Pharmaceutica NV, Beerse (BE)

(72) Inventors: Carl R. Illig, Phoenixville, PA (US); Shelly K. Ballentine, Lansdale, PA (US); Jinsheng Chen, Exton, PA (US); Renee Louise DesJarlais, Saint Davids, PA (US); Sanath K. Meegalla, Garnet Valley, PA (US); Mark Wall, Lansdale, PA (US); Kenneth J. Wilson, Guanacaste (CR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/917,251

(22) Filed: Jun. 13, 2013

(65) Prior Publication Data

US 2013/0281475 A1   Oct. 24, 2013

Related U.S. Application Data

(62) Division of application No. 13/080,861, filed on Apr. 6, 2011, now Pat. No. 8,481,564, which is a division of application No. 12/139,876, filed on Jun. 16, 2008, now Pat. No. 7,973,035, which is a division of application No. 11/736,617, filed on Apr. 18, 2007, now Pat. No. 7,414,050.

(60) Provisional application No. 60/883,539, filed on Jan. 5, 2007, provisional application No. 60/793,697, filed on Apr. 20, 2006.

(51) Int. Cl.
*A61K 31/506* (2006.01)
*C07D 403/12* (2006.01)
*C07D 405/12* (2006.01)

(52) U.S. Cl.
USPC ............. 514/252.03; 514/252.05; 544/331; 544/297; 544/298; 544/322

(58) Field of Classification Search
USPC .......... 544/331, 297, 298, 322; 514/252.03, 514/252.05
See application file for complete search history.

(56) References Cited

U.S. PATENT DOCUMENTS

| | | |
|---|---|---|
| 2,466,420 A | 4/1949 | Hagemeyer et al. |
| 3,226,394 A | 12/1965 | Schipper |
| 4,551,540 A | 11/1985 | Hechenbleikner et al. |
| 5,190,541 A | 3/1993 | Abele et al. |
| 5,474,765 A | 12/1995 | Thorpe |
| 5,762,918 A | 6/1998 | Thorpe |
| 5,855,866 A | 1/1999 | Thorpe et al. |
| 5,874,442 A | 2/1999 | Doll et al. |
| 5,944,718 A | 8/1999 | Austin et al. |
| 5,968,952 A | 10/1999 | Venet et al. |
| 6,037,350 A | 3/2000 | Venet et al. |
| 6,100,254 A | 8/2000 | Budde et al. |
| 6,117,432 A | 9/2000 | Ganne et al. |
| 6,169,096 B1 | 1/2001 | Venet et al. |
| 6,187,786 B1 | 2/2001 | Venet et al. |
| 6,235,746 B1 | 5/2001 | Davis et al. |
| 6,342,219 B1 | 1/2002 | Thorpe et al. |
| 6,346,625 B1 | 2/2002 | Karabelas et al. |
| 6,383,790 B1 | 5/2002 | Shokat |
| 6,420,387 B1 | 7/2002 | Venet et al. |
| 6,458,800 B1 | 10/2002 | Angibaud et al. |
| 6,596,746 B1 | 7/2003 | Das et al. |
| 6,692,491 B1 | 2/2004 | Phan |
| 7,157,456 B2 | 1/2007 | Straub et al. |
| 7,208,493 B2 | 4/2007 | Wrasidlo et al. |
| 7,414,050 B2 | 8/2008 | Illig et al. |
| 7,427,683 B2 | 9/2008 | Player et al. |
| 7,429,603 B2 | 9/2008 | Player et al. |
| 7,645,755 B2 | 1/2010 | Illig et al. |
| 7,662,837 B2 | 2/2010 | Illig et al. |

(Continued)

FOREIGN PATENT DOCUMENTS

| | | |
|---|---|---|
| EP | 1566379 A1 | 8/2005 |
| GB | 1189719 | 4/1970 |

(Continued)

OTHER PUBLICATIONS

Abarbri et al., J. Org. Chem. (2000), 65, 4618-4634.

(Continued)

*Primary Examiner* — Kahsay Habte

(57) ABSTRACT

The invention is directed to compounds of Formula I:

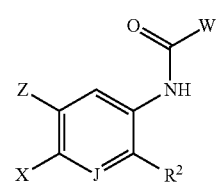

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, prostate cancer, lung cancer, colon cancer, stomach cancer, hairy cell leukemia; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone with the compounds of Formula I, are also provided.

18 Claims, No Drawings

(56) References Cited

U.S. PATENT DOCUMENTS

| | | | |
|---|---|---|---|
| 7,790,724 B2 | 9/2010 | Player et al. |
| 7,795,279 B2 | 9/2010 | Ballentine et al. |
| 7,973,035 B2 | 7/2011 | Illig et al. |
| 2002/0016625 A1 | 2/2002 | Falotico et al. |
| 2002/0019414 A1 | 2/2002 | Altmann et al. |
| 2003/0153610 A1 | 8/2003 | Straub et al. |
| 2004/0049032 A1 | 3/2004 | Charrier et al. |
| 2005/0113566 A1 | 5/2005 | Player et al. |
| 2005/0131022 A1 | 6/2005 | Player et al. |
| 2006/0040995 A1 | 2/2006 | Bacque et al. |
| 2006/0100619 A1 | 5/2006 | McClurken et al. |
| 2006/0122181 A1 | 6/2006 | Ikemoto et al. |
| 2006/0148812 A1 | 7/2006 | Illig et al. |
| 2006/0189623 A1 | 8/2006 | Illig et al. |
| 2006/0258666 A1 | 11/2006 | Player et al. |
| 2006/0258724 A1 | 11/2006 | Straub et al. |
| 2006/0281788 A1 | 12/2006 | Baumann et al. |
| 2007/0249608 A1 | 10/2007 | Illig et al. |
| 2007/0249649 A1 | 10/2007 | Illig et al. |
| 2007/0249680 A1 | 10/2007 | Illig et al. |
| 2007/0249685 A1 | 10/2007 | Illig et al. |
| 2008/0051402 A1 | 2/2008 | Illig et al. |
| 2009/0105296 A1 | 4/2009 | Chen et al. |
| 2009/0197913 A1 | 8/2009 | Baumann et al. |

FOREIGN PATENT DOCUMENTS

| | | |
|---|---|---|
| WO | WO 94/10138 | 5/1994 |
| WO | WO 96/11932 | 4/1996 |
| WO | WO 96/21452 | 7/1996 |
| WO | WO 96/32907 | 10/1996 |
| WO | WO 97/16443 | 5/1997 |
| WO | WO 97/21701 | 6/1997 |
| WO | WO 97/30992 | 8/1997 |
| WO | WO 98/06700 | 2/1998 |
| WO | WO 98/28264 | 7/1998 |
| WO | WO 98/28303 | 7/1998 |
| WO | WO 98/40383 | 9/1998 |
| WO | WO 98/49157 | 11/1998 |
| WO | WO 98/54174 | 12/1998 |
| WO | WO 99/45712 | 9/1999 |
| WO | WO 99/45912 | 9/1999 |
| WO | WO 00/01691 | 1/2000 |
| WO | WO 00/02871 | 1/2000 |
| WO | WO 00/12498 | 3/2000 |
| WO | WO 00/12499 | 3/2000 |
| WO | WO 00/27820 | 5/2000 |
| WO | WO 00/39082 | 7/2000 |
| WO | WO 01/47897 | 7/2001 |
| WO | WO 01/47919 | 7/2001 |
| WO | WO 01/49667 | 7/2001 |
| WO | WO 02/32861 | 4/2002 |
| WO | WO 02/068406 | 9/2002 |
| WO | WO 02/092599 | 11/2002 |
| WO | WO 03/024931 | 3/2003 |
| WO | WO 03/024969 | 3/2003 |
| WO | WO 03/035009 | 5/2003 |
| WO | WO 03/037347 | 5/2003 |
| WO | WO 03/057690 | 7/2003 |
| WO | WO 03/099771 | 12/2003 |
| WO | WO 03/099796 | 12/2003 |
| WO | WO 2004/005281 | 1/2004 |
| WO | WO 2004/016597 | 2/2004 |
| WO | WO 2004/018419 | 3/2004 |
| WO | WO 2004/022525 | 3/2004 |
| WO | WO 2004/039782 | 5/2004 |
| WO | WO 2004/043389 | 5/2004 |
| WO | WO 2004/046120 | 6/2004 |
| WO | WO 2004/058749 | 7/2004 |
| WO | WO 2004/085388 | 10/2004 |
| WO | WO 2004/096795 | 11/2004 |
| WO | WO 2005/012220 | 2/2005 |
| WO | WO 2005/040139 | 5/2005 |
| WO | WO 2005/047273 | 5/2005 |
| WO | WO 2005/073225 | 8/2005 |
| WO | WO 2006/047277 | 5/2006 |
| WO | WO 2006/047504 | 5/2006 |
| WO | WO 2006/135630 | 12/2006 |
| WO | WO 2006/135636 | 12/2006 |
| WO | WO 2006/135713 | 12/2006 |
| WO | WO 2006/135718 | 12/2006 |
| WO | WO 2006/138155 | 12/2006 |
| WO | WO 2007/048088 | 4/2007 |
| WO | WO 2009/058968 | 5/2009 |

OTHER PUBLICATIONS

Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107 ,2006.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Barkenbus et al., Journal of Organic Chemistry (1951), 16, 232-8.
Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1977, 66(1): 1-19.
Bodansky, M. et al., "The Practice of Peptide Synthesis", Springer-Verlag, NY (1984).
British Journal of Haematology, "Flt3 mutations and leukaemia", 2003,122(4):523-38.
Brown et al., J. Chem. Soc., Perkin Trans. 2, 1039-1051 (2002).
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Byrn et al., Solid-State Chemistry of Drugs, Second Edition, 1999, pp. 233-247.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Coll. Czech. Chem. Commun.: 31(11), 4432-41, (1966), Palecek, J.
Comprehensive Organic Transformations: Larock, R.S.; Wiley and Sons Inc., USA 1999.
Cortes. Farnesyltransferase inhibitors in acute myeloid leukemia and myelodysplastic syndromes. Clinical Lymphoma, vol. 4, Suppl. 1, S30-S35, 2003.
Crandall et al., J. Am. Chem. Soc. (1968), 90, 6251-6253.
Cummins et al., Tetrahedron (1988), 44(16), 5151.
Drexler, H. G. et al. (2004), "FLT3: receptor and ligand"; Growth Factors 22(2):71-3.
Drexler, H.G., "The Leukemia-Lymphoma Cell Line Factsbook", Academic Pres:SanDiego, CA, 2000.

(56) References Cited

OTHER PUBLICATIONS

Eastwood, P., Tetrahedron Lett. (2000), 41, 3705-8.
Ferrara et al., "Prognostic factors and therapeutic options for relapsed or refractory acute myeloid leukemia." Haematologica. Aug. 2004, vol. 89, No. 8, Aug. 2004; pp. 998-1008 (ISR ref).
Gavezzotti, "Are Crystal Structures Predictable?" Accounts of Chemical Research, vol. 27, pp. 309-314 (1994).
Gilliand, G., et.al, "The roles of FLT3 in mematopoiesis and leukemia", Blood. 2002; 100:1532-42.
Gotlib, J (2005) "Farnesyltransferase inhibitor therapy in acute myelogenous leukemia." Curr. Hematol. Rep.;4(1):77-84.
Gould, P., "Salt selection for basic drugs", Ref. International J. Pharm. 1986, 33, 201-217.
Gray, M. et al., Tetrahedron Lett., 41:6237-40 (2000).
Griswold, I. J. et al., "Effects of MLN518, A Dual FLT3 and KIT inhibitor, on Normal and Malignant Hematopoiesis" Blood, Jul. 2004 [Epub ahead of print].
Guillory (in Brittain ed.) Polymorphism, etc., NY: Marcel Dekker, Inc., 1999, 1-2, 183-226.
Haluska P., G.K. Dy, A.A. Adjei. (2002) "Farnesyl transferase inhibitors as anticancer agents." Eur J Cancer. 38(13):1685-700.
Han, J., Advances in Characterization of Pharmaceutical Hydrates, Trends in Bio/PharmaceuticalIndustry, pp. 25-29. Mar. 2006.
Harmata et al., Org. Lett. (2000), 2, 2703-2705.
Hartwig, J.F., "Organopalladium Chemistry for Organic Synthesis," Wiley Interscience, NY (2002).
Hellstrom et al., "Antibodies for Drug Delivery", in Controlled Drug Delivery (2nd Ed.), Robinson et al. (eds.), pp. 623-653 (Marcel Dekker, Inc. 1987).
Hengartner, MO. (2000) "The biochemistry of apoptosis." Nature 407:770-76.
Hess et al., J. Am. Chem. Soc. (1998), 120, 12310.
Hill et al., J. Am. Chem. Soc. (1973), 95, 1338.
Hogermeier et al., Chem. Eur. J., 2007, 13, 2410.
Iddon. B. et al., J. Chem. Soc. Perkin Trans. 1., 1370, (1980).
Ishikubo et al (Jpn J Clin Oncol 36:494-498, 2006).
Johnson et al., Brit J Cancer, 84:1424-1431 (2001).
Lyon et al., J. Med. Chem., 29: 630-634 (1986).
Romeo et al., J. Med. Chem., 46: 2877 (2003).
Johnson et al., J. Org. Chem. (1970), 35(3), 584-592.
Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).
Katritsky, A. et al., "para-Formylation of Nitroarenes via Vicarious Nucleophilic Substitution of Hydrogen with Tris(benzotriazol-1-yl)methane", Tetrahedron Lett., 37:347-50 (1996).
Kim et al., European Journal of Organic Chemistry (2000), 12, 2195-2201.
Kolder, C.R., et al, "Synthesis and Reactivity of 5-Chloro-2,4-Dihydrosypyridine", x Recl. Trav. Chim. Pays-Bas; 285 (1953).
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Larock, R.C., Comprehensive Organic Transformations, $2^{nd}$ Ed., Wiley-VCH, NY, (1999), pp. 996-1003.
Lee, K. and Cha, J. K., J. Amer. Chem. Soc., 123: 5590-5591 (2001).
Levis, M. et al. 2001, "A FLT3 tyrosine kinase inhibitor is selectively cytotoxic to acute myeloid leukemia blasts harboring FLT3 internal tandem duplication mutations", Blood 98(3):885-7.
Levis, M. et al., "Novel FLT3 tyrosine kinase inhibitors" Expert Opin. Investing. Drugs (2003) 12 (12) 1951-1962.
Levis, M. et al., "Small Molecule FLT3 Tyrosine Kinase Inhibitors" Current Pharmaceutical Design, 2004, 10, 1183-1193.
Levis, M., et al. (2004) "In vitro studies of a FLT3 inhibitor combined with chemotherapy: sequence of administration is important to achieve synergistic cytotoxic effects." Blood. 104(4):1145-50.
Lewis, et al. "Diacetoxypiperidinium Analogs of Acetylcholine", Junal of Medicinal Chemistry, 1973, vol. 16, No. 2 pp. 156-159.
Lipshutz et al., Tetrahedron Lett. (1988), 29, 3411-3414.
Loader, C., et al., "Pyrrole chemistry. XXIII. The cyanation of substituted pyrroles with chlorosulfonyl isocyanate (CSI). New syntheses of pyrrole-3-carbonitriles.", Can. J. Chem, 59, 2673 (1981).
Lovborg H, Gullbo J, Larsson R. (2005) "Screening for apoptosis-classical and emerging techniques." Anticancer Drugs 16:593-9.
Lyon, R. , et al., "Synthesis and Evaluation of Phenyl-and Benzoylpiperazines as Potential Serotonergic Agents", J. Med. Chem., 29: 630-4 (1986).
Major, R., et al. "1-Alkoxy-4-phenyl-4-propionoxypiperdines and Their 3-Methyl Homologs as New Analgesics", vol. 26, pp. 1867-1847, (1961).
McBee et al., Journal of the American Chemical Society (1957), 79, 2323-5.
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Meltzer et al., Bioorganic & Medicinal Chemistry (2002), 10(11) and 3583-3591.
Miyaura, N. et al., "Palladium-Catalyzed Cross-Coupling Reactions of Organoboron Compounds", Chem. Rev. 95:2457 (1995).
Modern Amination Methods: Ricci, A., Ed., Wiley-VCH: Weinheim, 2000.
Muci, et al., "Practical Palladium Catalysts for C-N and C-O Bond Formation", Top. Curr., Chem. 219-131-209 (2001.
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Nicolai, E., et al., "New Process for the Synthesis of Imidazo[4-5-b] pyridine Derivatives as Potent Orally Active Thromboxane $A_2$ Receptor Antagonists", J. Heterocyclic Chemistry, 31, (73) (1994).
Noyori et al., Org. React., 1983, 29, 163.
Nunez G, Benedict MA, Hu Y, Inohara N. (1998) "Caspases: the proteases of the apoptotic pathway." Oncogene 17:3237-45.
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Prendergast et al., (2001) "Farnesyl Transferase Inhibtors: Mechanism and Applications" Expert Opin Investig Drugs. 10(12):2105-16).
Protecting Groups, P, Kocienski Thieme Medical Publishers, 2000.
Pure Appl. Chem., 1976, 45:13-30.
Quentmeier H, et al. FLT3 mutations in acute myeloid leukemia cell lines. Leukemia. Jan. 2003;17:120-124.
Regan, J., et al., Structure-Activity Relationships of the p38* MAP Kinsase Inhibitor 1-)5-tert-Butyl-2-p-tolyl-2h-pyrazol-3-yl)-3-[4-(2-morpholin-4-yl-ethoxy)naph-thalen-1-yl-)urea (BIRB 796)J. Med. Chem., 46:4676-86 (2003).
Reinecke et al., Chemistry—A European Journal (1995), 1(6), 368-73.
Romeo, G., et al, "New Pyrimido [5,4-b_indoles as Ligands for *1-Adrenoceptor Subtypes", J. Med. Chem., 46: 2877-2894 (2003).
Sadick, M. et al., Analysis of Heregulin-Induced ErbB2 Phosphorylation with a High-Throughput Kinase Receptor Activation Enzyme-Linked Immunsorbent Assay, Analytical Biochemistry. 1996; 235:207-214.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Scheijen, B. et al. (2002), "Tyrosine kinase oncogenes innormal hematopoiesis and hematological disease", Oncogene 21(21):3314-33.
Schmid et al., Helv. Chim. Acta. (1974), 57, 1883 [see English summary provided].
Sendelbach, et al, Journal of Organic Chemistry (1999), 64(10), 3398-3408.

(56) References Cited

OTHER PUBLICATIONS

Shih L. Y. et al., (2004) "Internal tandem duplication of fms-like tyrosine kinase 3 is associated with poor outcome in patients with myelodysplastic syndrome." Cancer, 101; 989-98.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).
Stille, J.K., "The Palladium-Catalyzed Cross-Coupling Reactions of Organotin Reagents with Organic Electrophiles", Angew, Chem, Int. Ed. Engl., 25:508-524 (1986).
Stirewalt, D.L. et al. (2003), "The role of FLT3 in haematopoietic malignancies", NatRev Cancer 3(9):650-65.
Stone, R.M. et al. "PKC 412 FLT3 inhibitor therapy in AML: results of a phase II trial" An Hematol 2004; 83 Suppl 1:S89-90.
Sundermeier, U., Doebler, C. and Beller, M., Modern Oxidation Methods, Baeckvall, J. (Ed.)., 1-20, Wiley-Verlag (2004) Weinheim, Germany (2004).
Suzuki, A., "Metal-Catalyzed Coupling Reactions" F. Deiderich, P. Stang, Eds., Wiley-VCH, Weinheim (1998).
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
Takahashi, K., et al, Chem. Lett. (2000), 126-7.
Takaya et al., J Amer Chem Soc, (1978), 100(6), 1765-77.
Thalhammer et al. Duration of second complete remission in patients with acute myeloid leukemia treated with chemotherapy: a retrospective single-center study. Ann. Hematology, 1996, 72: 216-222.
Thompson et al., Journal of Industrial and Engineering Chemistry (Washington, D.C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tse, K.F. et al., "Inhibition of FLT3-mediated transformation by use of a tyrosine kinase inhibitor" Leukemia, Jul. 15, 2001(7):1001-10.
van Engeland M., L.J. Nieland ,et al. (1998) "Annexin V-affinity assay: a review on an apoptosis detection system based on phosphatidylserine exposure." Cytometry. 31(1):1-9.
Vippagunta et al, "Crystalline Solids" Advanced Drug Delivery Reviews, vol. 48, pp. 3-26 (2001).
Walker et al (Dermatol 212:70-72, 2006; (Abstract Only).
West et al., J. Org. Chem (1993), 58, 6795-6803.
Wroblewski et al., Journal of the American Chemical Society (1996), 118, 10168-10174.
Wustrow, et al, "Coupling of Arylboronic Acids with a Partially Reduced Pyridine Derivative" Synthesis, 993 (1991).
www.cancer.org (accessed online Mar. 2, 2010), "Can Acute Myeloid Luchemia (AML) Be Prevented?".

Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al., Blood, vol. 105, No. 12, 4759-4766, Published online Feb. 22, 2005.
Beletskaya et al., *Chem. Rev.*, 100:3009 (2000).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
Corey et al., *Tetrahedron Lett.*, 29, 995 (1988).
Couturier et al., *Organic Process Research & Development*, 2002, 6, 42-48.
Dirlam et al., *J. Heterocyclic Chem*, 17, 409, (1980).
Dolan, S., et al, *J. Chem., Soc., Chem. Commun.*, 1588-9 (1985).
Fohlisch et al, *Liebigs Annalen der Chemie*, (1), 1-5 (1987) [English Abstract provided].
Galemmo et al., *J. Med. Chem.*, 33(10), 2828-41; (1990).
Guanti et al., *Tetrahedron*, 46 (20), 7081, (1990).
Guanti et al., *Tetrahedron: Asymmetry* 8(13), 2175-2187, (1997).
Hayakawa et al., *Bioorg. Med. Chem. Lett.*, 14(2): 455-8 (2004).
Hulkenberg et al., *Tetrahedron Lett.*, 23(14), 1505-08; (1982).
Itsuno et al., *Synthesis*, 12, 995-6, (1988).
Khanapure et al, *J. Med. Chem.*, 48(11): 3930-34 (2005).
Koutek, et al, *Synth. Commun.*, 6 (4), 305-8 (1976).
Leonard et al., *J. Org. Chem.*, 28, 3021, (1963).
Liu et al., *J. Am. Chem. Soc.* 2004, 126, 5182.
Martinez_Teipel et al., *QSAR & Combinatorial Science*, 23(10), 854-858 (2004).
Mock et al., *J. Phys. Org. Chem.*, 16(3), 175-182 (2003).
Myles et al., *J. Org. Chem.*, 55, 1636 (1990).
Nguyen et al., *Tetrahedron*, 62(4), 647-651; (2006).
Nose et al., *Chem. Pharm. Bull.*, 38(8), 2097-101, (1990).
Quintard et al., *J. Org. Chem.*, 48: 1559-60 (1983).
Reed et al., *Synthetic Communications*, 20(4), 563-71, (1990).
Roush, W., *J. Am. Chem. Soc.* 102, 1390 (1980).
Tohma et al., *Adv. Syn. Catalysis*, 346, 111-124 (2004).
Wustrow et al., Tetrahedron Lett., 35, 61-4 (1994).
Suzuki, A. In *Metal-Catalyzed Cross Coupling Reactions*; Diederich, F., Stang, P. J., Eds.; Wiley-VCH: Weinheim, Germany, 1998; Chapter 2, pp. 49-89.
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Jonas, Nilsson W. et al., "Solid-Phase Synthesis of Libraries Generated from a 4-Phenyl-2-carboxy-piperazine Scaffold", J. Comb. Chem., 2001, 3, 546-553.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.

INHIBITORS OF C-FMS KINASE

CROSS REFERENCE TO RELATED APPLICATION

This application is a divisional of U.S. patent application Ser. No. 13/080,861, filed Apr. 6, 2011, pending; which is a divisional of U.S. patent application Ser. No. 12/139,876, filed Jun. 16, 2008, now U.S. Pat. No. 7,973,035; which is a divisional of U.S. patent application Ser. No. 11/736,617, filed Apr. 18, 2007, now U.S. Pat. No. 7,414,050; which claims priority from U.S. Provisional Application Ser. Nos. 60/793,697, filed Apr. 20,2006 and 60/883,539, filed Jan. 5, 2007, the contents of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 23, 2013, is named PRD2659USDIV3_SL.txt and is 825 bytes in size.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R overexpression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

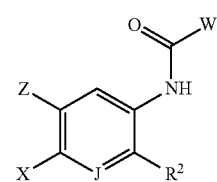

or a solvate, hydrate, tautomer or pharmaceutically acceptable salt thereof, wherein:

W is

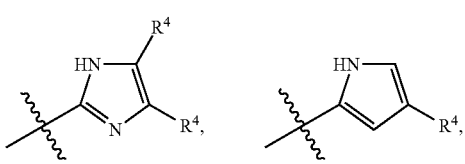

-continued

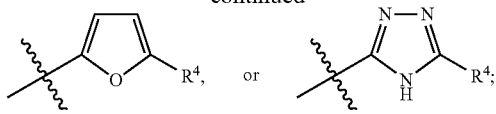

wherein R⁴=H, F, Cl, Br, I, OH, OCH₃, OCH₂CH₃, —C$_{(1-3)}$alkyl, —CO₂R⁵, CONR⁶R⁷, C=—CR⁸, or CN;
  wherein R⁵=H, or —C$_{(1-3)}$alkyl;
  R⁶=H, or —C$_{(1-3)}$alkyl;
  R⁷=H, or —C$_{(1-3)}$alkyl; and
  R⁸=H, —CH₂OH, or —CH₂CH₂OH;
R² is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro[5.5]undec-2-enyl)heterocyclyl (including piperidinyl), spirosubstituted piperidinyl (including 3-aza-spiro[5.5]undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy C$_{(1-3)}$alkyl, and C$_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);
X is selected from the group consisting of:

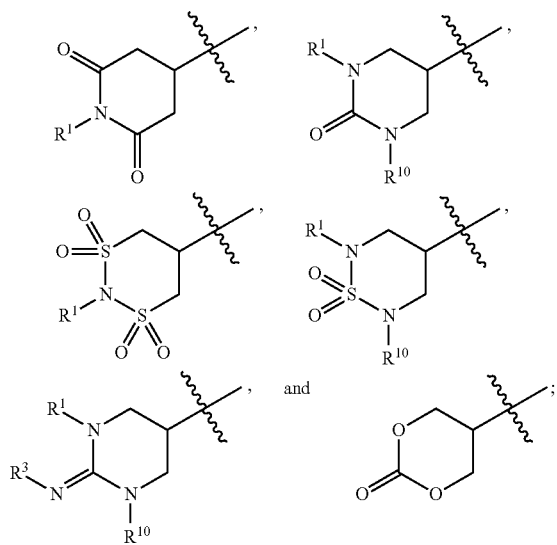

wherein R¹ and R¹⁰ are independently is H, —CH₃, or —C₂ to C₅ alkyl optionally substituted with 1 or 2 of: Me, Et, OH, NH₂, NHMe, NMe₂, NHEt, NEt₂, pyrrolidinyl, pyridyl, morpholino, CONH₂, or COOH and such that when any two heteroatoms are attached to said C₂ to C₅ alkyl group there exists at least two carbon atoms between them, and
R³ is —SO₂Me, SO₂Et, —CO₂R⁹, —NO₂, or —CN;
  wherein R⁹=H, or C$_{(1-3)}$alkyl;
Z is H, F, Cl, Br, C₁-C₃ alkyl or —CH₂OH; and
J is CH or N.

Herein and throughout this application, the terms "Me", "Et", "Pr", and "Bu" refer to methyl, ethyl, propyl, and butyl respectively.

DETAILED DESCRIPTION OF THE INVENTION

The invention is directed to the novel compounds of Formula I:

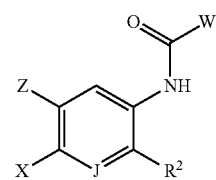

or a solvate, hydrate, tautomer or pharmaceutically acceptable salt thereof, wherein:
W is

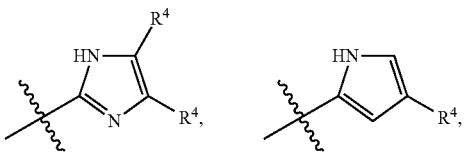

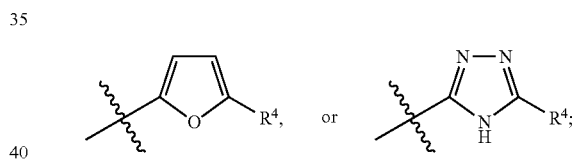

wherein R⁴=H, F, Cl, Br, I, OH, OCH₃, OCH₂CH₃, —C$_{(1-3)}$alkyl, —CO₂R⁵, CONR⁶R⁷, C=—CR⁸, or CN;
  wherein R⁵=H, or —C$_{(1-3)}$alkyl;
  R⁶=H, or —C$_{(1-3)}$alkyl;
  R⁷=H, or —C$_{(1-3)}$alkyl; and
  R⁸=H, —CH₂OH, or —CH₂CH₂OH;
R² is cycloalkyl (including cyclohexenyl, and cycloheptenyl), spiro-substituted cycloalkenyl (including spiro[2.5]oct-5-ene, spiro[3.5]non-6-ene, spiro[4.5]dec-7-ene, and spiro[5.5]undec-2-ene)heterocyclyl (including piperidinyl), spirosubstituted piperidinyl (including 3-aza-spiro[5.5]undecane, and 8-aza-spiro[4.5]decane), thiophenyl, dihydrosulfonopyranyl, phenyl, furanyl, tetrahydropyridyl, or dihydropyranyl, any of which may be independently substituted with one or two of each of the following: chloro, fluoro, hydroxy C$_{(1-3)}$alkyl, and C$_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);

X is selected from the group consisting of:

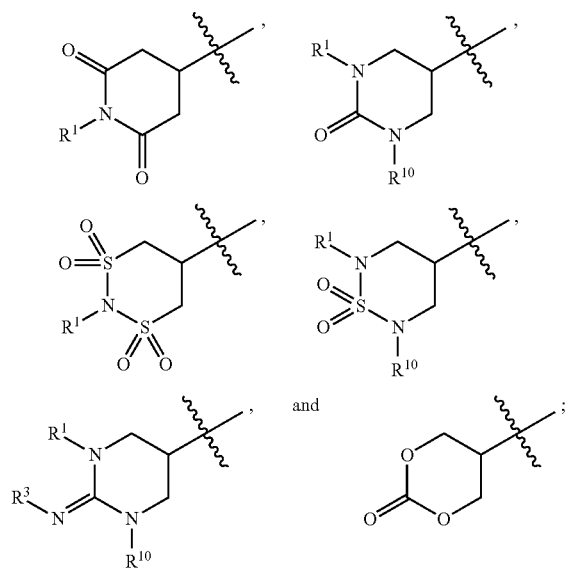

wherein $R^1$ and $R^{10}$ are independently H, —CH$_3$, or —C$_2$ to C$_5$ alkyl optionally substituted with one or two of: Me, Et, OH, NH$_2$, NHMe, NMe$_2$, NHEt, NEt$_2$, pyrrolidinyl, pyridyl, morpholino, CONH$_2$, or COOH and such that when any two heteroatoms are attached to said C$_2$ to C$_5$ alkyl group there exists at least two carbon atoms between them, and $R^3$ is —SO$_2$Me, SO$_2$Et, —CO$_2$R$^9$, —NO$_2$, or —CN;
  wherein $R^9$=H, or C$_{(1-3)}$alkyl;
Z is H, F, Cl, Br, C$_1$-C$_3$ alkyl or —CH$_2$OH; and
J is CH or N.

In a preferred embodiment of the invention:
W is

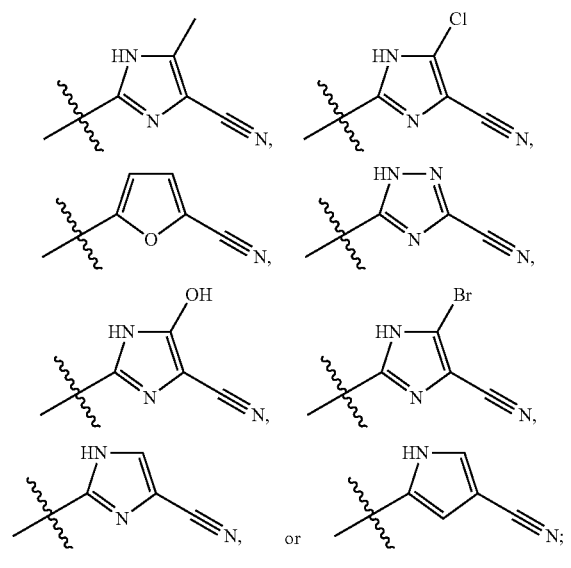

$R^2$ is

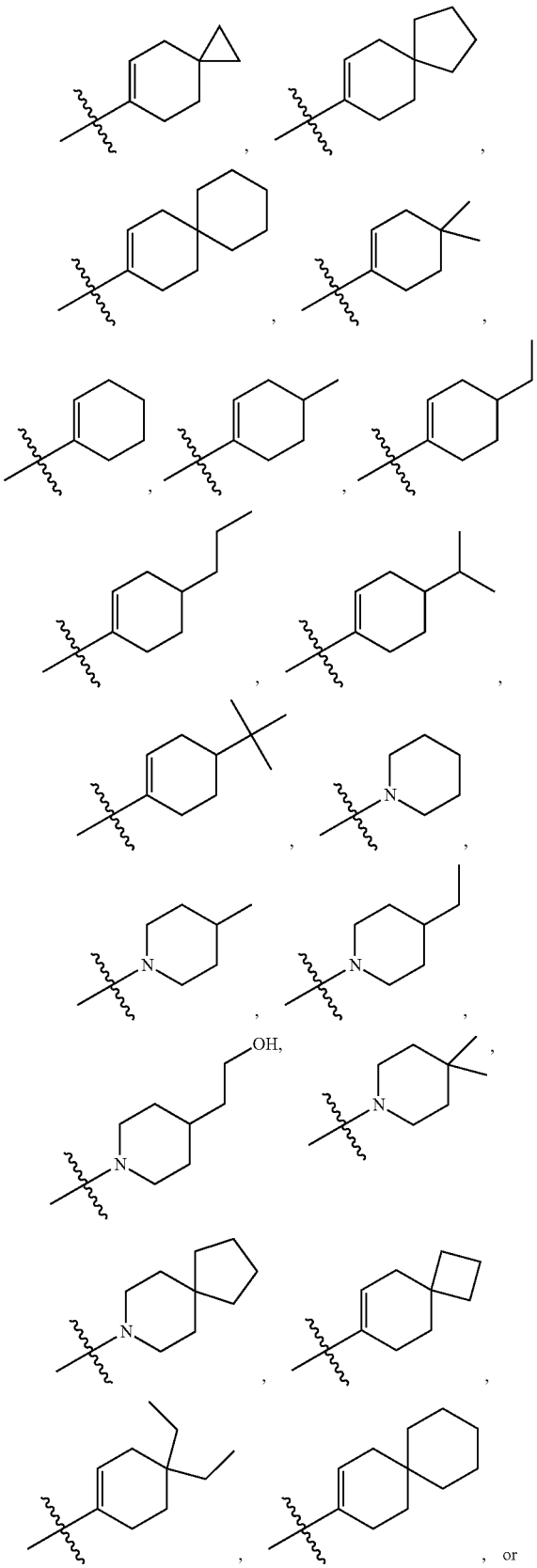

X is selected from the group consisting of:

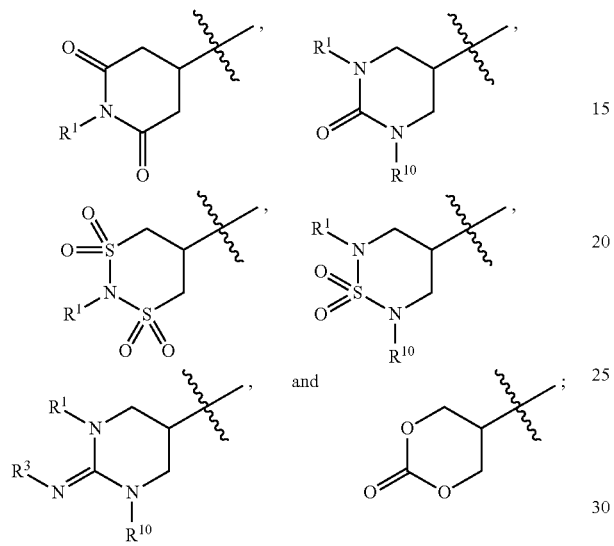

wherein $R^1$ and $R^{10}$ are independently H, —$CH_3$, or —$C_2$ to $C_5$ alkyl optionally substituted with 1 or 2 of: Me, Et, OH, $NH_2$, NHMe, $NMe_2$, NHEt, $NEt_2$, pyrrolidinyl, pyridyl, morpholino, $CONH_2$, or COOH and such that when any two heteroatoms are attached to said $C_2$ to $C_5$ alkyl group there exists at least two carbon atoms between them, and $R^3$ is —$SO_2Me$, $SO_2Et$, —$CO_2R^9$, —$NO_2$, or —CN; wherein $R^9$=H, or $C_{(1-3)}$alkyl;

Z is H, F, Cl, Br, $C_1$-$C_3$ alkyl or —$CH_2OH$; and

J is CH or N;

as well as solvates, hydrates, tautomers and pharmaceutically acceptable salts thereof.

In another embodiment of the invention:

W is

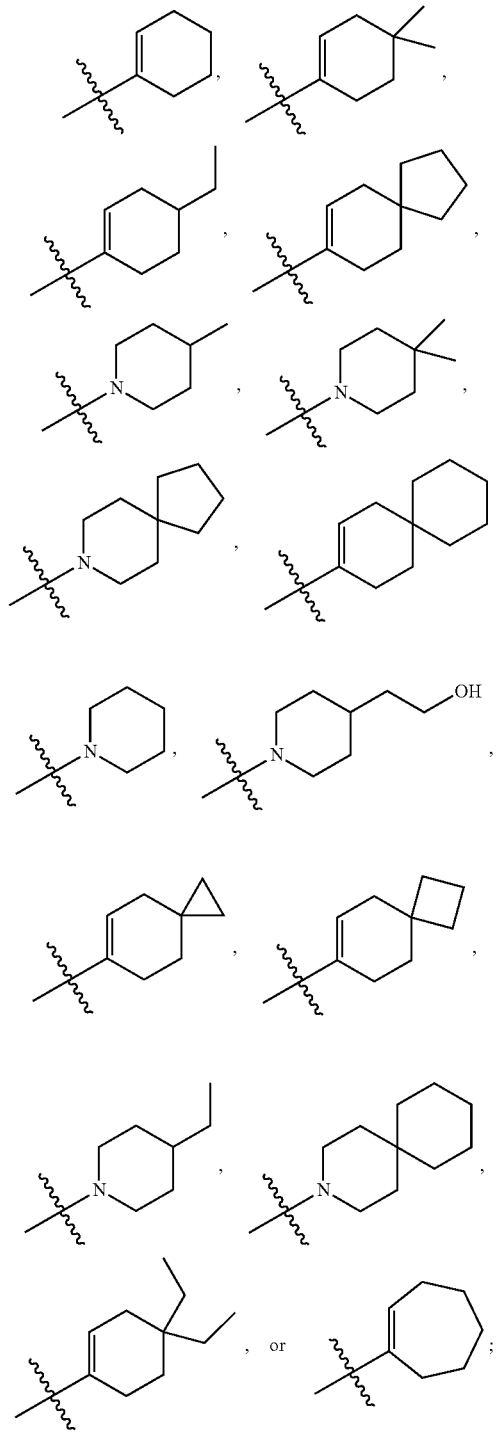

$R^2$ is

X is selected from the group consisting of:

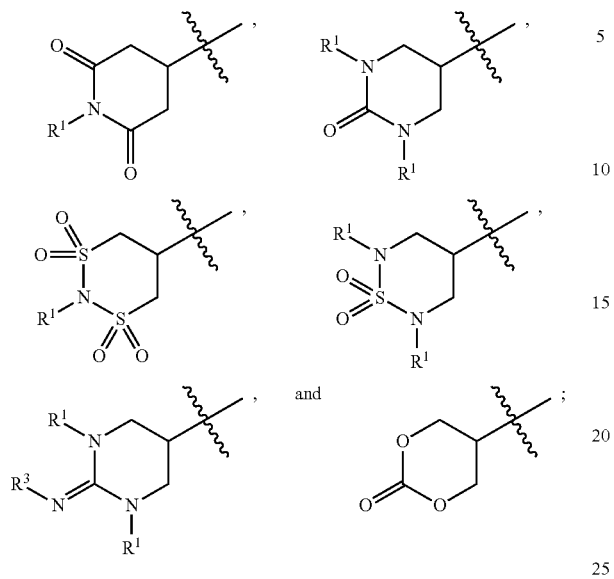

wherein R¹ is H, —CH₃, or —C₂ to C₅ alkyl optionally substituted with one or two of: Me, Et, OH, NH₂, NHMe, NMe₂, NHEt, NEt₂, pyrrolidinyl, pyridyl, morpholino, CONH₂, or COOH and such that when any two heteroatoms are attached to said C₂ to C₅ alkyl group there exists at least two carbon atoms between them, and R³ is —SO₂Me, SO₂Et, —CO₂R⁹, —NO₂, or —CN; wherein R⁹=H, or C$_{(1-3)}$alkyl;

Z is H, C₁-C₃ alkyl or —CH₂OH; and

J is CH or N;

and solvates, hydrates, tautomers and pharmaceutically acceptable salts thereof.

In another embodiment of the invention:

W is

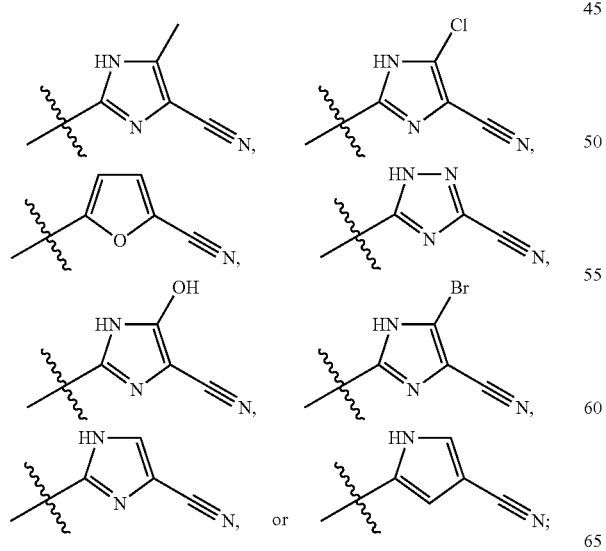

R² is

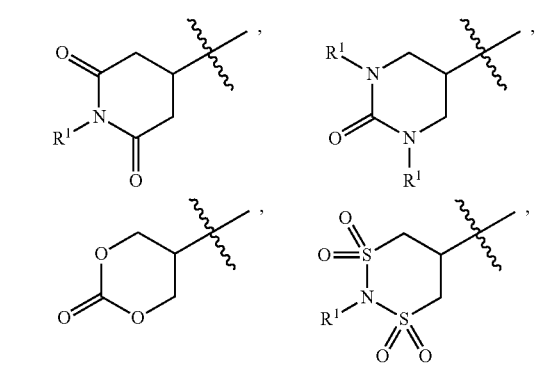

Z is H, or —CH₂OH;

J is CH;

X is selected from the group consisting of

-continued

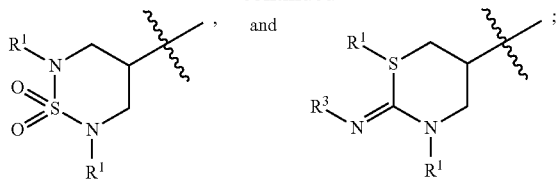

wherein $R^1$ is H, —CH$_2$CH$_3$, —CH$_2$CH$_2$OH, or —CH$_3$; and $R^3$ is —SO$_2$CH$_3$, —CO$_2$CH$_3$, —NO$_2$, or —CN;
and solvates, hydrates, tautomers and pharmaceutically acceptable salts thereof.

In another embodiment of the invention:
W is

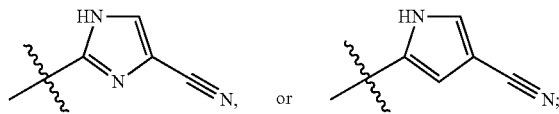 [SMILES: *c1nc(C#N)c[nH]1 ; "or" ; *c1cc(C#N)c[nH]1]

$R^2$ is

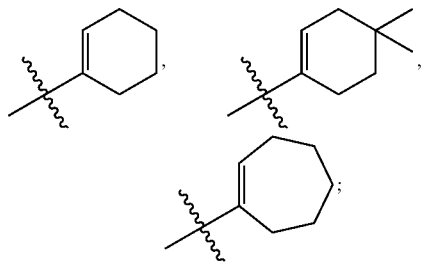

Z is H, or —CH$_2$OH;
J is CH;
X is selected from the group consisting of

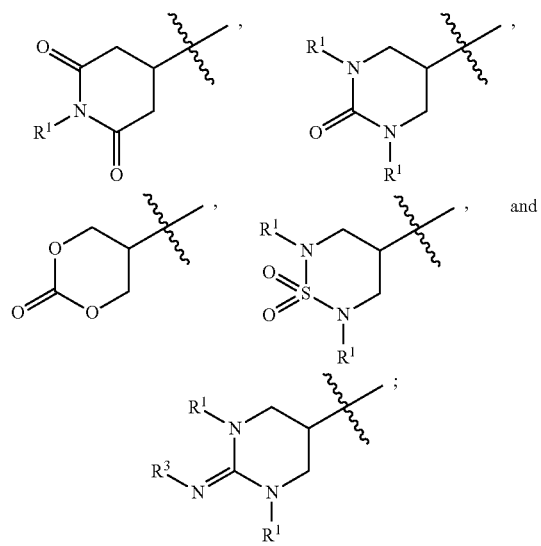

wherein $R^1$ is H, or —CH$_3$; and
$R^3$ is —SO$_2$CH$_3$, or —CN;

and solvates, hydrates, tautomers and pharmaceutically acceptable salts thereof.

An embodiment of the invention is compounds selected from the group consisting of the compounds of Examples 1 and 3 to 53, solvates, hydrates, tautomers and pharmaceutically acceptable salts of these compounds, and any combination thereof.

Still another embodiment is compounds selected from the group consisting of:

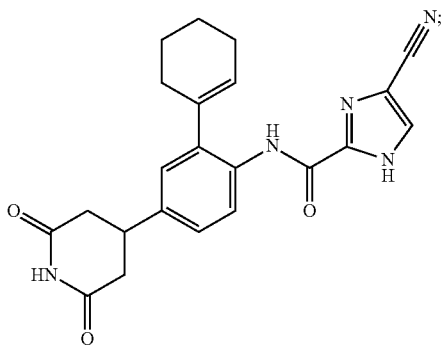

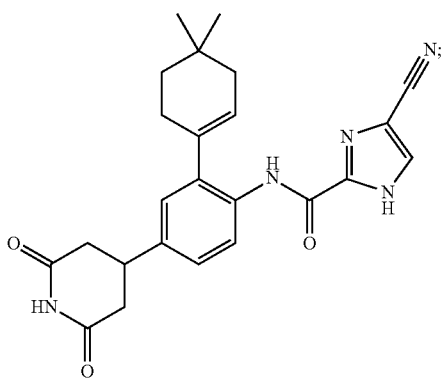

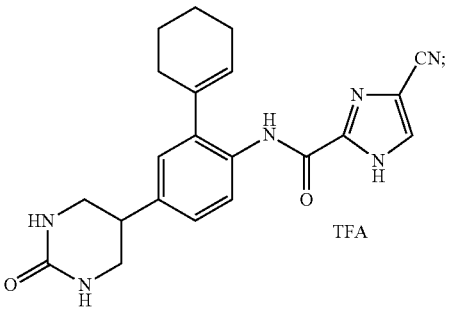

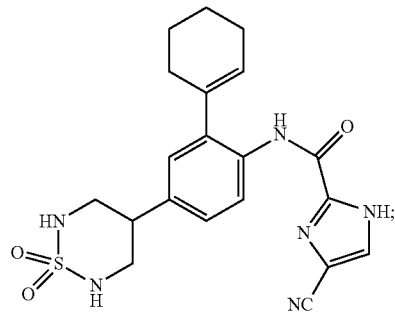

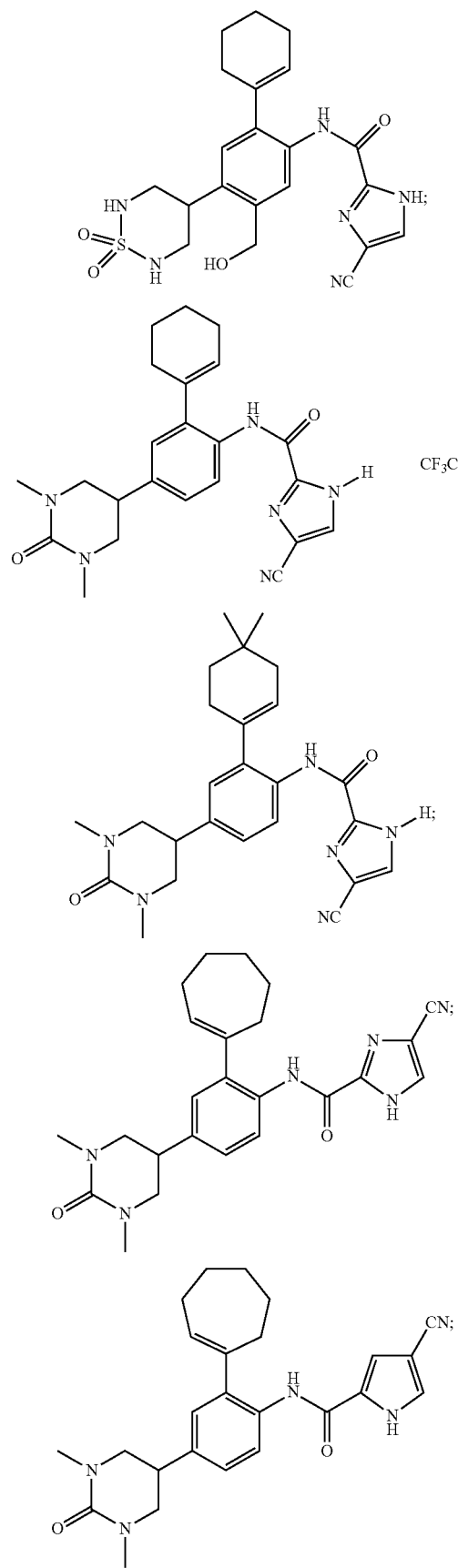
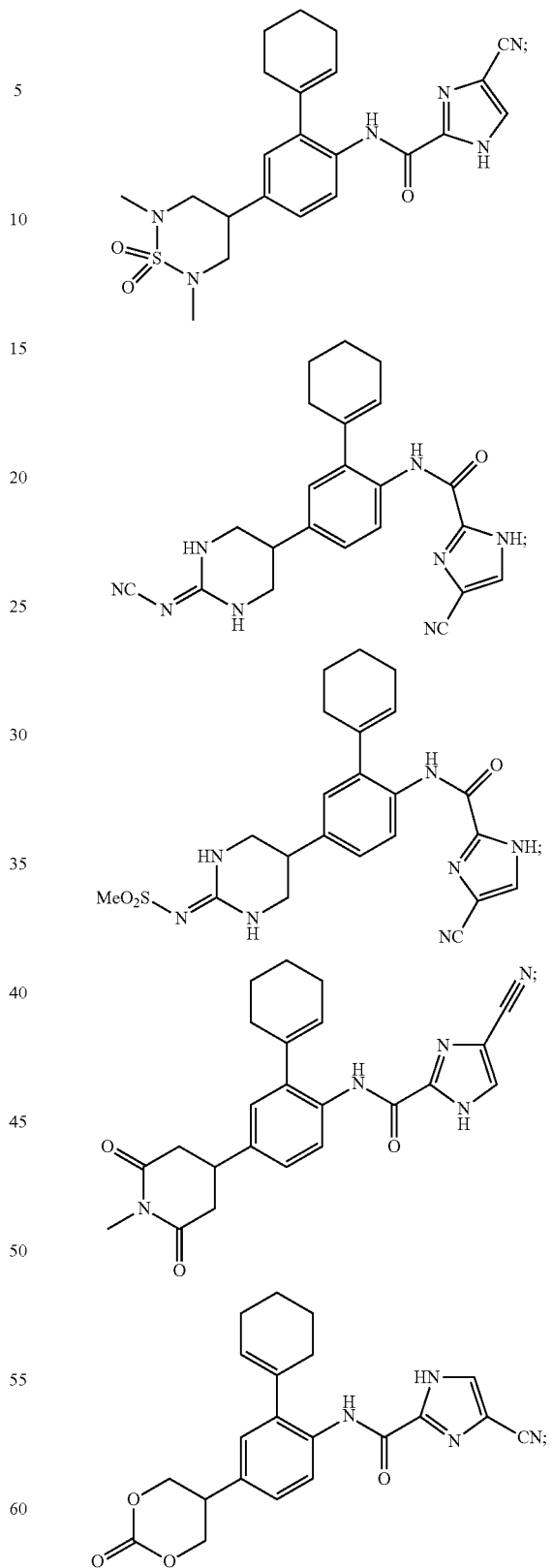
and solvates, hydrates, tautomers and pharmaceutically acceptable salts thereof. The compounds of this embodiment are in Examples 1-15.

Yet another embodiment is a compound selected from the group consisting of:

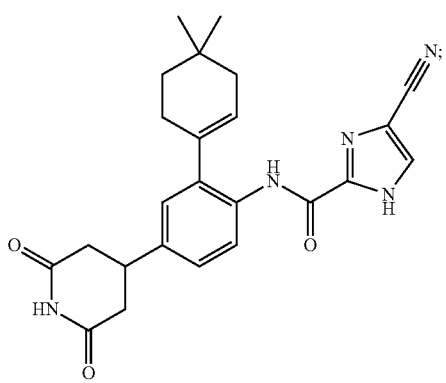

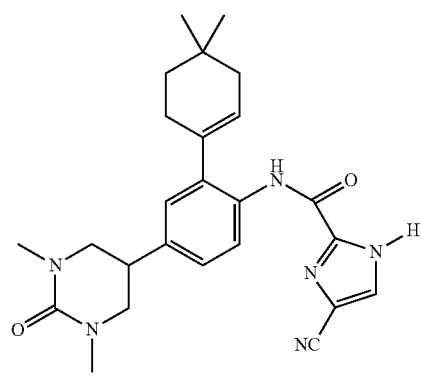

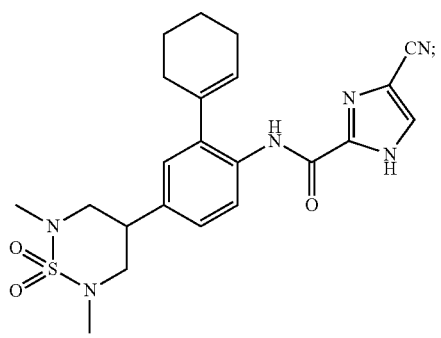

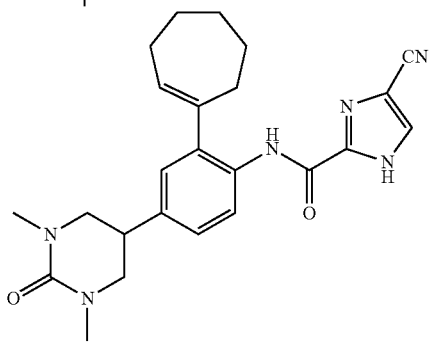

and solvates, hydrates, tautomers and pharmaceutically acceptable salts thereof. The compounds of this embodiment are in Examples 3, 8, 9, and 11.

Another embodiment is the compound

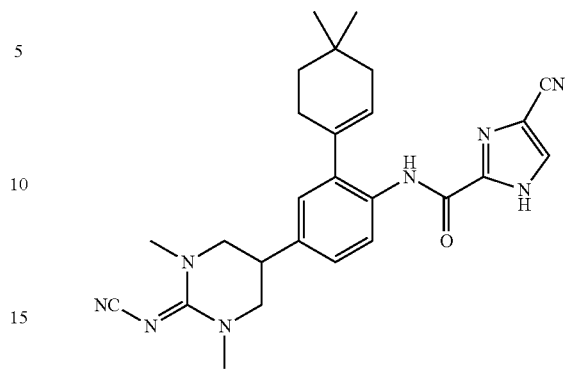

and solvates, hydrates, tautomers and pharmaceutically acceptable salts thereof. The compound of this embodiment is Example 54.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formula I may be prodrugs, i.e., derivatives of an acting drug that possess superior delivery capabilities and therapeutic value as compared to the acting drug. Prodrugs are transformed into active drugs by in vivo enzymatic or chemical processes.

Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "sulfonyl" refers to the group $-S(O)_2R_a$, where $R_a$ is hydrogen, alkyl, cycloalkyl, haloalkyl, aryl, aralkyl, heteroaryl and heteroaralkyl. A "sulfonylating agent" adds the $-S(O)_2R_a$ group to a molecule.

The term "spiro-substituted cycloalkenyl" refers to a pair of cycloalkyl rings that share a single carbon atom and wherein at least one of the rings is partially unsaturated, for example:

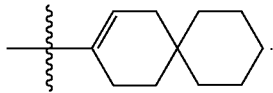

The term "spiro-substituted heterocyclyl" refers to a heterocyclyl and cycloalkyl ring that share a single carbon atom, for example:

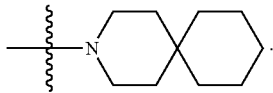

Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, prostate cancer, lung cancer, breast cancer, colon cancer, stomach cancer, and hairy cell leukemia. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, breast cancer, prostate cancer, lung cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Methods of Preparation

Scheme 1

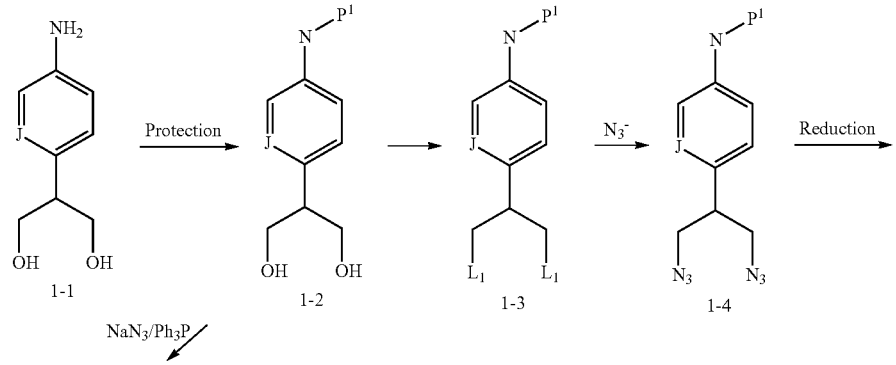

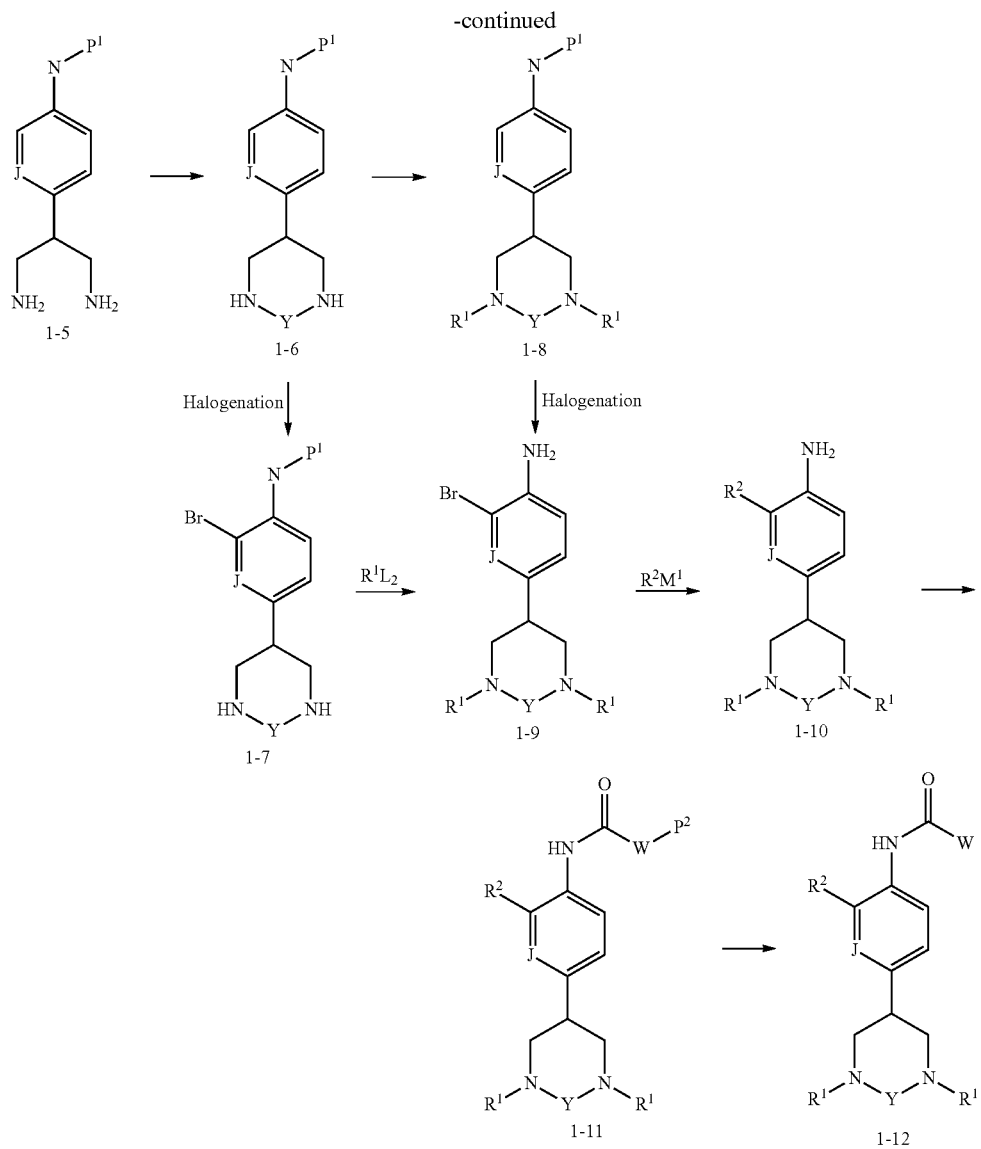

Scheme 1 describes the synthesis of compounds of Formula I where X is

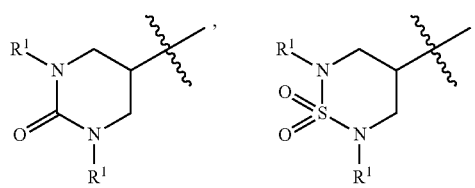

(Y is CO and SO$_2$ in Scheme 1).

Commercially available 2-phenyl-propane-1,2-diol can be converted to aminodiol 1-1 where J is CH according to the procedure described in *Journal of Medicinal Chemistry* 40(25), 4030-4052, (1997). It is understood that when J is N, a similar procedure may be used, starting from (2-pyridyl) propane diol (*Tetrahedron: Asymmetry* 8(13), 2175-2187, (1997)).

Conversion of aminodiol 1-1 to compound 1-2 is accomplished using standard protecting group chemistry. The examples of suitable N-protecting groups P$^1$ can be found in "Protective Groups in Organic Synthesis," by Theodora W. Greene and Peter G. M. Wuts, John Wiley & Sons. Inc, NY, (1999). The preferred protecting group is tert-butyloxycarbonyl (BOC) which can be introduced by reacting aminodiol 1-1 with di-tert-butyldicarbonate ((BOC)$_2$O) in tetrahydrofuran (THF) and aq Na$_2$CO$_3$. The conversion of diol 1-2 to diamine 1-5 can be accomplished via the corresponding diazide 1-4 which can be prepared by the displacement of leaving groups L$^1$ of intermediate 1-3 with azide anion and reduction to diamine 1-5 with known methods such as Ph$_3$P or preferably catalytic hydrogenation. Examples of suitable leaving groups L$^1$ are mesylates, tosylates, triflates and halogens such as Br or I. The L$^1$ in intermediate 1-3 can be introduced by conversion of the diol function of intermediate 1-2 using known literature methods. The preferable leaving group is mesylate which can be prepared by the reaction of diol 1-2 with mesylchloride (MsCl) and a tertiary amine bases such as triethylamine ($Et_3N$) in DCM. Alternatively, intermediate 1-2 can be converted to 1-5 in one step utilizing known synthetic protocols such as $Ph_3P/NaN_3$ (*Synthetic Communications* 30(12), 2233, (2000)) or suitable modification of such protocols.

The transformation of diamine 1-5 to cyclic urea 1-6 (where Y is CO) can be performed by reaction of diamine with carbonylating agents ("phosgene equivalents") such S,S-dimethyldithiocarbonate (DMDTC) (*J. Org. Chem.*, 61, 4175, (1996)), bis(4-nitrophenyl)carbonate (*Helvetica Chimica Acta* 82(8), 1195, (1999)), urea (*J. Chem. Soc., Perkin Trans* 2, 317, (1981)), benzyl succinimidocarbonate (*Bull. Chem. Soc., Jpn.*, 71, 699, (1998)), hexachloroacetone (*Liebigs Annalen/Recueil*, (5), 925, (1997)), triphosgene (*Tett. Lett.*, 32, 4185, (1991)) and carbodiimdazole (*J. Med. Chem.*, 40, 1707, (1997)) at appropriate temperatures and solvents or using complexes of transition metals such as tungsten (*J. Org. Chem.*, 67, 4086, (2002)), Ni (*J. Organomet. Chem.*, 419, 251, (1991)), Pd (*Macromolecules*, 26, 1784, (1993)), Ru (*J. Mol. Catal. A: Chem.*, 122, 103, (1997)), Mn (*Inorg. Chem.* 4, 293, (1965),) and *J. Organomet. Chem.*, 134, 203, (1977)) or Co (*J. Mol. Catal.*, 60, 41, (1990)). The main group elements such as S (*J. Org. Chem.* 26, 3306 and 3309, (1961,)) and Se (*Bull. Chem. Soc., Jpn.*, 60, 1793, (1987)) can also be used to catalyze this transformation.

The preferred method of cyclic urea 1-6 (Y is CO) synthesis is the reaction of diamine 1-5 with bis(4-nitrophenyl)carbonate in 1,2-dichloroethane. The sulfonyl urea 1-6 (Y is $SO_2$) can be produced in analogous fashion by replacing the carbonylating agent with sulfonylating agents such as sulfuryl chloride (*Acta. Chem. Scand*, 17, 2141, (1963)) and sulfamide (*Bioorganic and Medicinal Chemistry*, 13, 755, (2005)). Thus, a reaction of diamine 1-5 with sulfamide in pyridine can be used to produce the sulfonylurea 1-6.

Sulfonylureas and ureas 1-6 can be N-alkylated using known literature procedures (*Synthetic Communications*, 18(5), 487-494 (1988)), WO 9600708, DE 4028040). The preferred methods of alkyation include, but are not limited to, thermal reaction with alkylating agents, such as alkyl halides $R^1L^2$ ($L^2$ is halogen) and sulfates ($R^1OSO_2OR^1$) in the presence of a suitable phase-transfer catalyst such as tetrabutylammonium salts, in solvents such as toluene and dioxane to produce intermediate 1-8 where Y is CO, or $SO_2$, and $R^1$ is alkyl.

The protecting group $P^1$ of intermediate 1-8 (where Y is CO, $SO_2$) can be removed under appropriate conditions to unmask the amine function. For the removal of a BOC group in intermediate 1-8 (where Y is CO, $SO_2$), TFA can be used and the resulting aniline can be isolated as its TFA salt or free base.

The compounds of Formula 1-10, where Y is CO or $SO_2$, can be obtained by ortho-halogenation, preferably bromination, of the deprotected amino compound, followed by metal-catalyzed coupling reactions of bromoamino intermediate 1-9 with boronic acids or boronate esters (Suzuki reactions, where $R^2M^1$ is $R^2B(OH)_2$ or a boronic ester) or tin reagents (Stille reactions, where $R^2M^1$ is $R^2Sn(alkyl)_3$) (for reviews, see N. Miyaura, A. Suzuki, *Chem. Rev.*, 95:2457 (1995), J. K. Stille, *Angew. Chem, Int. Ed. Engl.*, 25: 508024 (1986) and A. Suzuki in Metal-Catalyzed Coupling Reactions, F. Deiderich, P. Stang, Eds., Wiley-VCH, Weinheim (1988)). Similarly, the BOC protected intermediate 1-6 can be ortho-halogenated to obtain intermediate 1-7 which can then be deprotected under acidic condition to produce intermediate 1-9 where $R^1$ is H, and Y is CO or $SO_2$.

The preferred conditions for the above bromination are N-bromosuccinimide (NBS) in a suitable solvent such as N,N-dimethylformamide (DMF), dichloromethane (DCM) or preferably acetonitrile. Metal-catalyzed couplings, preferably Suzuki reactions, can be performed according to standard methodology described above, preferably in the presence of a palladium catalyst such as tetrakis (triphenylphosphine)palladium(0) ($Pd(PPh_3)_4$), an aqueous base such as aq $Na_2CO_3$, and a suitable solvent such as toluene, ethanol, dimethoxyethane (DME), or DMF.

The amino group in compound 1-10 can then be coupled with a heterocyclic acid $P^2$—WCOOH (or a corresponding salt thereof $P^2$—$WCOOM^2$, $M^2$ is Li, Na or K), according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters $WCO_2Rq$ (where Rq is a leaving group such as pentafluorophenyl or N-succinimide) to form the product 1-11. The preferred reaction conditions for coupling with $P^2$—WCOOH or $P^2$—$WCOOM^2$ are: when W is a furan (optional protecting group $P^2$ not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole, 1-(3-dimethylaminopropyl)-3-ethylcarbodiimide hydrochloride (EDCI) and 1-hydroxybenzotriazole-6-sulfonamidomethyl hydrochloride (HOBt); and when W is an imidazole or triazole, the preferred conditions are bromotripyrrolidinophosphonium hexafluorophosphate (PyBrOP) and DIEA in a solvent such as DCM or DMF.

When W in compound 1-11 contains an optional protecting group $P^2$ as mentioned previously, it can be removed at this point. For example, when W is imidazole optionally protected on nitrogen with 2-(trimethylsilyl)ethoxymethyl (SEM), the SEM group can be removed with either acidic reagents such as trifluoroacetic acid TFA or fluoride sources such as tertbutylammonium fluoride (TBAF) to obtain the desired final product 1-12 (Y is CO, $SO_2$). The preferred reaction condition for this deprotection is the treatment of the substrate with TBAF in the presence or absence of ethylene diamine in a suitable solvent such as DMF to produce the final product 1-12.

Scheme 2

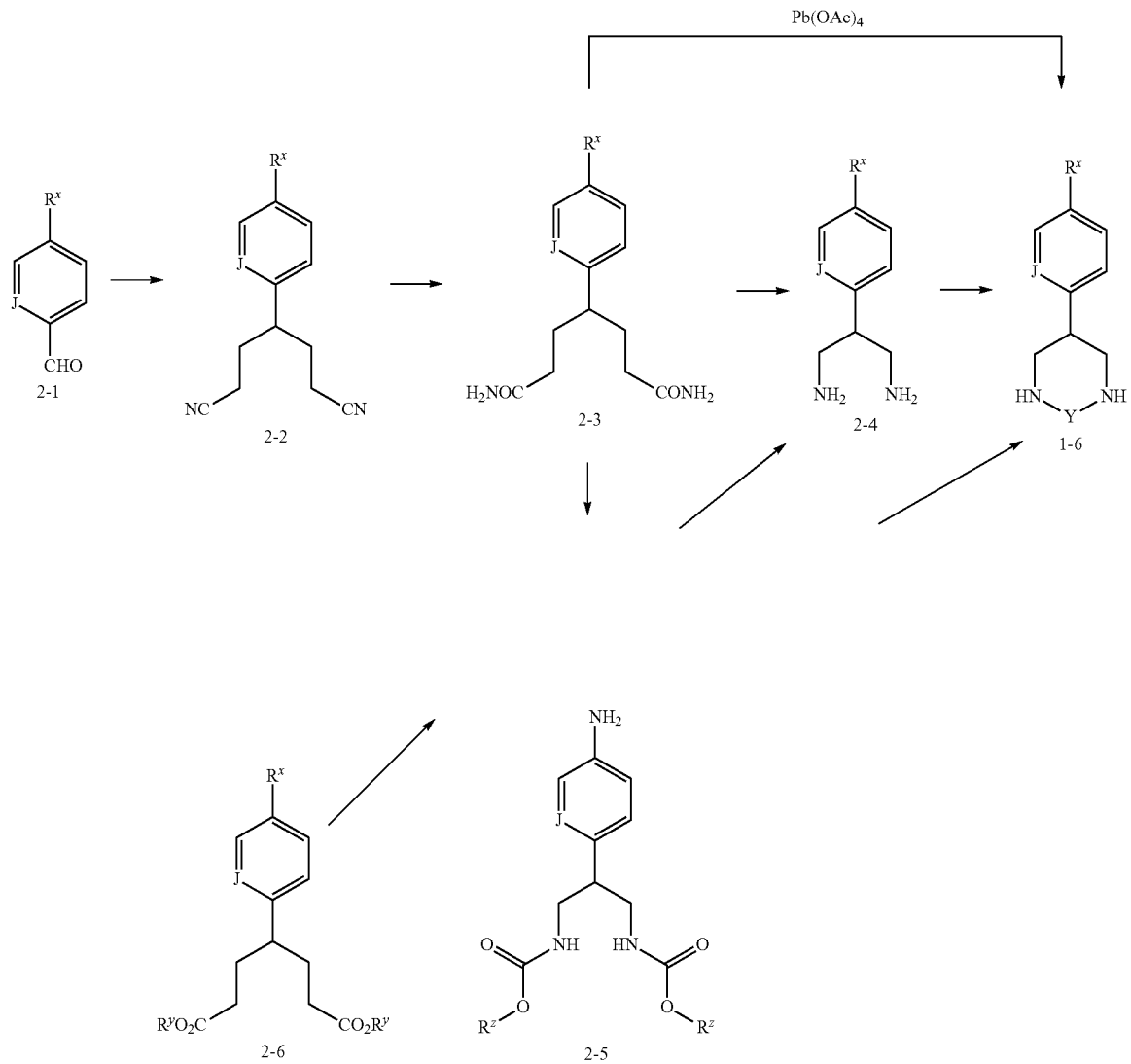

wherein:
P¹ is H;
Y is CO, or SO₂

An alternate synthetic route for the preparation of intermediates of formula 1-6 where Y is CO or SO₂ is shown in Scheme 2. The key intermediate in this synthetic route is 4-substituted phenyl glutaronitrile 2-2 which can be prepared from the corresponding 4-formyl compound 2-1 according to the literature procedures (EP 24776). It is understood that $R^x$ in this synthetic route can be an appropriately protected amine or a functional group which can be converted to an amine such as $NO_2$. $R^x$ can be present in the starting material or it can be introduced at an appropriate step as described in Scheme 1. The nitrile functions of phenylglutaronitrile 2-2 can be hydrolyzed to obtain phenylglutaramide 2-3 according to the appropriate literature procedures (For reference, see "Comprehensive Organic Transformations", by Richard C. Larock, John Wiley & Sons. Inc, NY, (1999). In addition, diester intermediate 2-6 ($R^y$ is alkyl), which can be prepared using procedures analogous to literature procedures (*Journal of the Indian Chemical Society,* 55(9), 897-901, (1978)), can also be converted to phenylglutaramide 2-3 according to the literature procedure (*Synthesis,* (11), 973-4, (1982)).

The phenylglutaramide 2-3 can be converted to desired cyclic urea 1-6 (Y is CO) by means of Hoffman rearrangement either via carbamate intermediate 2-5 with or without isolation (U.S. Pat. No. 6,022,968). In addition it is also understood that cyclic urea 1-6 (Y is CO) can be directly obtained from intermediate 2-3 when the Hoffman rearrangement is initiated with reagents such as Pb(OAc)₄ implementing minor modifications to literature procedures (WO 9943659). It is clear to those who are skilled in the art, the $R^x$ can be manipulated at the appropriate stage to install the amino function in intermediate 1-6 (Y is CO, SO₂). In addition, the carbamate 2-5 ($R^z$ is t-Bu) can also be converted to diamine 2-4 under acidic conditions, preferably TFA. The diamine 2-4 can then be used as a precursor for the synthesis of cyclic ureas and cyclic sulfonylureas 1-6 by the various methods described for the formation of 1-6 in Scheme 1.

Scheme 3

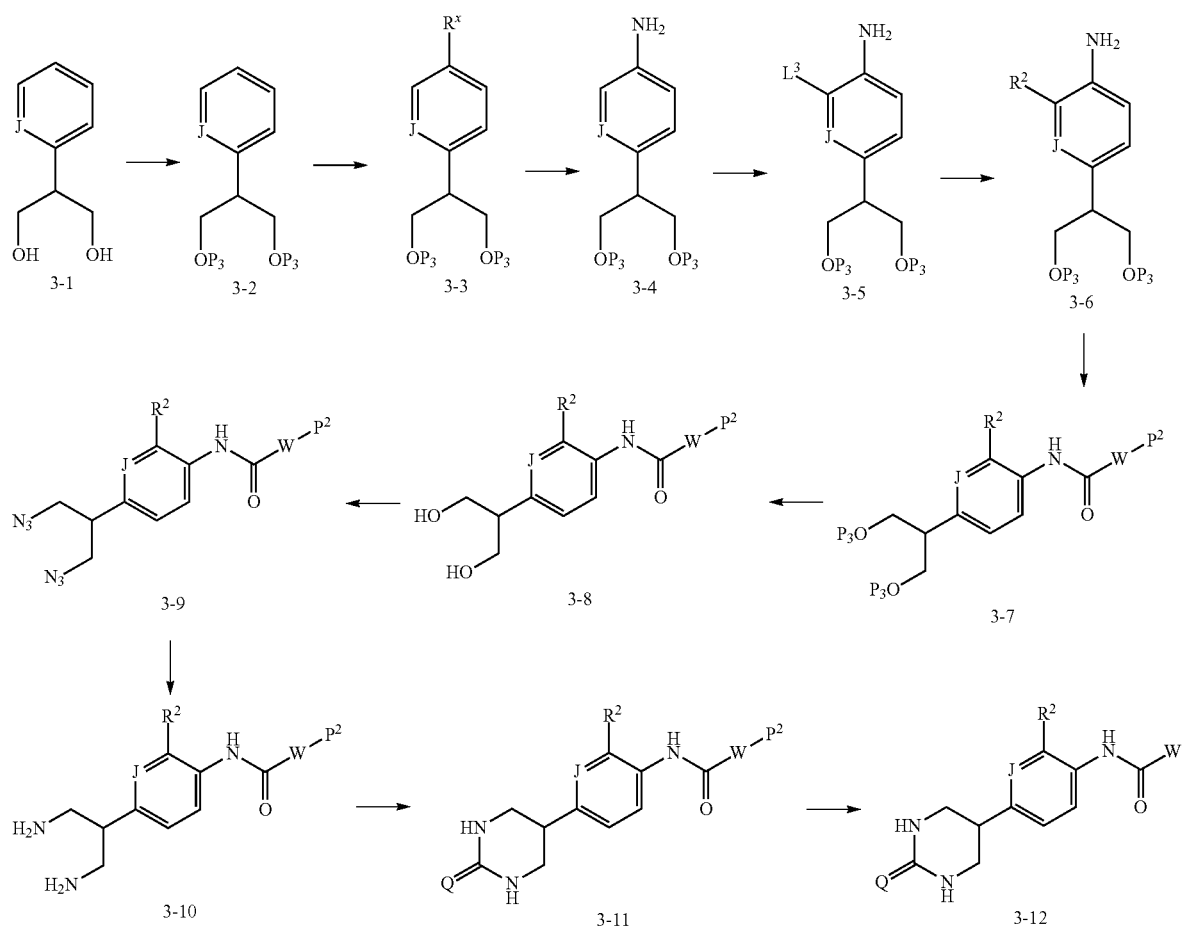

Scheme 3 illustrates another synthetic route for the preparation of cyclic ureas, cyclic sulfonylureas where X is

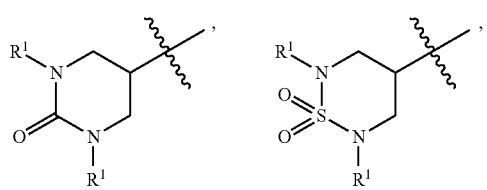

and cyclic guanidines of Formula I where X is

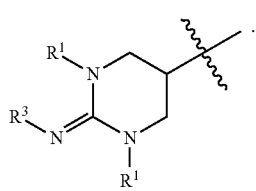

For the illustration of synthetic strategy in this scheme, reagents and conditions are defined for the substrate where J is CH. As previously mentioned in Scheme 1, it is understood that similar synthetic methods can be utilized with minor modification when J is N.

Commercially available 2-phenyl-propane-1,2-diol 3-1 can be employed as the starting material in this synthetic sequence which is protected to give 3-2. The examples of suitable O-protecting groups can be found in "Protective Groups in Organic Synthesis", by Theodora W. Greene and Peter G. M. Wuts, John Wiley & Sons. Inc, NY, (1999). The preferred protection of the diol is the conversion to the corresponding diacetate 3-2 where $P^3$ is Ac (*Tetrahedron*, 46(20), 7081, (1990)).

The conversion of intermediate 3-2 to amine 3-4 can be accomplished by two methods. In one method, halogenation, preferably bromination, of 3-2 followed by either metal-catalyzed amination of the halo intermediate 3-3 (where $R^x$ is halogen) (for reviews, see: S. L. Buchwald, et al, *Top. Curr. Chem.*, 219:131-209 (2001) and J. F. Hartwig in "*Organopalladium Chemistry for Organic Synthesis,*" Wiley Interscience, NY (2002)) can be employed. In the other method compound 3-2 can be nitrated and the nitro intermediate 3-3 (where $R^x$ is $NO_2$) (for references see; *The Nitro Group in Organic Synthesis*" by Noboru Ono, John Wiley & Sons. Inc,) is then reduced. The preferred method for this transformation is nitration of the intermediate 3-2 with conc. $HNO_3$ to obtain compound 3-3 ($R^x$ is $NO_2$), followed by the catalytic hydrogenation to convert the nitro group to the corresponding amino group in 3-4.

The compounds of formula 3-6 can be obtained by ortho-halogenation, preferably bromination, of aniline substrate 3-4 to obtain intermediate 3-5 ($L^3$ is halogen), followed by metal-catalyzed coupling reaction of the latter with a suitable partner as previously described in Scheme 1 to introduce $R^2$. The preferred conditions for bromination of intermediate 3-4 are NBS in a suitable solvent such as DMF, DCM or acetonitrile. The metal-catalyzed couplings, preferably Suzuki reactions, can be performed according to standard methodology as described in Scheme 1, preferably in the presence of a palladium (0) catalyst such as tris(dibenzylideneacetone)dipalladium ($Pd_2(dba)_3$) in the presence of a nonaqueous base such as $K_3PO_4$ and a phosphine ligand such as 2-dicyclohexylphosphino-2',6'-dimethoxy-1,1'-biphenyl (S-Phos) in suitable solvents such as toluene, DME or dioxane.

The compounds in formula 3-7 can be prepared by reaction of compounds of Formula 3-6 with carboxylic acids $P^2$—WCOOH as previously described. The protecting group $P^3$ in intermediate 3-7 can be then removed to unmask the diol function. The preferred method of deprotection involves the saponification of diacetate 3-7 ($P^3$ is Ac) with inorganic bases such as KOH in suitable solvents such as ethyl alcohol (EtOH). The diol function of intermediate 3-8 can be transformed to diamine 3-10 as previously described in Scheme 1, via diazide 3-9, replacing catalytic hydrogenation with an appropriate reduction method which does not reduce an olefin, such as $Zn/NH_4Cl$.

When X is a cyclic guanidine, the diamine can be reacted with appropriate guanidinylating reagents such S,S'-dimethyl cyanodithioimidocarbonate, N-[bis(methylthio)methylene] methanesulfonamide and dimethyl N-nitroimidodithiocarbonate (*Australian Journal of Chemistry*, 46(6), 873, (1993), dimethyl N-nitroimidodithiocarbonate (WO 9204329) and methyl[bis(methylthio)methylene]carbamate (U.S. Pat. No. 3,839,416) to afford compound 3-11 (Q is $NR^3$).

When W in compound 3-11 contains an optional protecting group $P^2$ as mentioned previously it can be removed at this point as described previously in Scheme 1, to obtain the final product 3-12.

When Q is a cyclic urea or sulfonylurea, the diamine 3-10 can also be reacted with carbonylating reagents and sulfonylating reagents as described in Scheme 1 followed again by the removal of $P^2$ if present.

Scheme 4

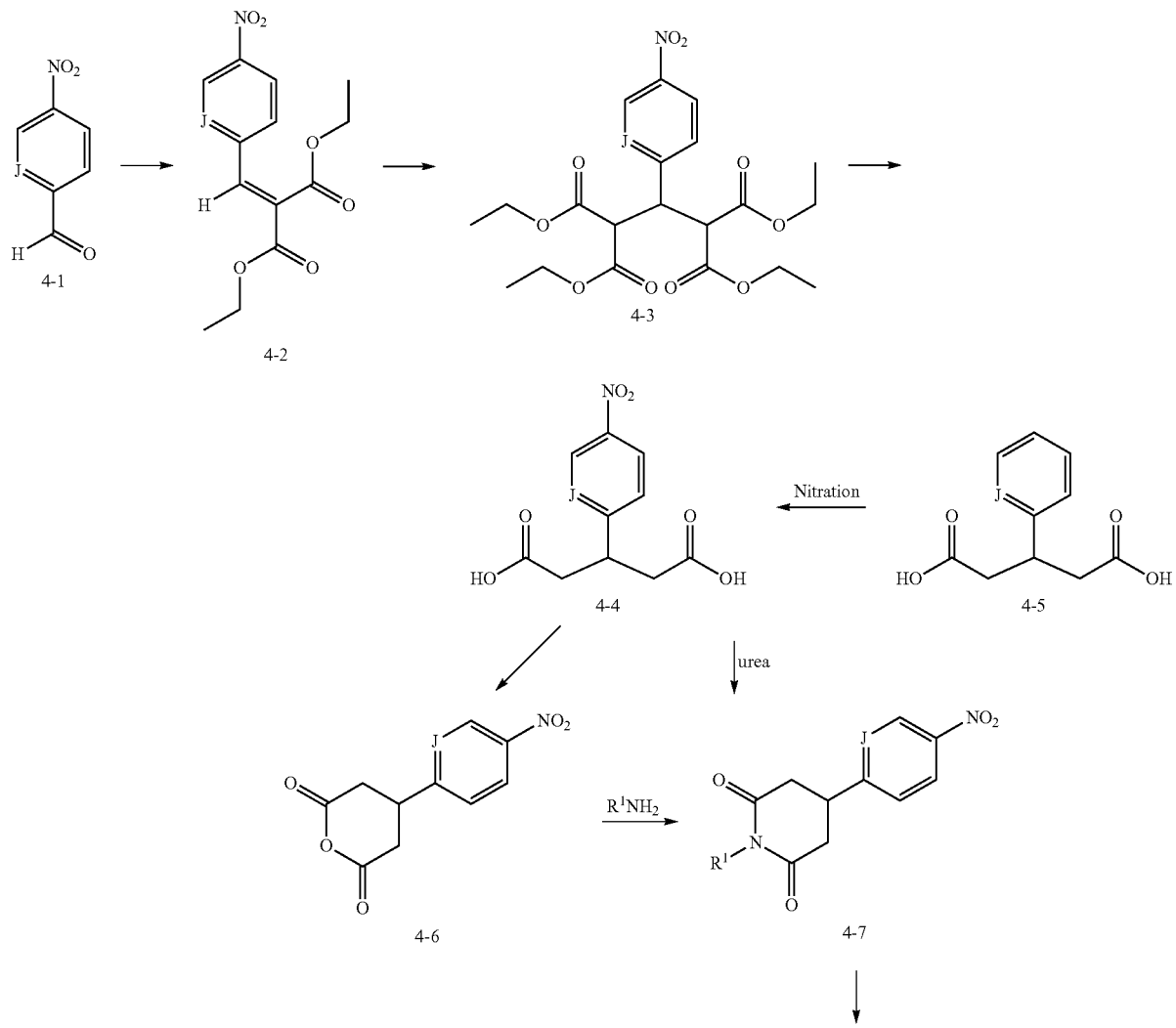

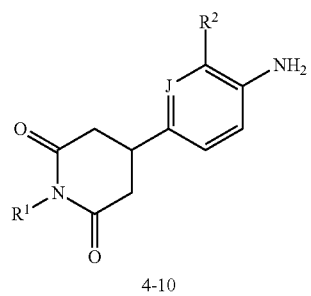

4-10

-continued

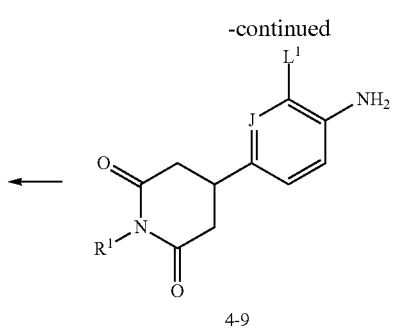

4-9

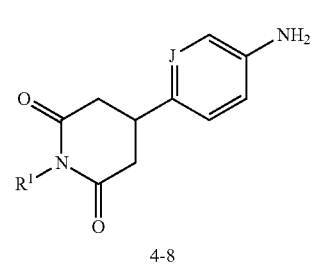

4-8

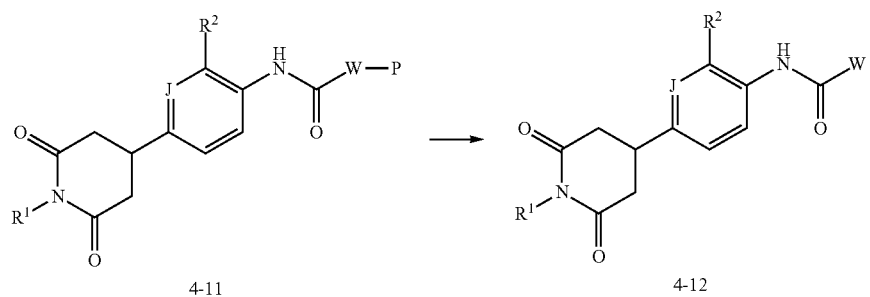

4-11                                    4-12

A synthetic route for the preparation of cyclic imides of Formula 1 where X is

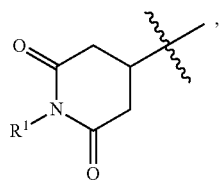

is shown in Scheme 4. It is clear to those who are skilled in the art that, although the reagents and conditions are defined for the substrate where J is CH in order to illustrate the synthetic methodology, similar synthetic methods can be utilized with minor modification when J is N.

The 4-nitrophenylglutaric acid 4-4 can be employed as the key intermediate in this synthetic route. This material can be prepared by direct nitration of phenylglutaric acid 4-5. The preferred condition for this transformation is the treatment of phenylglutaric acid 4-5 with conc. $HNO_3$ (WO 9923063). Alternatively, this substrate can be prepared starting with 4-nitrobenzaldehyde 4-1 via intermediates 4-2 and 4-3 utilizing preparative methods described in literature for the synthesis of phenylglutaric acid (*Journal of Medicinal Chemistry*, 47(8), 1900, (2004)). The construction of the imide ring structure can be accomplished via either conversion of nitrophenyl glutaric acid 4-4 the to the corresponding anhydride 4-6 followed by ring opening with an amine $R^1NH_2$ and subsequent ring closure of the resulting amide acid intermediate to give 4-7. The 4-nitrophenylglutaric acid 4-4, can also be directly converted to imide 4-7 ($R^1$ is H) by fusing it with urea (*Chemistry—A European Journal*, 7(20), 4512, (2001)). In some cases $R^1$ is the group desired in the final product. When the amine $R^1NH_2$ employed in this reaction contains a protecting group such as p-methoxybenzyl (PMB), the unsubstituted imide 4-7, ($R^1$ is H) can be obtained by the removal of the p-methoxybenzyl group by known literature methods (For examples of deprotection methods see: Theodora W. Greene and Peter G. M. Wuts, John Wiley and Sons, Inc., NY (1991)). The preferred method for this transformation is to treat the intermediate 4-7 ($R^1$ is p-methoxybenzyl) with ammonium cerium (IV) nitrate (CAN) (*Bull. Chem. Soc. Jpn.* 58, 1413, (1985)).

The conversion of the nitro group of intermediate 4-7 to obtain amino compound 4-8 can be accomplished by known literature methods as described previously in Scheme 2. The preferred method for this transformation is catalytic hydrogenation. The $R^2$ substituent, can be introduced via ortho-halogenation of intermediate 4-8 and metal-catalyzed coupling reactions of resulting product 4-9 (where $L^1$ is halogen, preferably Br) as previously described to give 4-10.

Compound 4-11 can be prepared by reaction of compound 4-10 with carboxylic acids $P^2$—WCOOH as previously described in Scheme 1. When W in compound 4-11 contains optional protection $P^2$ as mentioned previously, it can be removed as described in Scheme 1 to obtain the final product 4-12.

Scheme 5

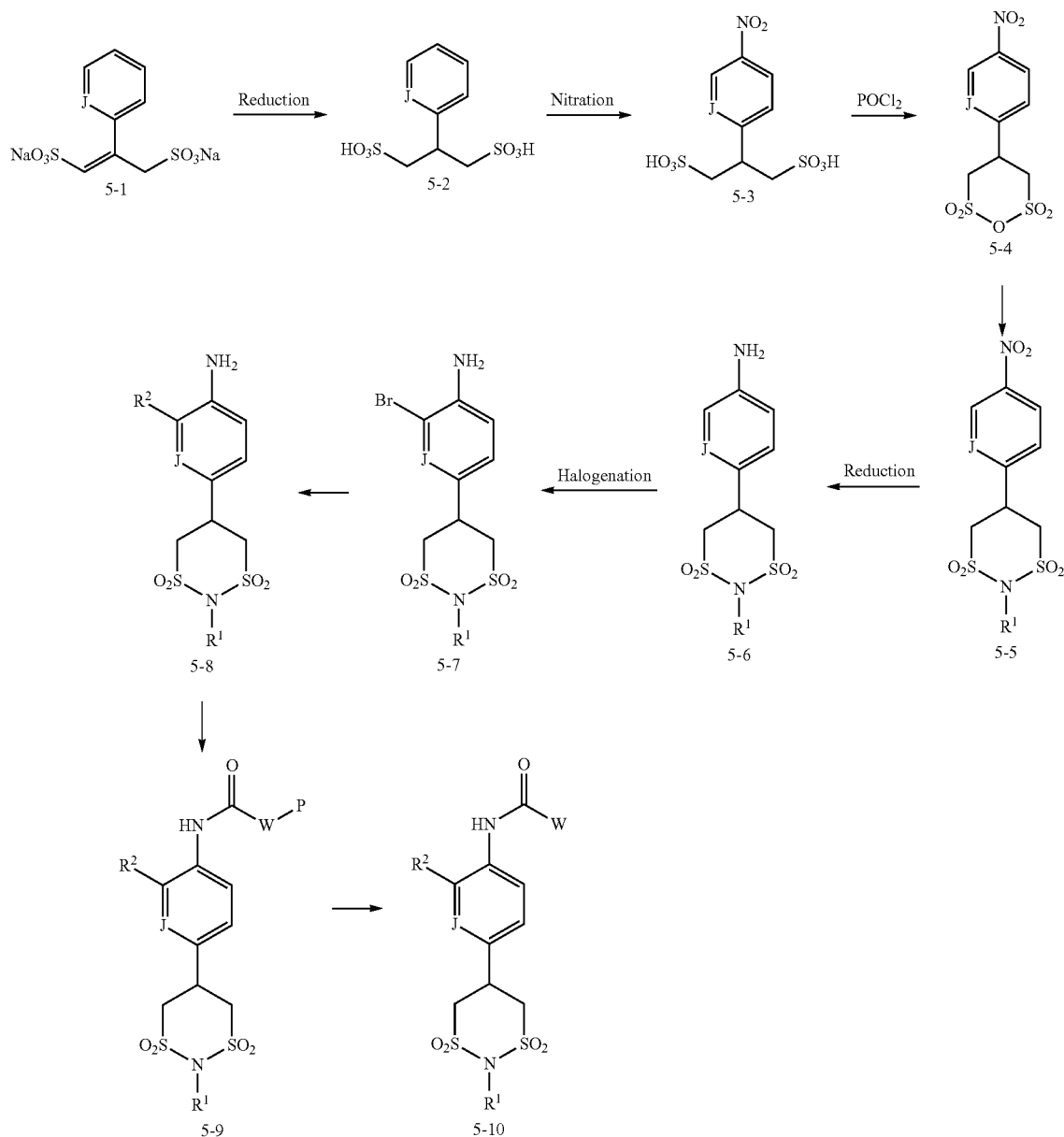

A synthetic route for the preparation of compounds of Formula I where X is

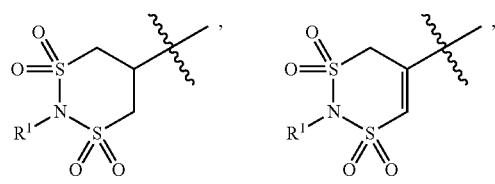

is shown in Scheme 5. It is clear to those who are skilled in the art that, although the reagents and conditions are defined for the substrate where J is H in order to illustrate the synthetic methodology, similar synthetic methods can be utilized with minor modification when J is N.

2-Phenyl-1-propene-1,3-disulfonic acid 5-1 (*J. Amer. Chem. Soc.*, 66, 1105-9, (1944)) can be employed as the starting material in this synthesis (J is CH). This material can be subjected to catalytic hydrogenation to obtain 5-2 which can then be nitrated as described in Scheme 4 to obtain intermediate 5-3. Intermediate 5-3 can be converted to anhydride 5-4 according to the literature procedure (*Chem. Ber.* 91, 1512-15, (1958)). The cyclic sulfonimide 5-5 can be obtained from intermediate 5-4 utilizing the synthetic methodology described in Scheme 4 for the conversion of anhydride 4-6 to cyclic imide 4-7. In some cases, cyclization of an intermediate sulfonamidosulfonic acid may be required using methods described in the literature (*Ann.*, 657, 86-94 (1962)), preferably using $POCl_3$. The nitro group of intermediate 5-5 can be reduced to an amino group to obtain intermediate 5-6 which can be carried through the next 4 steps employing the chemistry described for the conversion of intermediate 4-8 to 4-12 as described in Scheme 4.

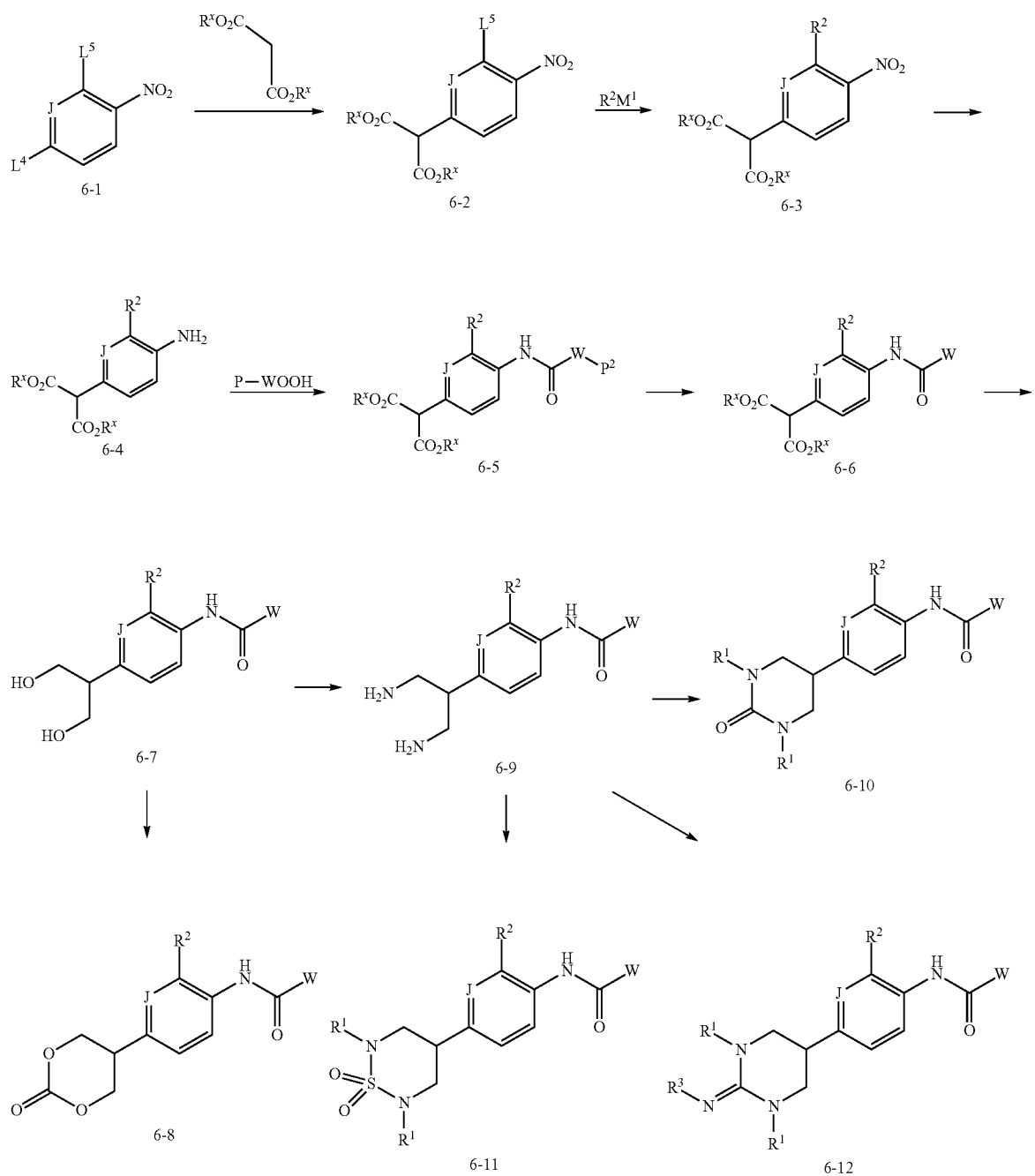
Scheme 6 illustrates the synthetic route for the preparation of cyclic carbonates of Formula 1 where X is
and alternative routes for the preparation of cyclic ureas and cyclic sulfonylureas of Formula 1 where X is
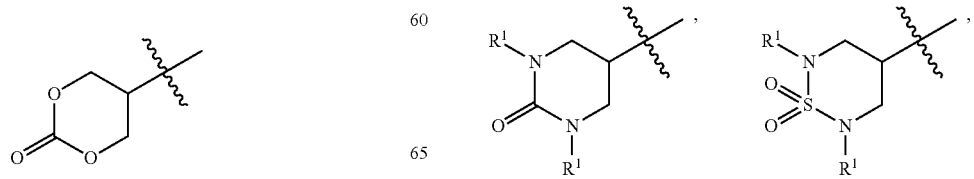

($R^1$ is H), respectively, and for cyclic guanidines of Formula 1 where X is

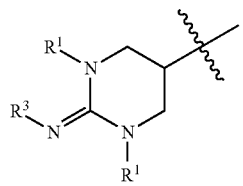

($R^1$ is H). Starting material 6-1 is a dihalonitro compound where leaving group $L^4$ is chloro or preferably fluoro and where $L^5$ is bromo or iodo. Compound 6-1 can be reacted with a dialkyl malonate, for example diethyl malonate ($R^x$ is Et) or preferably dimethyl malonate ($R^x$ is Me), in a polar aprotic solvent, such as N,N-dimethylacetamide (DMA), dimethylsulfoxide (DMSO) or preferably N,N-dimethylformamide (DMF), in the presence of a base, such as KH, LiH, KOtBu or preferably NaH to afford compound 6-2. The second halide $L^5$ in compound 6-2 can then undergo a metal-catalyzed coupling reaction with a boronic acid or a boronate ester (Suzuki reactions where $R^2M^1$ is $R^2B(OH)_2$, for example, cyclohexan-1-enyl boronic acid, or $R^2B(OR)_2$ where $(OR)_2$ is pinacolato, respectively) or with tin reagents (Stille reactions, where $R^2M^1$ is $R^2Sn(alkyl)_3$) in the presence of a suitable palladium catalyst such as $Pd(Ph_3P)_4$ or preferably dichloro[1,1'-bis(diphenylphosphino)ferrocene]palladium (II) (Pd(dppf)$Cl_2$) and an appropriate base, such as $Cs_2CO_3$ or preferably $K_3PO_4$ to give compound 6-3. For reviews of these couplings reactions, see N. Miyaura, A. Suzuki, *Chem. Rev.*, 95, 2457 (1995), J. K. Stille, *Angew. Chem, Int. Ed. Engl.*, 25, 508-24 (1986) and A. Suzuki in Metal-Catalyzed Coupling Reactions, F. Deiderich, P. Stang, Eds., Wiley-VCH, Weinheim (1988).

The nitro group in compound 6-3 can be reduced to an amino group by a reducing agent which will not reduce an olefin, such as iron powder in the presence of $NH_4Cl$ in a solvent such as aqueous ethanol, to form amine 6-4.

The amino group in compound 6-4 can then be coupled with a heterocyclic acid $P^2$—WCOOH (or a corresponding salt thereof $P^2$—WCOO$M^2$, $M^2$ is Li, Na or K), according to the procedures for amide bond formation as described in Scheme 1 to form the amide product 6-5 ($P^2$ is optional protecting group as defined in Scheme 1). The optional protecting group on W, if present, in compound 6-5, such as 2-(trimethylsilyl)ethoxy-methyl (SEM) optionally used to protect a nitrogen when W contains an imidazole or triazole, can be removed under the conditions described in Scheme 1, preferably acidic conditions and most preferably with trifluoroacetic acid, to give compound 6-6. Alternatively the optional protecting group $P^2$ can be removed with a fluoride reagent, preferably tetrabutylammonium fluoride in a suitable solvent such as DMF or THF.

The two ester groups in compound 6-6 can be selectively reduced by an appropriate reducing agent, such as sodium borohydride in the presence of suitable solvents, such as a mixture of methanol and tert-butanol, to form compound 6-7.

Diol 6-7 can be reacted with an appropriate carbonylation agent, such as phosgene, carbonyldiimidazole, bis(4-nitrophenyl) carbonate or preferably triphosgene, in the presence of a base, such as pyridine or lutidine, in an organic solvent, such as THF, to give compound 6-8.

Diol 6-7 can also serve as a precursor to diamine 6-9 by the methodology described in Scheme 3 for the conversion of diol 3-8 to diamine 3-10. Diamine 6-9 is useful for the synthesis of cyclic ureas 6-10 ($R^1$ is H) and cyclic sulfonylureas 6-11 ($R^1$ is H) as described for the synthesis of compound 1-6 in Scheme 1, and, for the synthesis of cyclic guanidines 6-12 ($R^1$ is H) as described for the synthesis of compound 3-10 in Scheme 3).

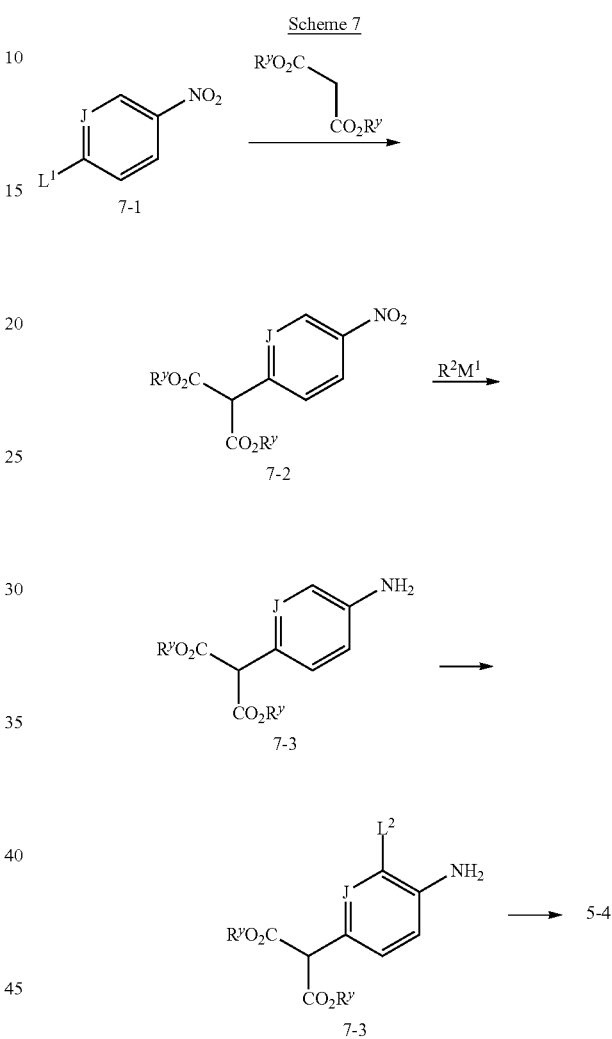

Scheme 7

An alternative route to intermediate 6-4 of Scheme 6 is illustrated in Scheme 7 and is particularly useful for the synthesis of the compounds 6-8, 6-10, 6-11 and 6-12 as shown in Scheme 6 where J is N.

Compound 7-1 may serve as a starting material where $L^1$ is chloro or preferably fluoro and can be substituted by a malonate ester as described in Scheme 6 to give compound 7-2. Reduction of nitro compound 7-2 to amine 7-3 can be carried out by any of a number of standard reduction methods (as reviewed in M. Hudlicky, "Reductions in Organic Chemistry," Wiley, NY (1984)), preferably with hydrogen over a suitable catalyst such as palladium on carbon in an appropriate solvent such as ethanol.

Halogenation, preferably bromination, of amine 7-3 to introduce $L^2$ can be carried as described in Scheme 1 for the preparation of compound 1-9. Suzuki coupling with a boronic acid or boronic ester $R^2M^1$ as described in Scheme 6 can then provide intermediate 6-4 which is carried on to the final compounds as also described in Scheme 6.

Scheme 8

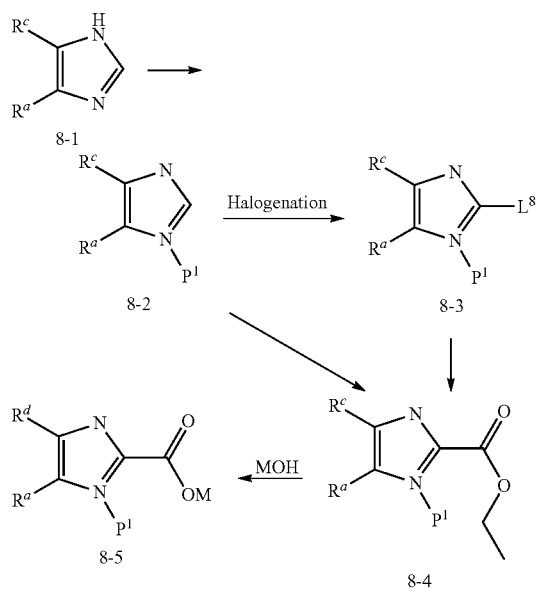

Scheme 8 illustrates a route to the preparation of 2-imidazolecarboxylates of Formula 8-5 where $R^a$ is H or $C_{(1-4)}$alkyl, and $R^d$ is H, alkyl, —CN, or —CONH$_2$ that are used as intermediates in the synthesis of compounds of Formula I where W is imidazole.

Imidazoles of Formula 8-1 where $R^a$ is H or $C_{(1-4)}$alkyl, and $R^c$ is H, $C_{(1-4)}$alkyl or —CN are either commercially available or, in the case where $R^c$ is —CN, are readily available from commercially available aldehydes (8-1 where $R^c$ is CHO) by reaction with hydroxylamines followed by dehydration with a suitable reagent such as phosphorus oxychloride or acetic anhydride (Synthesis, 677, 2003). Imidazoles of Formula 8-1 are protected with a suitable group ($P^1$) such as a methoxymethylamine (MOM), or preferably a SEM group to give compounds of Formula 8-2 (see Theodora W. Greene and Peter G. M. Wuts, Protective Groups in Organic Synthesis, John Wiley and Sons, Inc., NY (1991)).

Imidazoles of Formula 8-2, where $R^c$ is —CN, are halogenated with a suitable reagent such as N-bromosuccinimide or N-iodosuccinimide under either electrophilic conditions in a solvent such as DCM or CH$_3$CN or under radical conditions in the presence of an initiator such as azobis(isobutyronitrile) (AIBN) in a solvent such as CCl$_4$ to give compounds of Formula 8-3 where $L^8$ is a leaving group (preferably bromo or iodo). Halogen-magnesium exchange on compounds of Formula 8-3 provides the organomagnesium species, which is then reacted with a suitable electrophile to provide compounds of Formula 8-4. The preferred conditions for halogen-magnesium exchange are using an alkyl-magnesium reagent, preferably isopropylmagnesium chloride in a suitable solvent such as THF at temperatures between –78° C.-to 0° C. The preferred electrophiles are ethyl chloroformate or ethyl cyanoformate. For examples of halogen-magnesium exchange on cyanoimidazoles see J. Org. Chem. 65, 4618, (2000).

For imidazoles of Formula 8-2, where $R^c$ is not —CN, these may be converted directly to imidazoles of Formula 8-4 by deprotonation with a suitable base such as an alkyllithium followed by reaction with an electrophile as described above for the organomagnesium species. The preferred conditions are treating the imidazole with n-butyllithium in THF at –78° C. and quenching the resulting organolithium species with ethyl chloroformate (for examples, see Tetrahedron Lett., 29, 3411-3414, (1988)).

The esters of Formula 8-4 may then be hydrolyzed to carboxylic acids (M is H) or carboxylate salts (M is Li, Na, or K,) of Formula 8-5 using one equivalent of an aqueous metal hydroxide (MOH) solution, preferably potassium hydroxide in a suitable solvent such as ethanol or methanol. Synthesis of compounds of Formula 8-5 where $R^d$ is —CONH$_2$ is accomplished by first treating compounds of Formula 8-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

Scheme 9

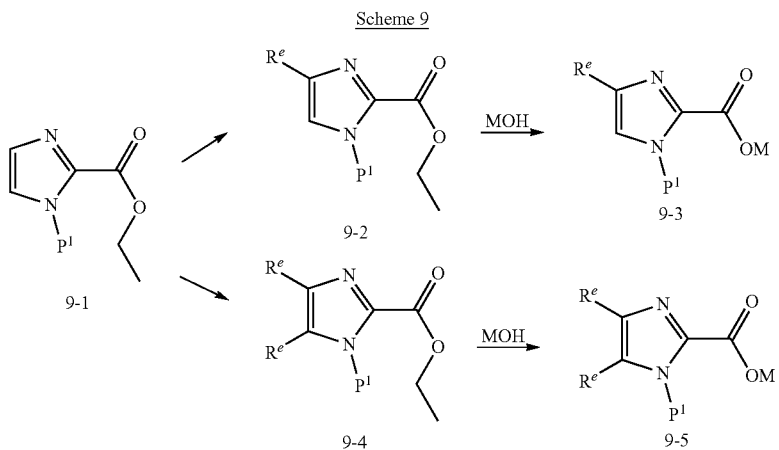

Scheme 9 illustrates a route to 2-imidazolecarboxylates of Formula 9-3 or 9-5 where $R^e$ is chloro or bromo, and M is H, Li, K, or Na that are used as intermediates in the synthesis of compounds of Formula I where W is imidazole.

Compounds of Formula 9-1 are first prepared by protection of commercially available ethyl imidazolecarboxylate according to the methods outlined in Scheme 8, preferably with a SEM group.

Compounds of Formula 9-2 are prepared by reaction of compounds of Formula 9-1 with one equivalent of an appropriate halogenating reagent, such as NBS or N-chlorosuccinimide (NCS) in a suitable solvent such as CH₃CN, DCM or DMF at 25° C. Compounds of Formula 9-4 are prepared by reaction of compounds of Formula 9-1 with two equivalents of an appropriate halogenating reagent, such as NBS or NCS in a suitable solvent such as CH₃CN or DMF at temperatures between 30° C. to 80° C. Imidazoles of Formula 9-3 and 9-5 are then obtained from the respective esters by hydrolysis as described in Scheme 8.

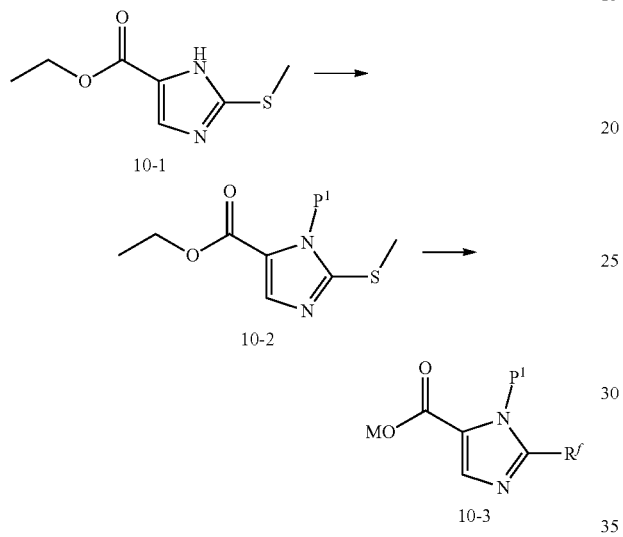

Scheme 10 illustrates a method for the preparation of imidazoles of Formula 10-3 where $R^f$ is —SCH₃, —SOCH₃, or —SO₂CH₃, M is H, Li, K, or Na that are used as intermediates in the synthesis of compounds of Formula I where W is imidazole. Imidazole 10-1 (WO 1996011932) is protected according to the methods described in Scheme 8, preferably with a SEM protecting group to give compounds of Formula 10-2. Ester hydrolysis according to the procedure in Scheme 8 gives compounds of Formula 10-3 where $R^f$ is —SCH₃. Oxidation of 2-methylthioimidazoles of Formula 10-2 with one equivalent of an appropriate oxidant, followed by ester hydrolysis according to the procedure in Scheme 8 gives compounds of Formula 10-3 where $R^f$ is —SOCH₃. Oxidation with two equivalents of an appropriate oxidant, followed by ester hydrolysis according to the procedure in Scheme 8 gives compounds of Formula 10-3 where $R^f$ is —SO₂CH₃. The preferred reagent for oxidation is MCPBA in DCM. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with NaIO₄ (see, for example, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of H₂O₂ respectively, in the presence of titanium (IV) isopropoxide (see, for example, *J. Chem. Soc., Perkin Trans.* 2, 1039-1051 (2002)).

EXAMPLES

The following examples are for exemplary purposes only and are in no way meant to limit the invention.

Example 1

4-Cyano-1H-imidazole-2-carboxylic acid [2-cyclohex-1-enyl-4-(2,6-dioxo-piperidin-4-yl)-phenyl]-amide

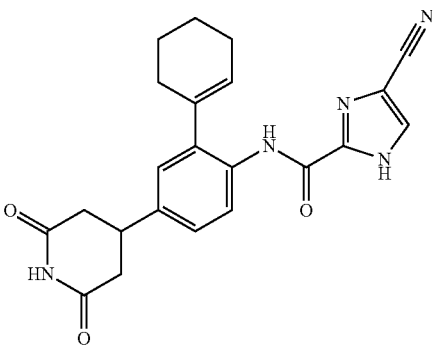 [SMILES: N#Cc1c[nH]c(C(=O)Nc2ccc(C3CC(=O)NC(=O)C3)cc2C2=CCCCC2)n1]

a) 1-(2-Trimethylsilanyl-ethoxymethyl)-1H-imidazole-4-carbonitrile

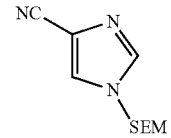 [SMILES: C[Si](C)(C)CCOCn1cnc(C#N)c1]

A flask charged with imidazole-4-carbonitrile (0.50 g, 5.2 mmol) (Synthesis, 677, 2003), 2-(trimethylsilyl)ethoxymethyl chloride (SEMCl) (0.95 mL, 5.3 mmol), K₂CO₃ (1.40 g, 10.4 mmol), and acetone (5 mL) was stirred for 10 h at RT. The mixture was diluted with ethyl acetate (EtOAc) (20 mL) and washed with water (20 mL) and brine (20 mL) and the organic layer dried over MgSO₄. The crude product was eluted from a 20-g SPE cartridge (silica) with 30% EtOAc/hexane to give 0.80 g (70%) of the title compound as a colorless oil: Mass spectrum (CI (CH₄), m/z) Calcd. for C₁₀H₁₇N₃OSi, 224.1 (M+H). found 224.1.

b) 2-Bromo-1-(2-trimethylsilanyl-ethoxymethyl)-1H-imidazole-4-carbonitrile

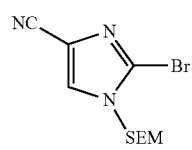 [SMILES: C[Si](C)(C)CCOCn1cc(C#N)nc1Br]

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added N-bromosuccinimide (NBS) (0.61 g, 3.4 mmol) and azobis(isobutyronitrile) (AIBN, catalytic), and the mixture was heated at 60° C. for 4 h. The reaction was diluted with EtOAc (30 mL), washed with NaHCO$_3$ (2×30 mL), brine (30 mL), the organic layer was dried over Na$_2$SO$_4$ and then concentrated. The title compound was eluted from a 20-g SPE cartridge (silica) with 30% EtOAc/hexane to give 0.73 g (77%) of a yellow solid: Mass spectrum (CI (CH$_4$), m/z) Calcd. for C$_{10}$H$_{16}$BrN$_3$OSi, 302.0/304.0 (M+H). found 302.1/304.1.

c) 4-Cyano-1-(2-trimethylsilanyl-ethoxymethyl)-1H-imidazole-2-carboxylic acid ethyl ester

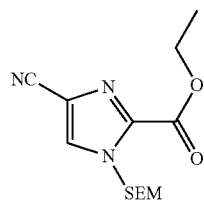 [SMILES: CCOC(=O)c1nc(C#N)cn1COCC[Si](C)(C)C]

To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added drop wise a solution of 2 M isopropylmagnesium chloride (i-PrMgCl) in THF (1 mL). The reaction was allowed to stir for 10 min at −40° C. and then cooled to −78° C., and ethyl cyanoformate (0.30 g, 3.0 mmol) was added. The reaction allowed to attain RT and stirred for 1 h. The reaction was quenched with satd aq NH$_4$Cl, diluted with EtOAc (20 mL), washed with brine (2×20 mL). The organic layer was dried over Na$_2$SO$_4$ and then concentrated. The title compound was eluted from a 20-g SPE cartridge (silica) with 30% EtOAc/hexane to give 0.40 g (74%) of a colorless oil: Mass spectrum (ESI, m/z): Calcd. for C$_{13}$H$_{21}$N$_3$O$_3$Si, 296.1 (M+H). found 296.1.

d) 4-Cyano-1-(2-trimethylsilanyl-ethoxymethyl)-1H-imidazole-2-carboxylate potassium salt

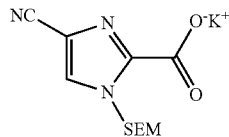

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.2 mL) and the reaction was stirred for 10 min and then concentrated to give 0.40 g (100%) of the title compound as a yellow solid: $^1$H-NMR (CD$_3$OD; 400 MHz): δ 7.98 (s, 1H), 5.92 (s, 2H), 3.62 (m, 2H), 0.94 (m, 2H), 0.00 (s, 9H). Mass spectrum (ESI-neg, m/z): Calcd. for C$_{11}$H$_{16}$KN$_3$O$_3$Si, 266.1 (M-K). found 266.0.

e) 2-(4-Nitro-benzylidine)-malonic acid diethyl ester

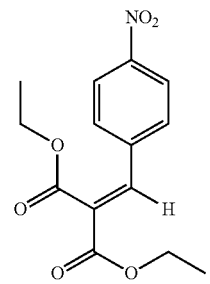 [SMILES: CCOC(=O)C(=Cc1ccc([N+](=O)[O-])cc1)C(=O)OCC]

A solution of 3.00 g (19.9 mmol) of 4-nitro-benzaldehyde in toluene (30 mL) was treated with 3.62 mL (23.8 mmol) of malonic acid diethyl ester and 0.5 mL of piperidine. The mixture was heated to 100° C. for 24 h, cooled to room temperature (RT), diluted with toluene (80 mL) and washed with water (1×100 mL), saturated aqueous NaHCO$_3$ (1×100 mL), and 1.0 M aqueous HCl (1×100 mL). The organic layer was dried (MgSO$_4$) and concentrated in vacuo. Silica gel chromatography of the residue with 25% EtOAc-hexane afforded 5.09 g (87%) of the title compound: $^1$H-NMR (CDCl$_3$; 400 MHz): δ 8.25 (d, 2H, J=8.8 Hz), 7.77 (s 1H), 7.63 (d, 2H, J=8.8 Hz), 4.35 (qd, 4H, J=7.2, 2.0 Hz), 1.30 (t, 6H, J=7.2 Hz).

f) 2,4-Bis-ethoxycarbonyl-3-(4-nitro-phenyl)-pentanedioic acid diethyl ester

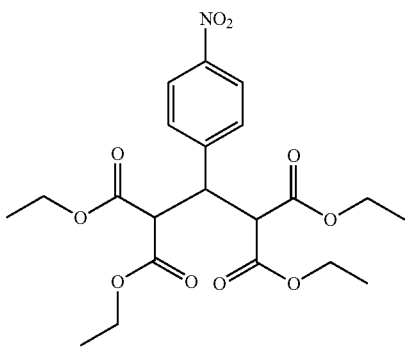 [SMILES: CCOC(=O)C(C(=O)OCC)C(c1ccc([N+](=O)[O-])cc1)C(C(=O)OCC)C(=O)OCC]

A solution of 1.42 g (20.8 mmol) of solid NaOEt in EtOH (30 mL) was treated with 3.43 mL (22.6 mmol) of malonic acid diethyl ester at RT for 20 min. This mixture was treated with a solution of 5.09 g (17.4 mmol) of 2-(4-nitro-benzylidine)-malonic acid diethyl ester (as prepared in the previous step) at RT for 6 h. AcOH (5 mL) was added, and the mixture stirred for 5 min. The mixture was partitioned between water (50 mL) and CH$_2$Cl$_2$ (125 mL). The organic layer was separated, dried (MgSO$_4$), and concentrated in vacuo to afford 7.32 g (93%) of the title compound: $^1$H-NMR (CDCl$_3$; 400

MHz): δ 8.12 (d, 2H, J=8.8 Hz), 7.58 (d, 2H, J=8.8 Hz), 5.30 (s, 1H), 4.34-4.28 (m, 1H), 4.26-4.11 (m, 9H), 1.32-1.20 (m, 12H).

g) 3-(4-Nitro-phenyl)-pentanedioic acid

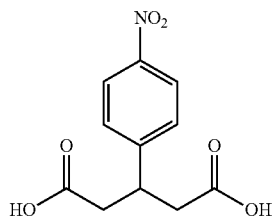

A suspension of 7.32 g (16.1 mmol) of 2,4-bis-ethoxycarbonyl-3-(4-nitro-phenyl)-pentanedioic acid diethyl ester (as prepared in the previous step) in concentrated HCl (15 mL) was heated to 100° C. for 22 h. The mixture was cooled to RT, and the resulting precipitate was filtered, washed with cold water, and air-dried to afford 3.58 g (88%) of the title compound as an off-white solid: $^1$H-NMR (CD$_3$OD; 400 MHz): δ 8.12 (d, 2H, J=8.8 Hz), 7.58 (d, 2H, J=8.8 Hz), 3.77-3.68 (m, 1H), 2.87-2.66 (m, 4H).

h) 4-(4-Nitro-phenyl)-piperidine-2,6-dione

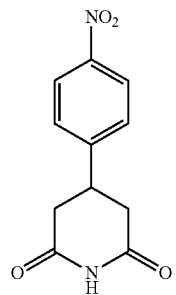

A mixture of 250 mg (0.987 mmol) of 3-(4-nitro-phenyl)-pentanedioic acid (as prepared in the previous step) and 119 mg (1.98 mmol) of urea was heated to 150° C. for 40 min (until all solid melted and gas evolution stopped). The mixture was cooled to RT, taken up in EtOAc (70 mL), washed with saturated aqueous NaHCO$_3$ (2×40 mL), dried (MgSO$_4$), and concentrated in vacuo to afford 52.0 mg (22%) of the title compound as a brown solid: $^1$H-NMR (CDCl$_3$; 400 MHz): δ 8.28 (d, 2H, J=8.8 Hz), 7.44 (d, 2H, J=8.8 Hz), 3.64-3.54 (m, 1H), 3.04-2.96 (m, 2H), 2.86-2.76 (m, 2H).

Alternatively, the title compound can be obtained in the following manner: A solution of 500 mg (1.97 mmol) of 3-(4-nitro-phenyl)-pentanedioic acid (as prepared in the previous step) in 50 mL dioxane was cooled to 10° C. and treated with 229 µL (2.96 mmol) of methyl chloroformate and 936 µL (6.71 mmol) of triethylamine for 7.2 h. A solution of 0.5 M ammonia in dioxane (15.8 mL, 7.90 mmol) was added at 10° C. and the mixture stirred at RT for 72 h. The mixture was filtered through Celite, the filter cake washed with EtOAc, and the solvents evaporated in vacuo. The residue was treated with solid 1.30 g (15.8 mmol) of NaOAc and acetic anhydride (4 mL) and heated to 100° C. for 1 h. The mixture was cooled to RT and concentrated to half the original volume. The residue was taken up in EtOAc (100 mL), washed with saturated aqueous NaHCO$_3$ (1×75 mL), brine (1×75 mL), and water (1×75 mL). The organic layer was dried (MgSO$_4$) and concentrated in vacuo. Silica gel chromatography of the residue on a 50-g Varian MegaBond Elut SPE column with 50-60% EtOAc-hexane afforded 197 mg (43%) of the title compound as an off-white solid (see spectrum above).

i) 4-(4-Amino-phenyl)-piperidine-2,6-dione

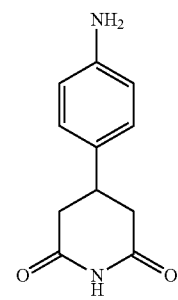

A solution of 197 mg (0.841 mmol) of 4-(4-nitro-phenyl)-piperidine-2,6-dione (as prepared in the previous step) in methyl alcohol (MeOH) (15 mL) was hydrogenated over 10% Pd/C at 20 psi for 5 h at RT. The mixture was filtered through Celite, the filter cake was washed with MeOH, and the solvents were evaporated in vacuo to afford 106 mg (62%) of the title compound as an off-white solid: Mass spectrum (ESI, m/z): Calcd. for C$_{11}$H$_{12}$N$_2$O$_2$, 205.1 (M+H). found 205.1.

j) 4-(4-Amino-3-bromo-phenyl)-piperidine-2,6-dione

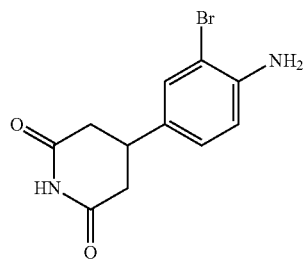 [SMILES: Nc1ccc(C2CC(=O)NC(=O)C2)cc1Br]

A solution of 106 mg (0.519 mmol) of 4-(4-amino-phenyl)-piperidine-2,6-dione (as prepared in the previous step) in CH$_2$Cl$_2$ (20 mL) was cooled to 0° C. and treated with 92.4 mg (0.519 mmol) of NBS for 35 min. The mixture was diluted with CH$_2$Cl$_2$ (50 mL) and washed with saturated aqueous NaHCO$_3$ (2×40 mL) and water (1×40 mL). The organic layer was dried (MgSO$_4$) and concentrated in vacuo to afford 138 mg (94%) of the title compound as a tan solid: Mass spectrum (ESI, m/z): Calcd. for $C_{11}H_{11}N_2O_2Br$, 283.0/285.0 (M+H). found 283.1/285.1.

k) 4-(4-Amino-3-cyclohex-1-enyl-phenyl)-piperidine-2,6-dione

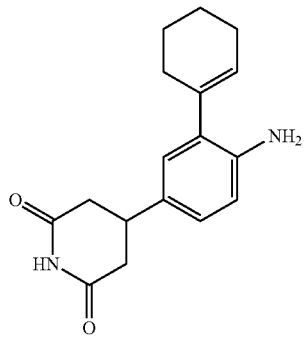 [SMILES: Nc1ccc(C2CC(=O)NC(=O)C2)cc1C1=CCCCC1]

A solution of 69.0 mg (0.244 mmol) of 4-(4-amino-3-bromo-phenyl)-piperidine-2,6-dione (as prepared in the previous step) in toluene (10 mL) and dioxane (10 mL) was treated with 30.7 mg (0.244 mmol) of cyclohex-1-enylboronic acid, 104 mg (0.487 mmol) of $K_3PO_4$, and 34.2 mg (0.0975 mmol) of 2-(dicyclohexylphosphino)biphenyl. The mixture was degassed via sonication, placed under Ar, treated with 5.50 mg (0.0244 mmol) of $Pd(OAc)_2$, and heated to 90° C. for 5 h. The mixture was diluted with EtOAc (30 mL) and washed with water (2×20 mL). The organic layer was dried ($MgSO_4$) and concentrated in vacuo to afford 73.5 mg (106%, some solvent trapped) of the title compound as a tan solid: Mass spectrum (ESI, m/z): Calcd. for $C_{17}H_{20}N_2O_2$, 285.2 (M+H). found 285.2.

l) 4-Cyano-1-(2-trimethylsilanyl-ethoxymethyl)-1H-imidazole-2-carboxylic acid [2-cyclohex-1-enyl-4-(2,6-dioxo-piperidin-4-yl)-phenyl]-amide

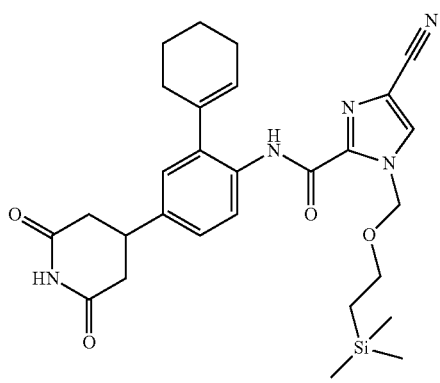 [SMILES: C[Si](C)(C)CCOCn1cc(C#N)nc1C(=O)Nc1ccc(C2CC(=O)NC(=O)C2)cc1C1=CCCCC1]

A solution of 73.5 mg (0.259 mmol) of 4-(4-amino-3-cyclohex-1-enyl-phenyl)-piperidine-2,6-dione (as prepared in the previous step) in $CH_2Cl_2$ (20 mL) was treated with 64.4 mg (0.388 mmol) of PyBroP, 86.8 mg (0.284 mmol) of 4-cyano-1-(2-trimethylsilanyl-ethoxymethyl)-1H-imidazole-2-carboxylate potassium salt (as prepared in this Example, step (d)), and 135 μL (0.775 mmol) of DIEA at RT for 2 h. The mixture was diluted with $CH_2Cl_2$ (50 mL) and washed with saturated aqueous $NaHCO_3$ (2×30 mL). The organic layer was dried ($MgSO_4$) and concentrated in vacuo to afford 70.0 mg (51%) of the title compound as an off-white solid: Mass spectrum (ESI, m/z): Calcd. for $C_{28}H_{35}N_5O_4Si$, 534.3 (M+H). found 534.2.

m) 4-Cyano-1H-imidazole-2-carboxylic acid [2-cyclohex-1-enyl-4-(2,6-dioxo-piperidin-4-yl)-phenyl]-amide A solution of 70.0 mg (0.131 mmol) of 4-cyano-1-(2-trimethylsilanyl-ethoxymethyl)-1H-imidazole-2-carboxylic acid [2-cyclohex-1-enyl-4-(2,6-dioxo-piperidin-4-yl)-phenyl]-amide (as prepared in the previous step) in $CH_2Cl_2$ (10 mL) was treated with EtOH (2 drops) and TFA (3 mL) at RT for 1.5 h. Solvents were removed in vacuo. Purification of the residue by reverse phase high pressure liquid chromatography (RP-HPLC) (C18) with 10-80% $CH_3CN$ in 0.1% TFA/$H_2O$ over 30 min afforded 5.3 mg (8%) of the title compound as a white solid: $^1H$-NMR ($CD_3OD$; 400 MHz): δ 8.18 (d, 1H, J=8.4 Hz), 8.01 (s, 1H), 7.24 (dd, 1H, J=8.4, 2.4 Hz), 7.15 (d, 1H, J=2.4 Hz), 5.85-5.78 (m, 1H), 3.48-3.38 (m, 1H), 2.90-2.71 (m, 4H), 2.32-2.22 (m, 4H), 1.90-1.73 (m, 4H). Mass spectrum (ESI, m/z): Calcd. for $C_{22}H_{21}N_5O_3$, 404.2 (M+H). found 404.0.

Example 2

Another method for the preparation of 4-Cyano-1H-imidazole-2-carboxylic acid [2-cyclohex-1-enyl-4-(2,6-dioxo-piperidin-4-yl)-phenyl]-amide from Example 1

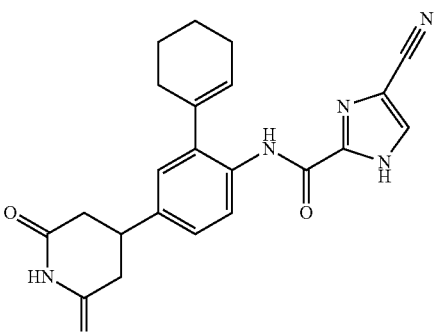

a) 3-(4-Nitro-phenyl)-pentanedioic acid

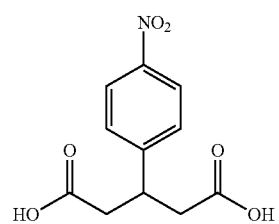 [SMILES: O=C(O)CC(CC(=O)O)c1ccc([N+](=O)[O-])cc1]

A flask charged with concentrated $H_2SO_4$ (400 mL) was cooled to 0° C. and treated with 50.0 g (240 mmol) of 3-phenyl-pentanedioic acid portionwise over 20 min and with fuming HNO₃ (10 mL) dropwise over 20 min. The mixture was stirred at RT for 3 h, poured over ice (amount equivalent to 1000 mL), and the precipitate was filtered, washed with cold water, air-dried, and dried in a vacuum dessicator. The solid was triturated with a minimum amount of CH₃CN, filtered, and air-dried. The filtrate was concentrated and triturated again with a minimum amount of CH₃CN, filtered, and air-dried to afford a second batch. The two batches were combined to afford 56.9 g (94%) of the title compound as an off-white solid: $^1$H-NMR (DMSO-$d_6$; 400 MHz): δ 8.15 (d, 2H, J=8.8 Hz), 7.58 (d, 2H, J=8.8 Hz), 3.62-3.50 (m, 1H), 2.79-2.57 (m, 4H).

b) 4-(4-Nitro-phenyl)-dihydro-pyran-2,6-dione

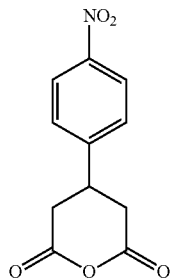

A flask was charged with 20.0 g (79.0 mmol) of 3-(4-nitro-phenyl)-pentanedioic acid (as prepared in the previous step) and 22.4 mL (237 mmol) of acetic anhydride. The mixture was heated to 80° C. for 1 h, cooled to RT, and treated slowly with ether until the product began to precipitate. After allowing the solid to fully precipitate, the solid was filtered, washed with ether, and air-dried to afford 13.0 g (70%) of the title compound as an off-white solid: $^1$H-NMR (CDCl₃; 400 MHz): δ 8.28 (d, 2H, J=8.8 Hz), 7.41 (d, 2H, J=8.8 Hz), 3.64-3.53 (m, 1H), 3.22-3.13 (m, 2H), 2.96-2.85 (m, 2H).

c) 1-(4-Methoxy-benzyl)-4-(4-nitro-phenyl)-piperidine-2,6-dione

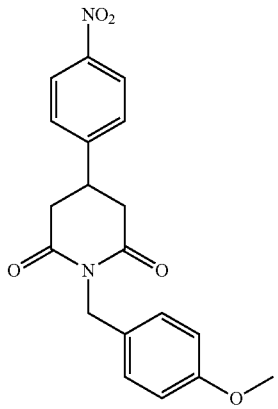 [SMILES: COc1ccc(CN2C(=O)CC(c3ccc([N+](=O)[O-])cc3)CC2=O)cc1]

A solution of 12.6 g (53.6 mmol) of 4-(4-nitro-phenyl)-dihydro-pyran-2,6-dione (as prepared in the previous step) in THF (160 mL) was treated with 9.04 mL (6.96 mmol) of 4-methoxy-benzylamine at RT for 2 h. Solvents were evaporated in vacuo. The residue was dissolved in 1.0 N HCl (200 mL) and extracted with EtOAc (2×250 mL). The combined organic layers were washed with water (1×200 mL), dried (MgSO₄) and concentrated in vacuo. The residue was treated with acetic anhydride (200 mL) and triethylamine (30 mL), and heated to 85° C. for 1.5 h. The mixture was concentrated in vacuo, treated with 1.0 N HCl (200 mL), and extracted with EtOAc (3×200 mL). The combined organic layers were washed with saturated aqueous NaHCO₃ (1×200 mL) and water (1×200 mL), dried (MgSO₄), and concentrated in vacuo. The solid was triturated with hexane using sonication, filtered and air-dried to afford 16.5 g (87%) of the title compound as light tan solid: Mass spectrum (ESI, m/z): Calcd. for $C_{19}H_{21}N_2O$, 325.1 (M-OCH₃+2H). found 325.0.

d) 4-(4-Nitro-phenyl)-piperidine-2,6-dione

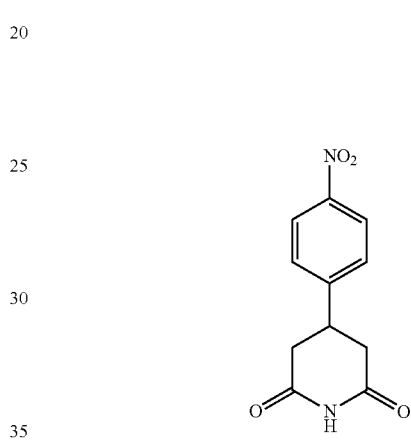

A suspension of 22.8 g (64.2 mmol) of 1-(4-methoxy-benzyl)-4-(4-nitro-phenyl)-piperidine-2,6-dione (as prepared in the previous step) in CH₃CN (150 mL) was treated with 70.4 g (128 mmol) of ceric ammonium nitrate (CAN) as a solution in water (100 mL). The mixture was stirred at RT for 5 h, diluted with water (100 mL), and extracted with EtOAc (2×150 mL). The combined organic layers were washed with saturated aqueous NaHCO₃ (1×100 mL) and water (1×100 mL). The combined aqueous layers were extracted with EtOAc (1×100 mL). The combined organic layers were dried (MgSO₄) and concentrated in vacuo. The solid residue was triturated with a minimum amount of CH₃CN, filtered, and air-dried. The filtrate was concentrated and triturated again with a minimum amount of CH₃CN, filtered, and air-dried as a second batch. The two batches were combined to afford 7.00 g (47%) as an off-white solid: $^1$H-NMR (CDCl₃; 400 MHz): δ 8.26 (d, 2H, J=8.8 Hz), 7.97 (br s, 1H), 7.42 (d, 2H, J=8.8 Hz), 3.62-3.52 (m, 1H), 3.02-2.93 (m, 2H), 2.84-2.74 (m, 2H).

e) 4-Cyano-1H-imidazole-2-carboxylic acid [2-cyclohex-1-enyl-4-(2,6-dioxo-piperidin-4-yl)-phenyl]-amide The title compound was prepared from 4-(4-nitro-phenyl)-piperidine-2,6-dione (as prepared in the previous step) using

Example 3

4-Cyano-1H-imidazole-2-carboxylic acid [2-(4,4-dimethyl-cyclohex-1-enyl)-4-(2,6-dioxo-piperidin-4-yl)-phenyl]-amide

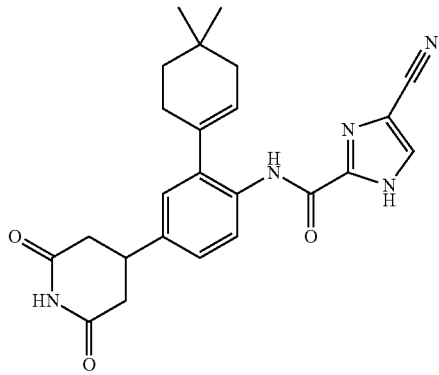 [SMILES: CC1(C)CC=C(c2cc(C3CC(=O)NC(=O)C3)ccc2NC(=O)c2nc(C#N)c[nH]2)CC1]

a) 4-[4-Amino-3-(4,4-dimethyl-cyclohex-1-enyl)-phenyl]-piperidine-2,6-dione

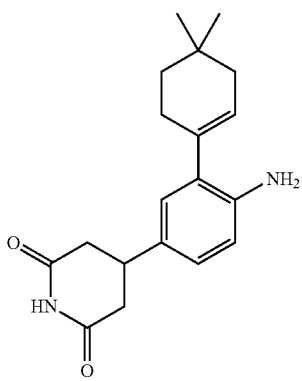 [SMILES: CC1(C)CC=C(c2cc(C3CC(=O)NC(=O)C3)ccc2N)CC1]

A solution of 600 mg (2.12 mmol) of 4-(4-amino-3-bromo-phenyl)-piperidine-2,6-dione (as prepared in Example 1, step (j)) in toluene (20 mL) and dioxane (20 mL) was treated with 900 mg (4.24 mmol) of $K_3PO_4$, 424 mg (2.76 mmol) of 4,4-dimethyl-cyclohex-1-enylboronic acid, and 297 mg (0.848 mmol) of 2-(dicyclohexylphosphino)biphenyl. The mixture was degassed via sonication, placed under Ar, treated with 47.6 mg (0.212 mmol) of $Pd(OAc)_2$, and heated to 80° C. for 2.5 h. The mixture was diluted with EtOAc (100 mL) and washed with water (2×70 mL). The aqueous layer was extracted with EtOAc (100 mL), the combined organic layers were dried ($MgSO_4$) and concentrated in vacuo. Silica gel chromatography of the residue on a 50-g Varian MegaBond Elut SPE column with 25-50% EtOAc-hexane afforded 140 mg (21%) of the title compound as a tan solid: Mass spectrum (ESI, m/z): Calcd. for $C_{19}H_{24}N_2O_2$, 313.2 (M+H). found 313.1.

b) 4-Cyano-1-(2-trimethylsilanyl-ethoxymethyl)-1H-imidazole-2-carboxylic acid [2-(4,4-dimethyl-cyclohex-1-enyl)-4-(2,6-dioxo-piperidin-4-yl)-phenyl]-amide

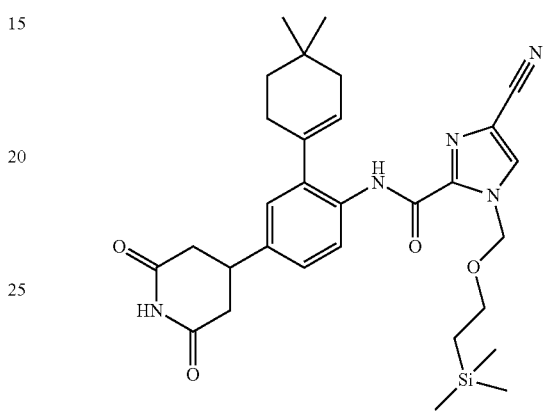

A solution of 140 mg (0.448 mmol) of 4-[4-amino-3-(4,4-dimethyl-cyclhex-1-enyl)-phenyl]-piperidine-2,6-dione (as prepared in the previous step) in $CH_2Cl_2$ (10 mL) was treated with 313 mg (0.672 mmol) of PyBroP, 151 mg (0.493 mmol) of 4-cyano-1-(2-trimethylsilanyl-ethoxymethyl)-1H-imidazole-2-carboxylate potassium salt (as prepared in Example 1, step (d)), and 234 μL (1.34 mmol) of DIEA at RT for 30 min. The mixture was diluted with $CH_2Cl_2$ (30 mL) and washed with saturated aqueous $NaHCO_3$ (1×30 mL). The organic layer was dried ($MgSO_4$) and concentrated in vacuo. Silica gel chromatography of the residue with 10-42% EtOAc-hexane afforded 192 mg (76%) of the title compound as an off-white solid: Mass spectrum (ESI, m/z): Calcd. for $C_{30}H_{39}N_5O_4Si$, 562.3 (M+H). found 562.0.

c) 4-Cyano-1H-imidazole-2-carboxylic acid [2-(4,4-dimethyl-cyclohex-1-enyl)-4-(2,6-dioxo-piperidin-4-yl)-phenyl]-amide A solution of 190 mg (0.338 mmol) of 4-cyano-1-(2-trimethylsilanyl-ethoxymethyl)-1H-imidazole-2-carboxylic acid [2-(4,4-dimethyl-cyclohex-1-enyl)-4-(2,6-dioxo-piperidin-4-yl)-phenyl]-amide (as prepared in the previous step) in $CH_2Cl_2$ (10 mL) was treated with MeOH (200 μL) and TFA (3 mL) at RT for 1.5 h. MeOH (30 mL) was added, the mixture was concentrated to half volume, MeOH (15 mL) was added, and the solvents were removed completely in vacuo at <35° C. Silica gel chromatography of the residue with 25-75% EtOAc-hexane afforded 92.9 mg (64%) of the title compound as a white solid: $^1$H-NMR ($CD_3OD$; 400 MHz): δ 8.22 (d, 1H, J=8.4 Hz), 8.02 (s, 1H), 7.26 (dd, 1H, J=8.4, 2.4 Hz), 7.18 (d, 1H, J=2.4 Hz), 5.79-5.75 (m, 1H), 3.52-3.42 (m, 1H), 2.93-2.76 (m, 4H), 2.37-2.30 (m, 2H), 2.12-2.07 (m, 2H), 1.62 (t,

--- the same procedures found in Example 1, steps (i)-(m). Spectra are identical to the spectra of Example 1, step (m).

Example 4

4-Cyano-1H-imidazole-2-carboxylic acid [2-cyclohex-1-enyl-4-(2-oxo-hexahydro-pyrimidin-5-yl)-phenyl]-amide trifluoroacetic acid salt

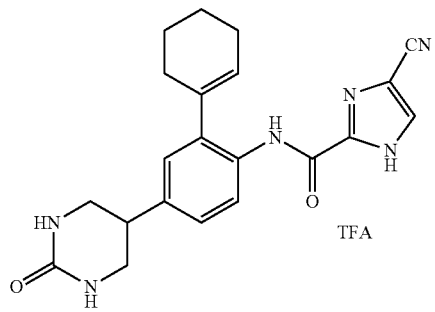 [SMILES: N#Cc1c[nH]c(C(=O)Nc2ccc(C3CNC(=O)NC3)cc2C2=CCCCC2)n1]

a) [4-(2-Hydroxy-1-hydroxymethyl-ethyl)-phenyl]-carbamic acid tert-butyl ester

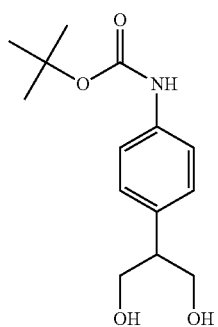 [SMILES: CC(C)(C)OC(=O)Nc1ccc(C(CO)CO)cc1]

A mixture of 2-(4-amino-phenyl)-propane-1,3-diol (1.6 g, 9.6 mmol, *J. Med. Chem.*, 40(25), 4030-4052, (1997)), di-tert-butyl dicarbonate (BOC)$_2$O (2.30 g, 10.5 mmol), THF (200 mL), water (100 mL) and Na$_2$CO$_3$ (1.12 g, 10.5 mmol) was stirred at RT overnight. The reaction mixture was diluted with EtOAc (200 mL) and satd brine (200 mL). The organic layer was separated and the aq layer was extracted with EtOAc (2×100 mL). The organic layers were combined, dried (Na$_2$SO$_4$) and concentrated. The residue obtained was purified on silica (20-100% EtOAc-hexane) to obtain the title compound (1.2 g, 47%): Mass spectrum (ESI, m/z): Calcd. for C$_{14}$H$_{21}$NO$_4$, 290.3 (M+Na). found 290.0.

b) [4-(2-Amino-1-aminomethyl-ethyl)-phenyl]-carbamic acid tert-butyl ester

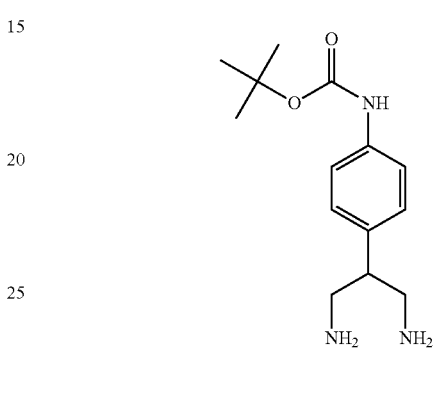

To a suspension of [4-(2-hydroxy-1-hydroxymethyl-ethyl)-phenyl]-carbamic acid tert-butyl ester (267 mg, 1.00 mmol, as prepared in the previous step) in DCM (10 mL) and Et$_3$N (0.35 mL, 2.5 mmol), methanesulfonyl chloride (MsCl) (0.15 mL, 2.0 mmol) was added dropwise at 0° C. The resulting mixture was stirred at RT for 30 min, diluted with DCM (10 mL) and washed with satd NaHCO$_3$ (20 mL). The organic layer was separated, dried (Na$_2$SO$_4$) and concentrated to afford methanesulfonic acid 2-(4-tert-butoxycarbonylamino-phenyl)-3-methanesulfonyloxy-propyl ester, which was dried in vacuo and directly used in next step: Mass spectrum, (ESI, m/z): Calcd. for C$_{16}$H$_{25}$NO$_8$S$_2$, 446.1 (M+Na). found 446.0.

To a solution of crude methanesulfonic acid 2-(4-tert-butoxycarbonylamino-phenyl)-3-methanesulfonyloxy-propyl ester (as prepared above) in DMF (10 mL) was added NaN$_3$ (130 mg, 2.00 mmol). The resulting mixture was heated at 70° C. overnight. The reaction mixture was allowed to cool to RT, diluted with ether (10 mL) and washed with water (3×10 mL). The organic layer was separated, dried (Na$_2$SO$_4$) and concentrated. The residue obtained was purified on silica (10% EtOAc-hexane) to afford [4-(2-azido-1-azidomethyl-ethyl)-phenyl]-carbamic acid tert-butyl ester (206 mg, 65% overall): $^1$H-NMR (CD$_3$OD; 400 MHz): δ 7.33 (d, 2H, J=8.6 Hz), 7.07 (d, 2H, J=8.6 Hz), 3.48 (m, 4H), 2.93 (m, 1H), 1.42 (s, 9H).

[4-(2-Azido-1-azidomethyl-ethyl)-phenyl]-carbamic acid tert-butyl ester (240 mg, 0.757 mmol, as prepared above) was hydrogenated at 40 psi H$_2$ over 10% Pd/C (120 mg) for 1 h. The reaction mixture was filtered through a pad of Celite, concentrated and dried in vacuo to afford [4-(2-amino-1-aminomethyl-ethyl)-phenyl]-carbamic acid tert-butyl ester (169 mg, 64%): $^1$H-NMR (CD$_3$OD; 400 MHz): δ 7.35 (d, 2H, J=8.6 Hz), 7.12 (d, 2H, J=8.6 Hz), 2.90 (m, 2H), 2.79 (m, 2H), 2.69 (m, 1H), 1.42 (s, 9H).

c) [4-(2-Oxo-hexahydro-pyrimidin-5-yl)-phenyl]-carbamic acid tert-butyl ester

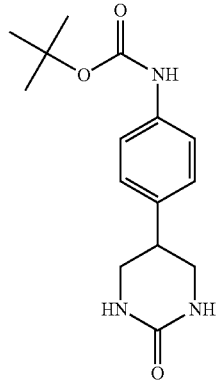 [SMILES: CC(C)(C)OC(=O)Nc1ccc(C2CNC(=O)NC2)cc1]

A solution of [4-(2-amino-1-aminomethyl-ethyl)-phenyl]-carbamic acid tert-butyl ester (as prepared in the previous step, 739 mg, 2.78 mmol) and bis 4-nitrophenylcarbonate (850 mg, 2.79 mmol) in 1,2-dichloroethane (250 mL) was heated at reflux for 24 h. The reaction mixture was concentrated in vacuo and the resulting residue was purified on silica (50% EtOAc-hexane-5% MeOH-EtOAc) to afford the title compound (437 mg, 53%): Mass spectrum (ESI, m/z): Calcd. for C$_{15}$H$_{21}$N$_3$O$_3$, 292.3 (M+H). found 292.0.

d) [2-Bromo-4-(2-oxo-hexahydro-pyrimidin-5-yl)-phenyl]-carbamic acid tert-butyl ester

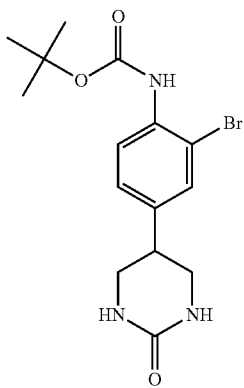 [SMILES: CC(C)(C)OC(=O)Nc1ccc(C2CNC(=O)NC2)cc1Br]

To a solution of [4-(2-oxo-hexahydro-pyrimidin-5-yl)-phenyl]-carbamic acid tert-butyl ester (as prepared in the previous step, 29 mg, 0.10 mmol) in CH$_3$CN (1 mL), NBS (19.5 mg, 0.100 mmol) was added. The resulting mixture was stirred overnight and concentrated to half the volume. The resulting precipitate was collected by filtration to obtain the title compound (12 mg, 32%): Mass spectrum (ESI, m/z): Calcd. for C$_{15}$H$_{20}$BrN$_3$O$_3$, 370.0 and 372.0 (M+H). found 370.1 and 372.1.

e) 5-(4-Amino-3-cyclohex-1-enyl-phenyl)-tetrahydro-pyrimidin-2-one

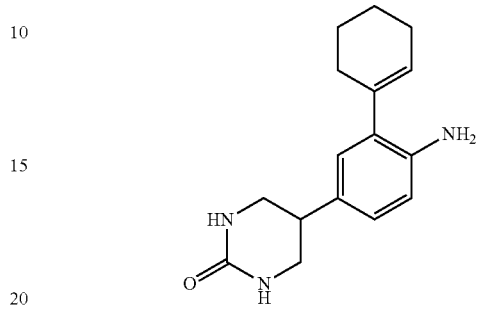

[2-Bromo-4-(2-oxo-hexahydro-pyrimidin-5-yl)-phenyl]-carbamic acid tert-butyl ester (99 mg, 0.26 mmol, as prepared in the previous step) was dissolved in TFA (1 mL). The resulting mixture was stirred at RT for 30 min and concentrated in vacuo. The residue obtained was dried in vacuo for 1 h and dissolved in EtOH (0.5 mL) and toluene (1 mL). To this solution cyclohex-1-enyl boronic acid (20.5 mg, 0.16 mmol), 2M Na$_2$CO$_3$ (0.5 mL, 1 mmol) and Pd (PPh$_3$)$_4$ (30 mg, 0.025 mmol) were added. The resulting mixture was heated at 80° C. overnight. The reaction mixture was allowed to cool to RT and extracted with EtOAc (2×10 mL). The EtOAc layers were combined, dried (Na$_2$SO$_4$) and concentrated in vacuo. The residue obtained was purified on silica (2% MeOH-EtOAc) to afford the title compound (31 mg) contaminated with Ph$_3$PO, which was used in the next step without further purification: Mass spectrum (ESI, m/z): Calcd. for C$_{16}$H$_{21}$N$_3$O, 272.1 (M+H). found 272.1.

f) 4-Cyano-1-(2-trimethylsilanyl-ethoxymethyl)-1H-imidazole-2-carboxylic acid [2-cyclohex-1-enyl-4-(2-oxo-hexahydro-pyrimidin-5-yl)-phenyl]-amide

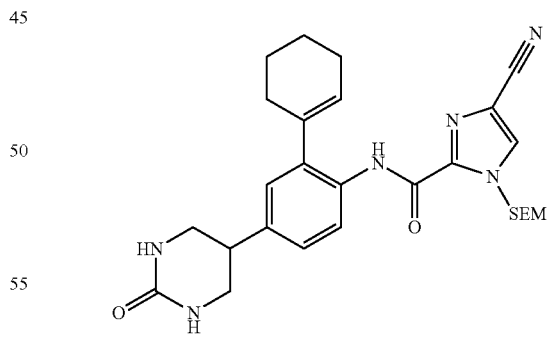

5-(4-Amino-3-cyclohex-1-enyl-phenyl)-tetrahydro-pyrimidin-2-one (22 mg, as prepared in the previous step) was coupled to 4-cyano-1-(2-trimethylsilanyl-ethoxymethyl)-1H-imidazole-2-carboxylic acid, potassium salt (as prepared in Example 1, step (d), 27.2 mg, 0.0890 mmol) as described in Example 1, step (l) to obtain the title compound (14 mg, over two steps) after purification on silica (3% MeOH-EtOAc): Mass spectrum (ESI, m/z): Calcd. for C$_{27}$H$_{36}$N$_6$O$_3$Si, 521.2 (M+H). found 521.1.

g) 4-Cyano-1H-imidazole-2-carboxylic acid [2-cyclohex-1-enyl-4-(2-oxo-hexahydro-pyrimidin-5-yl)-phenyl]-amide trifluoroacetic acid salt 4-Cyano-1-(2-trimethylsilanyl-ethoxymethyl)-1H-imidazole-2-carboxylic acid [2-cyclohex-1-enyl-4-(2-oxo-hexahydro-pyrimidin-5-yl)-phenyl]-amide (as prepared in the previous step, 14 mg, 0.026 mmol) was dissolved in DCM (1 mL), EtOH (30 μL) and TFA (0.3 mL). The resulting mixture was stirred overnight and concentrated. The residue obtained was subjected to RP-HPLC eluting with 20% to 100% CH$_3$CN in 0.1% TFA/H$_2$O over 20 min on a C18 column to obtain the title compound (1.1 mg, 8%): $^1$H-NMR (CD$_3$OD/CDCl$_3$; 400 MHz): δ 8.23 (d, 1H, J=8.0 Hz), 7.90 (s, 1H), 7.20 (dd, 1H, J=8.0, 2.2 Hz), 7.09 (d, 1H, J=2.2 Hz), 5.75 (br s, 1H), 3.47 (4H, m), 3.17 (m, 1H), 2.22-2.33 (m, 4H), 1.72-1.83 (m, 4H). Mass spectrum (ESI, m/z): Calcd. for C$_{21}$H$_{22}$N$_6$O$_2$, 391.3 (M+H). found 391.2.

Example 5

4-Cyano-1H-imidazole-2-carboxylic acid [2-cyclohex-1-enyl-4-(1,1-dioxo-1λ$^6$-[1,2,6]thiadiazinan-4-yl)-phenyl]-amide

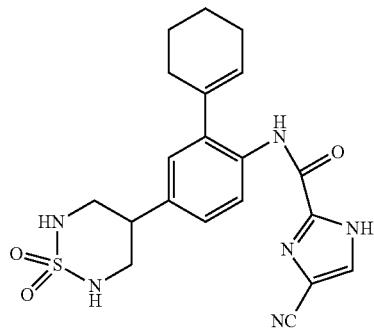 [SMILES: N#Cc1c[nH]c(C(=O)Nc2ccc(C3CNS(=O)(=O)NC3)cc2C2=CCCCC2)n1]

a) [4-(1,1-Dioxo-1λ$^6$-[1,2,6]thiadiazinan-4-yl)-phenyl]-carbamic acid tert-butyl ester

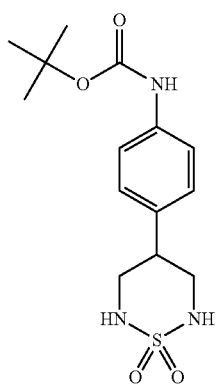 [SMILES: CC(C)(C)OC(=O)Nc1ccc(C2CNS(=O)(=O)NC2)cc1]

[4-(2-Amino-1-aminomethyl-ethyl)-phenyl]-carbamic acid tert-butyl ester (as prepared in Example 4, step (b), 30.4 mg, 0.114 mmol) and sulfamide (15.4 mg, 0.802 mmol) in pyridine (0.7 mL) was heated at reflux for 4 h. The reaction mixture was concentrated in vacuo, and the residue was purified on silica (20%-70% EtOAc-hexane) to obtain the title compound (24 mg, 64%): $^1$H-NMR (DMSO-d$_6$; 400 MHz): δ 9.35 (br s, 1H), 7.45 (m, 2H), 7.15 (m, 2H), 6.73 (m, 2H), 3.52 (m, 2H), 3.27 (m, 2H), 2.85 (m, 1H), 1.52 (s, 9H).

b) 2-Bromo-4-(1,1-dioxo-1λ$^6$-[1,2,6]thiadiazinan-4-yl)-phenylamine

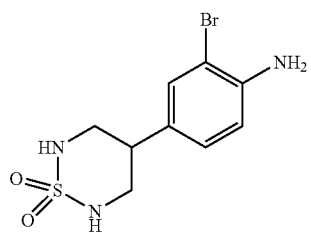 [SMILES: Nc1ccc(C2CNS(=O)(=O)NC2)cc1Br]

[4-(1,1-Dioxo-1λ$^6$-[1,2,6]thiadiazinan-4-yl)-phenyl]-carbamic acid tert-butyl ester (as prepared in the previous step, 100 mg, 0.305 mmol) was dissolved in TFA (1 mL). The resulting solution was stirred at RT for 30 min and concentrated in vacuo. The residue obtained (74.3 mg) was dried in vacuo for 1 h and dissolved in HOAc (2 mL). The resulting mixture was cooled to 0° C. and NBS (42.6 mg, 0.239 mmol) was added. The resulting mixture was stirred for 30 min, washed with aq NaHCO$_3$ (2 mL) and concentrated. The residue was purified on silica (20-100% EtOAc-hexane) to obtain the title compound (49 mg, 52%): $^1$H-NMR (CD$_3$OD; 400 MHz): δ 7.23 (d, 1H, J=2.0 Hz), 6.93 (dd, 1H, J=8.2, 2.0 Hz), 6.78 (d, 1H, J=8.2 Hz), 3.63 (m, 2H), 3.32 (m, 2H), 2.82 (m, 1H).

c) 2-Cyclohex-1-enyl-4-(1,1-dioxo-1λ$^6$-[1,2,6]thiadiazinan-4-yl)-phenylamine

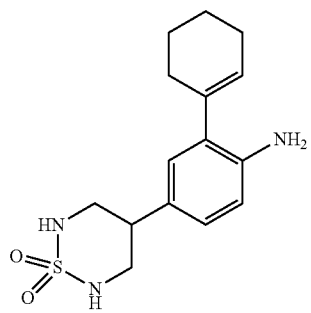 [SMILES: Nc1ccc(C2CNS(=O)(=O)NC2)cc1C1=CCCCC1]

2-Bromo-4-(1,1-dioxo-1λ$^6$-[1,2,6]thiadiazinan-4-yl)-phenylamine (as prepared in the previous step, 46.9 mg, 0.153 mmol) was reacted with cyclohexane-1-enyl boronic acid (24.1 mg, 0.191 mmol) according to the Suzuki coupling procedure of Example 4, step (e) and purified on silica (20-

100% EtOAc-hexane) to afford the title compound (30.7 mg, 65%): Mass spectrum (ESI, m/z): Calcd. for $C_{15}H_{21}N_3O_2S$, 308.1 (M+H). found 308.1.

d) 4-Cyano-1-(2-trimethylsilanyl-ethoxymethyl)-1H-imidazole-2-carboxylic acid [2-cyclohex-1-enyl-4-(1,1-dioxo-1$\lambda^6$-[1,2,6]thiadiazinan-4-yl-phenyl]-amide

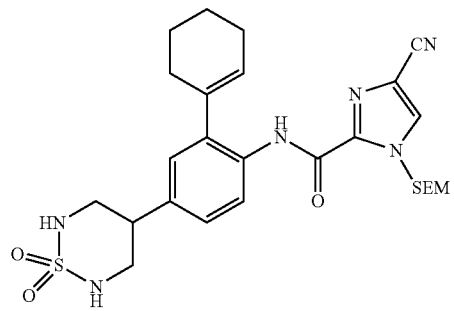 [SMILES: C[Si](C)(C)CCOCn1cc(C#N)nc1C(=O)Nc1ccc(C2CNS(=O)(=O)NC2)cc1C1=CCCCC1]

2-Cyclohex-1-enyl-4-(1,1-dioxo-1$\lambda^6$-[1,2,6]thiadiazinan-4-yl)-phenylamine (as prepared in the previous step, 30.7 mg, 0.100 mmol) was coupled to 4-cyano-1-(2-trimethylsilanyl-ethoxymethyl)-1H-imidazole-2-carboxylic acid, potassium salt (as prepared in Example 1, step (d), 33.6 mg, 0.260 mmol) as described in Example 1, step (l) to obtain the title compound (14 mg, 25%) after purification on silica (20-50% EtOAc-hexane): Mass spectrum (ESI, m/z): Calcd. for $C_{26}H_{36}N_6O_4SSi$, 557.2 (M+H). found 556.8.

e) 4-Cyano-1H-imidazole-2-carboxylic acid [2-cyclohex-1-enyl-4-(1,1-dioxo-1$\lambda^6$-[1,2,6]thiadiazinan-4-yl)-phenyl]-amide To a solution of 4-cyano-1-(2-trimethylsilanyl-ethoxymethyl)-1H-imidazole-2-carboxylic acid [2-cyclohex-1-enyl-4-(1,1-dioxo-1$\lambda^6$-[1,2,6]thiadiazinan-4-yl)-phenyl]-amide (as prepared in the previous step, 17.8 mg, 0.0320 mmol) in DMF (35 μL) and ethylenediamine (13 μL, 0.18 mmol), solid tetrabutylammonium fluoride (TBAF) (25 mg, 0.090 mmol) was added. The resulting solution was stirred at 60° C. for 12 h. The reaction mixture was concentrated in vacuo and the resulting residue purified on silica (20-100% EtOAc-hexane) to afford the title compound (9.3 mg, 68%): $^1$H-NMR (CD$_3$OD; 400 MHz): δ 8.19 (d, 1H, J=8.7 Hz), 8.05 (s, 1H), 7.18 (dd, 1H, J=8.7, 2.2 Hz), 7.08 (d, 1H, J=2.2 Hz), 5.81 (br s, 1H), 3.62 (m, 2H), 3.35 (m, 2H), 2.93 (m, 1H), 2.24-2.34 (m, 4H), 1.82-1.90 (m, 4H). Mass spectrum (ESI, m/z): Calcd. for $C_{20}H_{22}N_6O_3S$, 427.1 (M+H). found 427.2.

Example 6

4-Cyano-1H-imidazole-2-carboxylic acid [2-cyclohex-1-enyl-4-(1,1-dioxo-1$\lambda^6$-[1,2,6]thiadiazinan-4-yl)-5-hydroxymethyl-phenyl]-amide

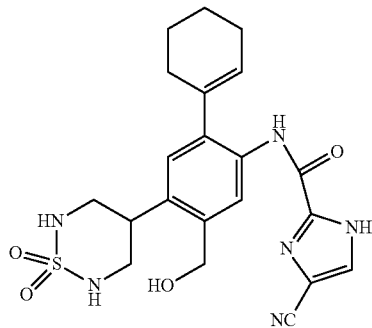 [SMILES: N#Cc1c[nH]c(C(=O)Nc2cc(CO)c(C3CNS(=O)(=O)NC3)cc2C2=CCCCC2)n1]

TFA (0.3 mL) was added to a solution of 4-cyano-1-(2-trimethylsilanyl-ethoxymethyl)-1H-imidazole-2-carboxylic acid [2-cyclohex-1-enyl-4-(1,1-dioxo-1$\lambda^6$-[1,2,6]thiadiazinan-4-yl)-phenyl]-amide (as prepared in Example 5, step (d), 21 mg, 0.030 mmol) in DCM (1 mL) and EtOH (30 μL). The resulting mixture was stirred at RT for 2 h and concentrated in vacuo. The residue obtained was purified on silica (20-50% EtOAc-hexane) to obtain the title compound (8.0 mg, 46%): $^1$H-NMR (CD$_3$OD; 400 MHz): δ 8.10 (s, 1H), 8.05 (s, 1H), 7.11 (s, 1H), 5.78 (br s, 1H), 4.7 (ABq, 1H, J=16 Hz), 4.48 (ABq, 1H, J=16 Hz), 4.3 (m, 1H), 3.87 (m, 1H), 3.52 (m, 1H), 3.6 (m, 1H), 3.18 (m, 1H), 2.62 (br s, 1H), 2.22-2.34 (m, 4H), 1.72-1.90 (m, 4H). Mass spectrum (ESI, m/z): Calcd. for $C_{21}H_{24}N_6O_4S$, 439.1 (M–H$_2$O+H). found 439.2.

Example 7

4-Cyano-1H-imidazole-2-carboxylic acid [2-cyclohex-1-enyl-4-(1,3-dimethyl-2-oxo-hexahydro-pyrimidin-5-yl)-phenyl]-amide trifluoroacetic acid salt

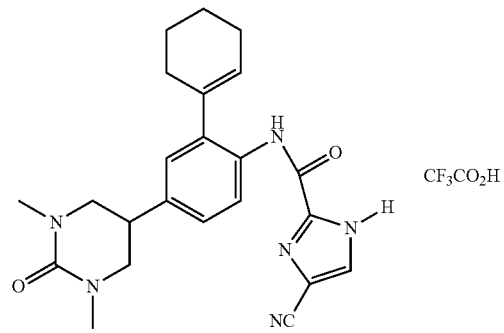 [SMILES: CN1CC(c2ccc(NC(=O)c3nc(C#N)c[nH]3)c(C3=CCCCC3)c2)CN(C)C1=O ; "CF3CO2H"]

a) [4-(1,3-Dimethyl-2-oxo-hexahydro-pyrimidin-5-yl)-phenyl]-carbamic acid tert-butyl ester

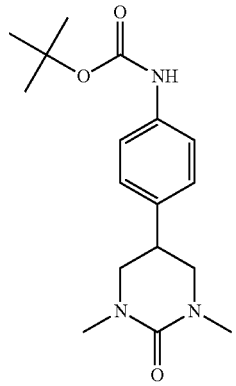 [SMILES: CN1CC(c2ccc(NC(=O)OC(C)(C)C)cc2)CN(C)C1=O]

A mixture of [4-(2-oxo-hexahydro-pyrimidin-5-yl)-phenyl]-carbamic acid tert-butyl ester (as prepared in Example 4, step (c), 376 mg, 1.29 mmol), powdered $K_2CO_3$ (744 mg, 5.39 mmol), $Bu_4NBr$ (41.9 mg, 0.130 mmol), 1,2-dichloroethane (8 mL), and $Me_2SO_4$ (0.5 mL) was heated to 60° C. in sealed tube overnight. The reaction mixture was allowed to cool to RT, and the inorganic solids were filtered off. The filter cake was washed with 1:1 dioxane/DCM (3×20 mL). The organic layers were combined and concentrated in vacuo. The residue obtained was purified on silica (20-100% EtOAc-hexane) to afford the title compound (259 mg, 63%): Mass spectrum (ESI, m/z): Calcd. for $C_{17}H_{25}N_3O_3$, 320.2 (M+H). found 320.0.

b) 5-(4-Amino-3-bromo-phenyl)-1,3-dimethyl-tetrahydro-pyrimidin-2-one trifluoroacetic acid salt

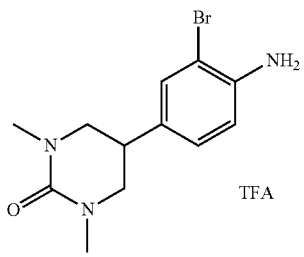 [SMILES: CN1CC(c2ccc(N)c(Br)c2)CN(C)C1=O]

[4-(1,3-Dimethyl-2-oxo-hexahydro-pyrimidin-5-yl)-phenyl]-carbamic acid tert-butyl ester (as prepared in the previous step, 106 mg, 0.333 mmol) was dissolved in TFA (2 mL). The resulting mixture was stirred at RT for 30 min and concentrated. The residue obtained was dried in vacuo for 30 min and redissolved in DCM (5 mL). The resulting solution was cooled to 0° C. and NBS (64 mg, 0.35 mmol) was added. The reaction mixture was stirred at RT for 30 min and treated with DCM (20 mL) and satd aq $NaHCO_3$ (20 mL). The organic layer was separated, dried ($Na_2SO_4$) and concentrated to afford the title compound (92 mg, 92%), which was directly used in next step without further purification. Mass spectrum (ESI, m/z): Calcd. for $C_{12}H_{16}BrN_3O$, 298.0 and 300.0 (M+H). found 298.2 and 300.2.

c) 5-(4-Amino-3-cyclohex-1-enyl-phenyl)-1,3-dimethyl-tetrahydro-pyrimidin-2-one

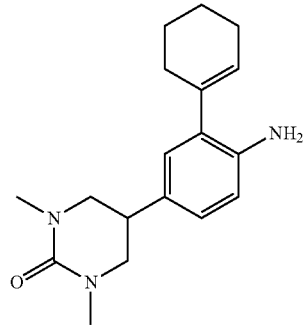 [SMILES: CN1CC(c2ccc(N)c(C3=CCCCC3)c2)CN(C)C1=O]

5-(4-Amino-3-bromo-phenyl)-1,3-dimethyl-tetrahydro-pyrimidin-2-one trifluoroacetic acid salt (as prepared in the previous step, 92 mg, 0.30 mmol) was reacted with cyclohex-1-enyl boronic acid (48.7 mg, 0.375 mmol) according to the Suzuki coupling procedure of Example 4, step (e) and purified on silica (2% MeOH-EtOAc) to afford the title compound (35 mg, 38%): Mass spectrum (ESI, m/z): Calcd. for $C_{18}H_{25}N_3O$, 300.2 (M+H). found 300.3.

d) 4-Cyano-1-(2-trimethylsilanyl-ethoxymethyl)-1H-imidazole-2-carboxylic acid [2-cyclohex-1-enyl-4-(1,3-dimethyl-2-oxo-hexahydro-pyrimidin-5-yl)-phenyl]-amide

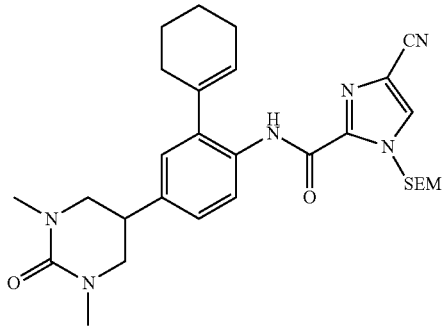 [SMILES: CN1CC(c2ccc(NC(=O)c3nc(C#N)cn3COCC[Si](C)(C)C)c(C3=CCCCC3)c2)CN(C)C1=O]

4-Cyano-1-(2-trimethylsilanyl-ethoxymethyl)-1H-imidazole-2-carboxylic acid [2-cyclohex-1-enyl-4-(1,3-dimethyl-2-oxo-hexahydro-pyrimidin-5-yl)-phenyl]-amide (as prepared in the previous step, 41 mg, 0.13 mmol) was coupled to 4-cyano-1-(2-trimethylsilanyl-ethoxymethyl)-1H-imidazole-2-carboxylic acid, potassium salt (as prepared in Example 1, step (d), 50 mg, 0.16 mmol) as described in Example 1, step (l) to obtain the title compound (66 mg, 87%) after purification on silica (50-100% EtOAc-hexane): Mass spectrum (ESI, m/z): Calcd. for $C_{29}H_{40}N_6O_3Si$, 549.2 (M+H). found 549.2.

e) 4-Cyano-1H-imidazole-2-carboxylic acid [2-cyclohex-1-enyl-4-(1,3-dimethyl-2-oxo-hexahydro-pyrimidin-5-yl)-phenyl]-amide trifluoroacetic acid salt To a solution of 4-cyano-1-(2-trimethylsilanyl-ethoxymethyl)-1H-imidazole-2-carboxylic acid [2-cyclohex-1-enyl- 4-(1,3-dimethyl-2-oxo-hexahydro-pyrimidin-5-yl)-phenyl]-amide (as prepared in the previous step, 66 mg, 0.12 mmol) in DMF (2 mL), solid TBAF (109 mg, 0.410 mmol) was added. The resulting mixture was stirred at 60° C. for 6 h. The DMF was removed in vacuo, and the resulting residue was purified on RP-HPLC eluting with 20% to 100% $CH_3CN$ in 0.1% $TFA/H_2O$ over 20 min on a C18 column to obtain the title compound (26 mg, 52%): $^1$H-NMR ($CDCl_3$; 400 MHz): δ 9.50 (s, 1H), 8.45 (d, 1H, J=8.4 Hz), 7.75 (s, 1H), 7.24 (dd, 1H, J=8.4, 2.0 Hz), 7.08 (d, 1H, J=2.0 Hz), 5.87 (br s, 1H), 3.62 (m, 2H), 3.35 (m, 3H), 2.94 (s, 6H), 2.22-2.34 (m, 4H), 1.72-1.90 (m, 4H). Mass spectrum (ESI, m/z): Calcd. for $C_{23}H_{26}N_6O_2$, 419.2 (M+H). found 419.3.

Example 8

4-Cyano-1H-imidazole-2-carboxylic acid [2-(4,4-dimethyl-cyclohex-1-enyl)-4-(1,3-dimethyl-2-oxo-hexahydro-pyrimidin-5-yl)-phenyl]-amide

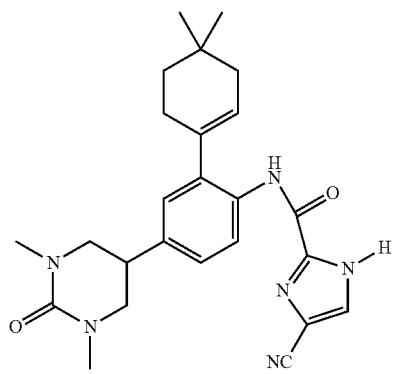 [SMILES: CN1CC(c2ccc(NC(=O)c3nc(C#N)c[nH]3)c(C3=CCC(C)(C)CC3)c2)CN(C)C1=O]

a) 5-[4-Amino-3-(4,4-dimethyl-cyclohex-1-enyl)-phenyl]-1,3-dimethyl-tetrahydro-pyrimidin-2-one

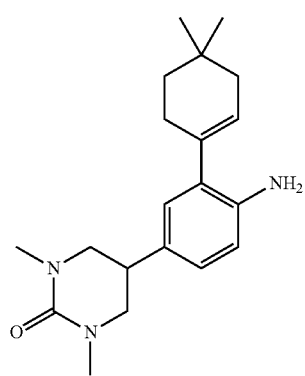 [SMILES: CN1CC(c2ccc(N)c(C3=CCC(C)(C)CC3)c2)CN(C)C1=O]

The title compound was prepared according to the Suzuki coupling procedure of Example 4, step (e), using 4,4-dimethyl-cyclohex-1-enyl boronic acid in place of cyclohex-1-enylboronic acid: Mass spectrum (ESI, m/z): Calcd. for $C_{28}H_{29}N_3O$, 328.2 (M+H). found 328.3.

b) 4-Cyano-1-(2-trimethylsilanyl-ethoxymethyl)-1H-imidazole-2-carboxylic acid [2-(4,4-dimethyl-cyclohex-1-enyl)-4-(1,3-dimethyl-2-oxo-hexahydro-pyrimidin-5-yl)-phenyl]-amide

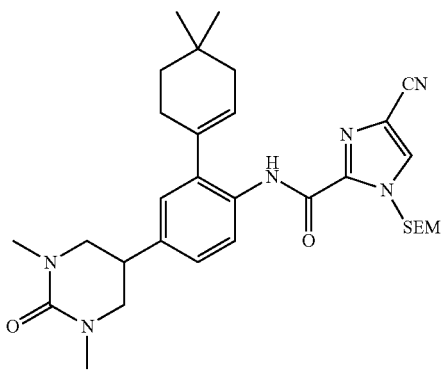 [SMILES: CN1CC(c2ccc(NC(=O)c3nc(C#N)cn3COCC[Si](C)(C)C)c(C3=CCC(C)(C)CC3)c2)CN(C)C1=O]

The title compound was synthesized from 5-[4-amino-3-(4,4-dimethyl-cyclohex-1-enyl)-phenyl]-1,3-dimethyl-tetrahydro-pyrimidin-2-one (as prepared in the previous step) as described in Example 1, step (l): Mass spectrum (ESI, m/z): Calcd. for $C_{31}H_{44}N_6O_3Si$, 577.3 (M+H). found 577.2.

c) 4-Cyano-1H-imidazole-2-carboxylic acid [2-(4,4-dimethyl-cyclohex-1-enyl)-4-(1,3-dimethyl-2-oxo-hexahydro-pyrimidin-5-yl)-phenyl]-amide trifluoroacetic acid salt The title compound was synthesized from 4-cyano-1-(2-trimethylsilanyl-ethoxymethyl)-1H-imidazole-2-carboxylic acid [2-(4,4-dimethyl-cyclohex-1-enyl)-4-(1,3-dimethyl-2-oxo-hexahydro-pyrimidin-5-yl)-phenyl]-amide (as prepared in the previous step) as described in Example 7, step (e). $^1$H-NMR ($CDCl_3$; 400 MHz): δ 9.55 (s, 1H), 8.43 (d, 1H, J=8.4 Hz), 7.73 (s, 1H), 7.24 (dd, 1H, J=8.4, 2.1 Hz), 7.06 (s, 1H), 5.82 (br s, 1H), 3.60 (m, 2H), 3.33 (m, 3H), 3.13 (s, 6H), 2.28-2.35 (m, 2H), 2.08-2.17 (m, 2H), 1.62 (m, 2H), 1.16 (s, 6H); Mass spectrum (ESI, m/z): Calcd. for $C_{25}H_{30}N_6O_2$, 447.2 (M+H). found 447.3.

Example 9

4-Cyano-1H-imidazole-2-carboxylic acid [2-cyclohept-1-enyl-4-(1,3-dimethyl-2-oxo-hexahydro-pyrimidin-5-yl)-phenyl]-amide

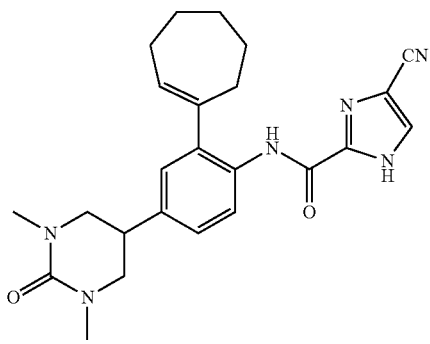 [SMILES: CN1CC(c2ccc(NC(=O)c3nc(C#N)c[nH]3)c(C3=CCCCCC3)c2)CN(C)C1=O]

a) 5-(4-Amino-3-cyclohept-1-enyl-phenyl)-1,3-dimethyl-tetrahydro-pyrimidin-2-one

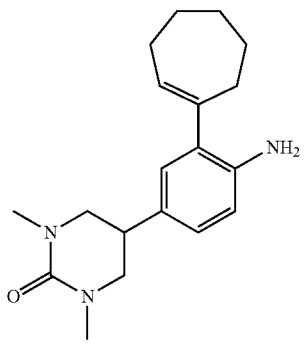 [SMILES: CN1CC(c2ccc(N)c(C3=CCCCCC3)c2)CN(C)C1=O]

A solution of 5-(4-amino-3-bromo-phenyl)-1,3-dimethyl-tetrahydro-pyrimidin-2-one trifluoroacetic acid salt (as prepared in Example 7, step (b), 105 mg, 0.352 mmol), cycloheptene-1-yl boronic acid (74 mg, 0.52 mmol), $K_3PO_4$ (224 mg, 1.05 mmol), tris(dibenzylideneacetone)dipalladium (0) $(Pd_2(dba)_3)$ (32 mg, 0.034 mmol), and 2-dicyclohexylphosphino-2',6'-dimethoxybiphenyl (S-Phos) (57.5 mg, 0.350 mmol) in toluene (0.7 mL) was heated at 100° C. under Ar for 1 h. The reaction mixture was allowed to cool to RT and filtered. The filter cake was washed with DCM (2×10 mL). The organic layers were combined, dried ($Na_2SO_4$) and concentrated in vacuo. The residue obtained was purified on silica (20-100% EtOAc-hexane) to afford the title compound (95 mg, 86%): Mass spectrum (ESI, m/z): Calcd. for $C_{19}H_{27}N_3O$, 314.2 (M+H). found 314.3.

b) 4-Cyano-1-(2-trimethylsilanyl-ethoxymethyl)-1H-imidazole-2-carboxylic acid [2-cyclohept-1-enyl-4-(1,3-dimethyl-2-oxo-hexahydro-pyrimidin-5-yl)-phenyl]-amide

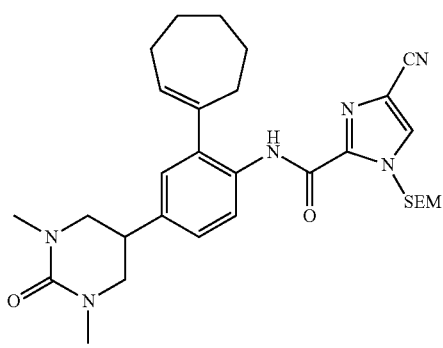 [SMILES: CN1CC(c2ccc(NC(=O)c3nc(C#N)cn3COCC[Si](C)(C)C)c(C3=CCCCCC3)c2)CN(C)C1=O]

5-(4-Amino-3-cyclohept-1-enyl-phenyl)-1,3-dimethyl-tetrahydro-pyrimidin-2-one (as prepared in the previous step, 47.5 mg, 0.151 mmol) was coupled to 4-cyano-1-(2-trimethylsilanyl-ethoxymethyl)-1H-imidazole-2-carboxylic acid, potassium salt (as prepared in Example 1, step (d), 27.2 mg, 0.0890 mmol) as described in Example 1, step (1) to obtain the title compound (82 mg, 96%) after purification on silica (20-100% EtOAc-hexane): Mass spectrum (ESI, m/z): Calcd. for $C_{30}H_{42}N_6O_3Si$, 563.3 (M+H). found 563.1.

c) 4-Cyano-1H-imidazole-2-carboxylic acid [2-cyclohept-1-enyl-4-(1,3-dimethyl-2-oxo-hexahydro-pyrimidin-5-yl)-phenyl]-amide trifluoroacetic acid salt To a solution of 4-cyano-1-(2-trimethylsilanyl-ethoxymethyl)-1H-imidazole-2-carboxylic acid [2-cyclohept-1-enyl-4-(1,3-dimethyl-2-oxo-hexahydro-pyrimidin-5-yl)-phenyl]-amide (as prepared in the previous step, 86 mg, 0.15 mmol) in DMF (2 mL), solid TBAF (213 mg, 0.816 mmol) was added. The resulting mixture was stirred at 60° C. for 6 h. The DMF was removed in vacuo, and the resulting residue was purified on RP-HPLC eluting with 20-100% $CH_3CN$ in 0.1% TFA/$H_2O$ over 20 min on a C18 column to obtain the title compound (39 mg, 47%): $^1H$-NMR ($CD_3OD$; 400 MHz): δ 8.15 (d, 1H, J=8.4 Hz), 8.02 (s, 1H), 7.22 (dd, 1H, J=8.4, 2.1 Hz), 7.13 (d, 1H, J=2.1 Hz), 5.98 (t, 1H, J=6.4 Hz), 3.53-3.38 (m, 5H), 2.96 (m, 6H), 2.54 (m, 2H), 2.42 (m, 2H), 1.92 (m, 2H), 1.65-1.83 (m, 4H). Mass spectrum (ESI, m/z): Calcd. for $C_{24}H_{28}N_6O_2$, 433.2 (M+H). found 433.2.

Example 10

4-Cyano-1H-pyrrole-2-carboxylic acid [2-cyclohept-1-enyl-4-(1,3-dimethyl-2-oxo-hexahydro-pyrimidin-5-yl)-phenyl]-amide

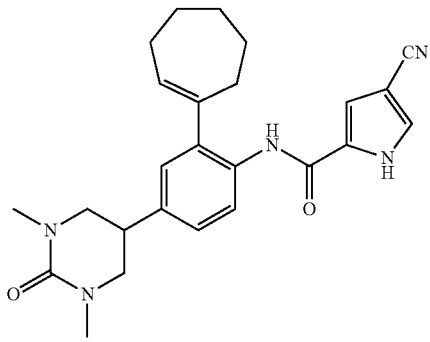 [SMILES: CN1CC(c2ccc(NC(=O)c3cc(C#N)c[nH]3)c(C3=CCCCCC3)c2)CN(C)C1=O]

A mixture of 5-(4-amino-3-cyclohept-1-enyl-phenyl)-1,3-dimethyl-tetrahydro-pyrimidin-2-one (as prepared in Example 9, step (a), 21 mg, 0.067 mmol), 4-cyanopyrrolecarboxylic acid (*Canadian J. Chem.* 59: 2673 (1981)). (24.6 mg, 0.180 mmol), EDCI (19.4 mg, 0.101 mmol), HOBt (9.2 mg, 0.068 mmol), DIEA (35 µL, 0.20 mmol) in DCM (0.5 mL) was stirred at RT overnight. The reaction mixture was concentrated in vacuo and the residue was purified RP-HPLC eluting with 20% to 100% $CH_3CN$ in 0.1% $TFA/H_2O$ over 20 min on a C18 column to obtain the title compound (4.2 mg, 14%): $^1$H-NMR ($CD_3OD$; 400 MHz): δ 7.58 (d, 1H, J=1.5 Hz), 7.44 (d, 1H, J=8.2 Hz), 7.15-7.24 (m, 3H), 5.93 (t, 1H, J=6.5 Hz), 3.38-3.61 (m, 5H), 2.96 (m, 6H), 2.48 (m, 2H), 2.28 (m, 2H), 1.82 (m, 2H), 1.45-1.23 (m, 4H); Mass spectrum (ESI, m/z): Calcd. for $C_{25}H_{29}N_5O_2$, 432.2 (M+H). found 432.2.

Example 11

4-Cyano-1H-imidazole-2-carboxylic acid [2-cyclohex-1-enyl-4-(2,6-dimethyl-1,1-dioxo-1λ$^6$-[1,2,6]thiadiazinan-4-yl)-phenyl]-amide

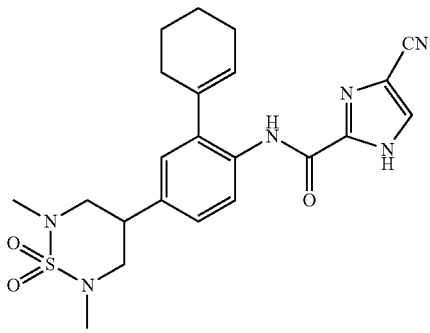 [SMILES: CN1CC(c2ccc(NC(=O)c3nc(C#N)c[nH]3)c(C3=CCCCC3)c2)CN(C)S1(=O)=O]

a) [4-(2,6-Dimethyl-1,1-dioxo-1λ$^6$-[1,2,6]thiadiazinan-4-yl)-phenyl]-carbamic acid tert-butyl ester

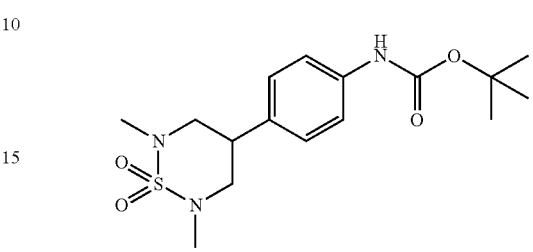

A mixture of [4-(1,1-dioxo-1λ$^6$-[1,2,6]thiadiazinan-4-yl)-phenyl]-carbamic acid tert-butyl ester (as prepared in Example 5, step (a), 327 mg, 1.00 mmol), powdered $K_2CO_3$ (1.88 g, 10.0 mmol) and MeI (0.64 mL, 15 mmol) in DMF (10 mL) was heated at 50° C. for 12 h in a sealed tube. The reaction mixture was allowed to cool to RT, and the inorganic solids were filtered off. The filter cake was washed with 1:1 dioxane/DCM (3×20 mL). The organic layers were combined and concentrated in vacuo. The residue obtained was purified on silica (20-100% EtOAc-hexane) to afford the title compound (233 mg, 65.6%): Mass spectrum (ESI, m/z): Calcd. for $C_{16}H_{25}N_3O_4S$, 356.1 (M+H). found 356.1.

b) [2-Bromo-4-(2,6-dimethyl-1,1-dioxo-1λ$^6$-[1,2,6]thiadiazinan-4-yl)-phenyl]-carbamic acid tert-butyl ester

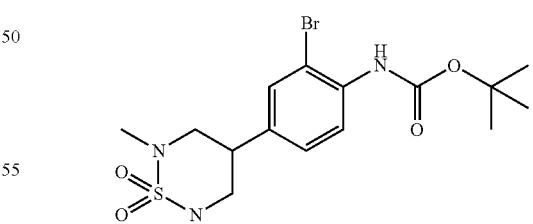

The title compound was prepared from [4-(2,6-dimethyl-1,1-dioxo-1λ$^6$-[1,2,6]thiadiazinan-4-yl)-phenyl]-carbamic acid tert-butyl ester (as prepared in the previous step) according to the procedure described in Example 5, step (b): Mass spectrum (ESI, m/z): Calcd. for $C_{11}H_{16}BrN_3O_2S$, 334.0 and 336.0 (M+H). found 334.0 and 336.0.

c) 2-Cyclohex-1-enyl-4-(2,6-dimethyl-1,1-dioxo-1λ⁶-[1,2,6]thiadiazinan-4-yl)-phenylamine

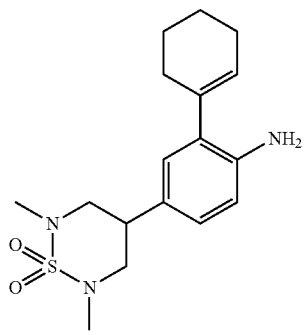 [SMILES: CN1CC(c2ccc(N)c(C3=CCCCC3)c2)CN(C)S1(=O)=O]

The title compound was prepared from [2-bromo-4-(2,6-dimethyl-1,1-dioxo-1λ⁶-[1,2,6]thiadiazinan-4-yl)-phenyl]-carbamic acid tert-butyl ester (as prepared in the previous step) according to the procedure described in Example 4, step (e): Mass spectrum (ESI, m/z): Calcd. for $C_{17}H_{25}N_3O_2S$, 336.1 (M+H). found 336.2.

d) 4-Cyano-1-(2-trimethylsilanyl-ethoxymethyl)-1H-imidazole-2-carboxylic acid [2-cyclohex-1-enyl-4-(2,6-dimethyl-1,1-dioxo-1λ⁶-[1,2,6]thiadiazinan-4-yl)-phenyl]-amide

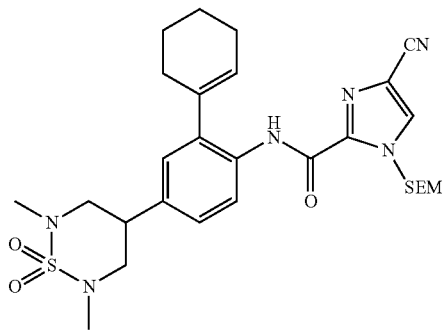 [SMILES: CN1CC(c2ccc(NC(=O)c3nc(C#N)cn3COCC[Si](C)(C)C)c(C3=CCCCC3)c2)CN(C)S1(=O)=O]

The title compound was prepared from 2-cyclohex-1-enyl-4-(2,6-dimethyl-1,1-dioxo-1λ⁶-[1,2,6]thiadiazinan-4-yl)-phenylamine (as prepared in the previous step) according to the procedure described in Example 1, step (l): Mass spectrum (ESI, m/z): Calcd. for $C_{28}H_{40}N_6O_4SSi$, 585.2 (M+H). found 584.9.

e) 4-Cyano-1H-imidazole-2-carboxylic acid [2-cyclohex-1-enyl-4-(2,6-dimethyl-1,1-dioxo-1λ⁶-[1,2,6]thiadiazinan-4-yl)-phenyl]-amide trifluoroacetic acid salt The title compound was prepared from 4-cyano-1-(2-trimethylsilanyl-ethoxymethyl)-1H-imidazole-2-carboxylic acid [2-cyclohex-1-enyl-4-(2,6-dimethyl-1,1-dioxo-1λ⁶-[1,2,6]thiadiazinan-4-yl)-phenyl]-amide (as prepared in the previous step) according to the SEM deprotection procedure described in Example 9, step (b): ¹H-NMR (CDCl₃; 400 MHz): δ 11.85 (br s, 1H), 9.54 (s, 1H,), 8.37 (d, 1H, J=8.4 Hz), 7.73 (d, 1H, J=2.1 Hz), 7.38 (dd, 1H, J=8.4, 2.1 Hz), 7.04 (s, 1H), 5.98 (m, 1H), 3.85 (m, 2H), 3.46 (m, 2H), 3.33 (m, 2H), 2.35-2.20 (m, 4H), 1.65-1.92 (m, 4H): Mass spectrum (ESI, m/z): Calcd. for $C_{22}H_{26}N_6O_2S$, 455.1 (M+H). found 455.2.

Example 12

4-Cyano-1H-imidazole-2-carboxylic acid [4-(2-cyanoimino-hexahydro-pyrimidin-5-yl)-2-cyclohex-1-enyl-phenyl]-amide

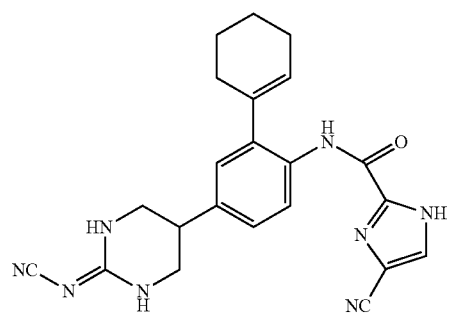 [SMILES: N#CN=C1NCC(c2ccc(NC(=O)c3nc(C#N)c[nH]3)c(C3=CCCCC3)c2)CN1]

a) Acetic acid 3-acetoxy-2-(4-amino-3-cyclohex-1-enyl-phenyl)-propyl ester

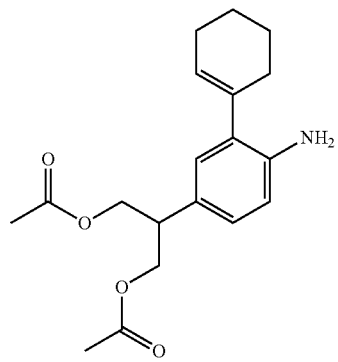 [SMILES: CC(=O)OCC(COC(C)=O)c1ccc(N)c(C2=CCCCC2)c1]

To a solution of acetic acid 3-acetoxy-2-(4-amino-phenyl)-propyl ester (*Tetrahedron*, 46(20), 7081, (1990), 1.2 g, 5.0 mmol) in DCM (50 mL), NBS (903 mg, 5.07 mol) was added at 0° C. The resulting mixture was stirred at RT for 2 h and subjected to the usual work up to obtain acetic acid 3-acetoxy-2-(4-amino-3-bromo-phenyl)-propyl ester (1.4 g, 89%) which was directly used in the next step.

The title compound was prepared according to the Suzuki coupling procedure of Example 9, step (a) using acetic acid 3-acetoxy-2-(4-amino-3-bromo-phenyl)-propyl ester (as prepared above) and cyclohex-1-enyl boronic acid: Mass spectrum, (ESI, m/z): Calcd. for $C_{19}H_{25}NO_4$, 332.1 (M+H). found 332.1.

b) Acetic acid 3-acetoxy-2-(4-{[4-cyano-1-(2-trimethylsilanyl-ethoxymethyl)-1H-imidazole-2-carbonyl]-amino}-3-cyclohex-1-enyl-phenyl)-propyl ester

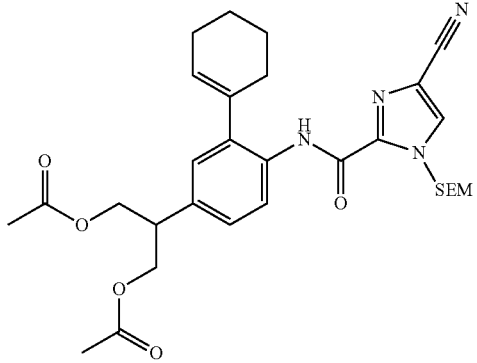 [SMILES: CC(=O)OCC(COC(C)=O)c1ccc(NC(=O)c2nc(C#N)cn2COCC[Si](C)(C)C)c(C2=CCCCC2)c1]

Acetic acid 3-acetoxy-2-(4-amino-3-cyclohex-1-enyl-phenyl)-propyl ester (as prepared in the previous step) was coupled to 4-cyano-1-(2-trimethylsilanyl-ethoxymethyl)-1H-imidazole-2-carboxylic acid, potassium salt (as prepared in Example 1, step (d)) as described in Example 1, step (l) to obtain the title compound: Mass spectrum (ESI, m/z): Calcd. for $C_{30}H_{40}N_4O_6Si$, 581.2 (M+H). found 581.0.

c) 4-Cyano-1-(2-trimethylsilanyl-ethoxymethyl)-1H-imidazole-2-carboxylic acid [2-cyclohex-1-enyl-4-(2-hydroxy-1-hydroxymethyl-ethyl)-phenyl]-amide

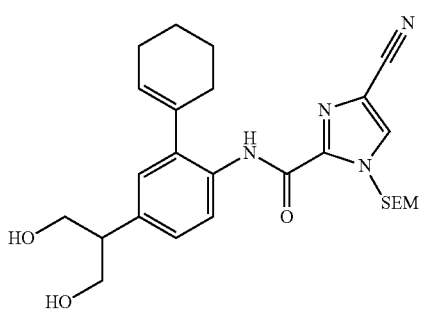 [SMILES: C[Si](C)(C)CCOCn1cc(C#N)nc1C(=O)Nc1ccc(C(CO)CO)cc1C1=CCCCC1]

To a solution of acetic acid 3-acetoxy-2-(4-{[4-cyano-1-(2-trimethylsilanyl-ethoxymethyl)-1H-imidazole-2-carbonyl]-amino}-3-cyclohex-1-enyl-phenyl)-propyl ester (as prepared in the previous step, 580 mg, 1.00 mmol) in i-PrOH (15 mL), 2N NaOH (1 mL, 2 mmol) was added. The reaction mixture was stirred at RT for 1 h, and DCM (200 mL) and water (200 mL) were added. The organic layer was separated, dried ($Na_2SO_4$) and concentrated. The residue was purified on silica (40% EtOAc-hexane) to obtain the title compound (312 mg, 63%): Mass spectrum (ESI, m/z): Calcd. for $C_{26}H_{36}N_4O_4Si$, 497.2 (M+H). found 497.0.

d) 4-Cyano-1-(2-trimethylsilanyl-ethoxymethyl)-1H-imidazole-2-carboxylic acid [4-(2-amino-1-aminomethyl-ethyl)-2-cyclohex-1-enyl-phenyl]-amide

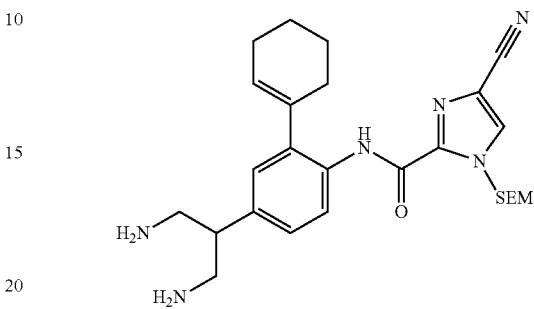

4-Cyano-1-(2-trimethylsilanyl-ethoxymethyl)-1H-imidazole-2-carboxylic acid [2-cyclohex-1-enyl-4-(2-hydroxy-1-hydroxymethyl-ethyl)-phenyl]-amide (as prepared in the previous step) was converted to the corresponding diazide, 4-cyano-1-(2-trimethylsilanyl-ethoxymethyl)-1H-imidazole-2-carboxylic acid [4-(2-azido-1-azidomethyl-ethyl)-2-cyclohex-1-enyl-phenyl]-amide, as previously described in Example 4, step (b), which was directly used in the next step without further purification.

4-Cyano-1-(2-trimethylsilanyl-ethoxymethyl)-1H-imidazole-2-carboxylic acid [4-(2-azido-1-azidomethyl-ethyl)-2-cyclohex-1-enyl-phenyl]-amide (as prepared above, 546 mg, 1.00 mmol) was dissolved in THF (1 mL), water (2 mL) and MeOH (10 mL). To this solution $NH_4Cl$ (534 mg, 25.0 mmol) and Zn powder (653 mg, 10.0 mmol) were added with cooling. The resulting mixture was stirred at RT for 30 min and filtered through a thin pad of Celite. The filter cake was washed with MeOH (2×10 mL). The filtrate was concentrated, dissolved in 5% i-PrOH/DCM and washed with satd aq $NaHCO_3$ (20 mL). The organic layer was dried ($Na_2SO_4$) and concentrated to obtain the title compound (207 mg, 42%): Mass spectrum (ESI, m/z): Calcd. for $C_{26}H_{38}N_6O_2Si$, 495.3 (M+H). found 495.2.

e) 4-Cyano-1-(2-trimethylsilanyl-ethoxymethyl)-1H-imidazole-2-carboxylic acid [4-(2-cyanoimino-hexahydro-pyrimidin-5-yl)-2-cyclohex-1-enyl-phenyl]-amide

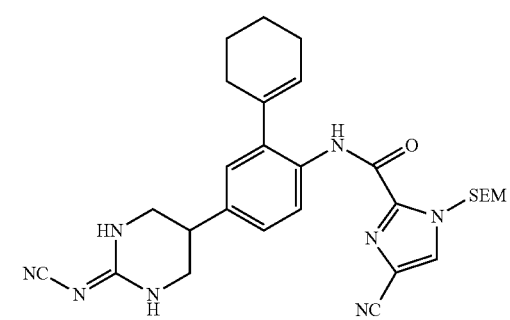 [SMILES: C[Si](C)(C)CCOCn1cc(C#N)nc1C(=O)Nc1ccc(C2CNC(=NC#N)NC2)cc1C1=CCCCC1]

To a solution of 4-cyano-1-(2-trimethylsilanyl-ethoxymethyl)-1H-imidazole-2-carboxylic acid [4-(2-amino-1-aminomethyl-ethyl)-2-cyclohex-1-enyl-phenyl]-amide (as prepared in the previous step, 15 mg, 0.030 mmol) in DCM (10 mL), dimethyl N-cyanodithioiminocarbonate (4.2 mg, 0.28 mmol) was added. The resulting solution was heated at reflux for 4 h. The reaction mixture was allowed to cool to RT and was concentrated in vacuo. The residue obtained was purified on silica (20-100% EtOAc-hexane) to obtain the title compound (11 mg, 62%): Mass spectrum (ESI, m/z): Calcd. for $C_{28}H_{36}N_8O_2Si$, 545.3 (M+H). found 545.1.

f) 4-Cyano-1H-imidazole-2-carboxylic acid [4-(2-cyanoimino-hexahydro-pyrimidin-5-yl)-2-cyclohex-1-enyl-phenyl]-amide 4-Cyano-1-(2-trimethylsilanyl-ethoxymethyl)-1H-imidazole-2-carboxylic acid [4-(2-cyanoimino-hexahydro-pyrimidin-5-yl)-2-cyclohex-1-enyl-phenyl]-amide (as prepared in the previous step) was subjected to SEM deprotection as described in Example 9, step (c) to obtain the title compound: $^1$H-NMR (CD$_3$OD/CDCl$_3$; 400 MHz): δ 8.25 (d, 1H, J=8.4 Hz), 7.73 (s, 1H), 7.24 (dd, 1H, J=8.4, 2.1 Hz), 7.08 (d, 1H, J=2.1 Hz), 5.85 (br s, 1H), 3.4-3.6 (m, 4H), 3.1-3.2 (m, 1H), 2.22-2.34 (m, 4H), 1.77-1.90 (m, 4H): Mass spectrum, (ESI, m/z): Calcd. for $C_{22}H_{27}N_8O_2$, 415.2 (M+H). found 415.2.

Example 13

4-Cyano-1H-imidazole-2-carboxylic acid [2-cyclohex-1-enyl-4(2-methanesulfonylimino-hexahydro-pyrimidin-5-yl)-phenyl]-amide

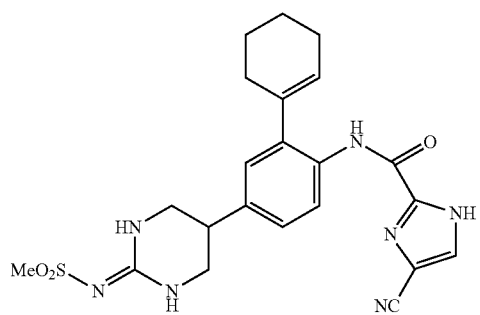 [SMILES: CS(=O)(=O)N=C1NCC(c2ccc(NC(=O)c3nc(C#N)c[nH]3)c(C3=CCCCC3)c2)CN1]

a) 4-Cyano-1-(2-trimethylsilanyl-ethoxymethyl)-1H-imidazole-2-carboxylic acid [2-cyclohex-1-enyl-4-(2-methanesulfonylimino-hexahydro-pyrimidin-5-yl)-phenyl]-amide

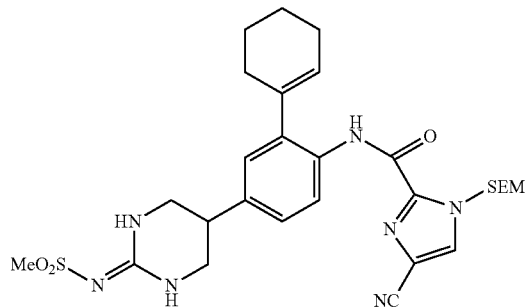 [SMILES: C[Si](C)(C)CCOCn1cc(C#N)nc1C(=O)Nc1ccc(C2CNC(=NS(C)(=O)=O)NC2)cc1C1=CCCCC1]

A solution of 4-cyano-1-(2-trimethylsilanyl-ethoxymethyl)-1H-imidazole-2-carboxylic acid [4-(2-amino-1-aminomethyl-ethyl)-2-cyclohex-1-enyl-phenyl]-amide (as prepared in Example 12, step (d), 250 mg, 0.506 mmol) and N-(bis-methylsulfanyl-methylene)-methanesulfonamide (*Australian Journal of Chemistry*, 46(6), 873, (1993), 100 mg, 0.506 mmol) in 1,2-dichloroethane (20 mL) was heated at reflux for 4 h. The reaction mixture was concentrated, and the residue was purified on silica (20-100% EtOAc-hexane) to obtain the title compound (117 mg, 39%): Mass spectrum, (ESI, m/z): Calcd. for $C_{28}H_{39}N_7O_4SSi$, 598.2 (M+H). found 598.2.

b) 4-Cyano-1H-imidazole-2-carboxylic acid [2-cyclohex-1-enyl 4(2-methanesulfonylimino-hexahydro-pyrimidin-5-yl)-phenyl]-amide 4-Cyano-1-(2-trimethylsilanyl-ethoxymethyl)-1H-imidazole-2-carboxylic acid [2-cyclohex-1-enyl-4-(2-methanesulfonylimino-hexahydro-pyrimidin-5-yl)-phenyl]-amide (as prepared in the previous step) was subjected to SEM deprotection as described in Example 9, step (c) to obtain the title compound: $^1$H-NMR (DMSO-d$_6$; 400 MHz): δ 14.2 (br s, 1H), 9.69 (s, 1H), 8.25 (s, 1H), 7.82 (d, 1H, J=8.4 Hz), 7.44 (s, 1H), 7.17 (dd, 1H, J=8.4, 2.2 Hz), 7.08 (d, 1H, J=2.2 Hz), 5.65 (br s, 1H), 3.32-3.36 (m, 4H), 2.98-3.05 (m, 1H), 2.68 (s, 3H), 2.02-2.18 (m, 4H), 1.45-1.68 (m, 4H): Mass spectrum (ESI, m/z): Calcd. for $C_{22}H_{25}N_7O_3S$, 468.2 (M+H). found 468.3.

Example 14

4-Cyano-1H-imidazole-2-carboxylic acid [2-cyclohex-1-enyl-4-(1-methyl-2,6-dioxo-piperidin-4-yl)-phenyl]-amide

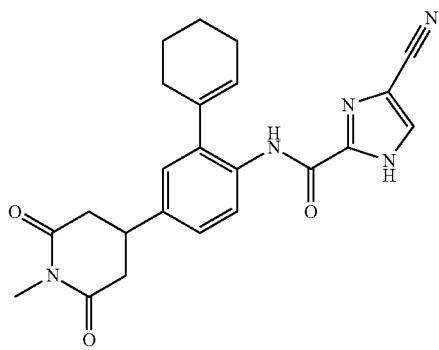 [SMILES: CN1C(=O)CC(c2ccc(NC(=O)c3nc(C#N)c[nH]3)c(C3=CCCCC3)c2)CC1=O]

a) 1-Methyl-4-(4-nitro-phenyl)-piperidine-2,6-dione

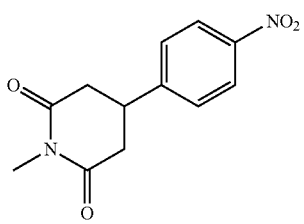 [SMILES: CN1C(=O)CC(c2ccc([N+](=O)[O-])cc2)CC1=O]

A solution of 399 mg (1.70 mmol) of 4-(4-nitro-phenyl)-dihydro-pyran-2,6-dione (as prepared in Example 2, step (b)) in THF (8 mL) was treated with 1.10 mL (2.21 mmol) of 2.0 M methylamine in THF. The mixture was stirred at RT for 45 min, concentrated in vacuo, taken up in 1 N aqueous HCl (10 mL), and extracted with EtOAc (2×20 mL). The combined organic layers were dried (MgSO$_4$) and concentrated in vacuo. The residue was taken up in acetic anhydride (7 mL), treated with triethylamine (1 mL) and heated to 80° C. for 1 h. The solvents were removed in vacuo. The residue was taken up in EtOAc (20 mL) and washed successively with 1 N aqueous HCl, saturated aqueous NaHCO$_3$, and water (1×10 mL each). The organic layer was dried (MgSO$_4$) and concentrated in vacuo. Silica gel chromatography of the residue with 25-50% EtOAc-hexane afforded 348 mg (83%) of the title compound as an off-white solid: $^1$H-NMR (CDCl$_3$; 400 MHz): δ 8.25 (d, 2H, J=8.8 Hz), 7.40 (d, 2H, J=8.8 Hz), 3.56-3.45 (m, 1H), 3.21 (s, 3H), 3.10-3.01 (m, 2H), 2.88-2.77 (m, 2H).

b) 4-(4-Amino-phenyl)-1-methyl-piperidine-2,6-dione

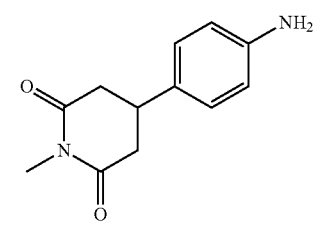 [SMILES: CN1C(=O)CC(c2ccc(N)cc2)CC1=O]

A suspension of 348 mg (1.40 mmol) of 1-methyl-4-(4-nitro-phenyl)-piperidine-2,6-dione (as prepared in the previous step) in MeOH (10 mL) was hydrogenated over 10% Pd/C at 20 psi for 1 h at RT. The mixture was filtered through Celite, the filter cake was washed with MeOH, and the solvents were evaporated in vacuo to afford 289 mg (94%) of the title compound as an off-white solid: Mass spectrum (ESI, m/z): Calcd. for $C_{12}H_{14}N_2O_2$, 219.1 (M+H). found 219.1.

c) 4-(4-Amino-3-bromo-phenyl)-1-methyl-piperidine-2,6-dione

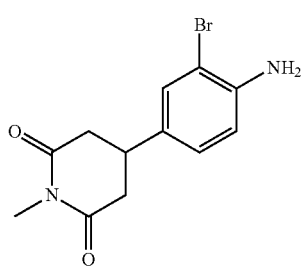 [SMILES: CN1C(=O)CC(c2ccc(N)c(Br)c2)CC1=O]

A solution of 289 mg (1.32 mmol) of 4-(4-amino-phenyl)-1-methyl-piperidine-2,6-dione (as prepared in the previous step) in CH$_2$Cl$_2$ (15 mL) was treated portionwise with 224 mg (1.29 mmol) of solid NBS for 20 min. The mixture was diluted with CH$_2$Cl$_2$ (30 mL) and washed with saturated aqueous NaHCO$_3$ (2×30 mL). The organic layer was dried (MgSO$_4$) and concentrated in vacuo. Silica gel chromatography of the residue with 25-50% EtOAc-hexane afforded 265 mg (67%) of the title compound as a tan solid: Mass spectrum (ESI, m/z): Calcd. for $C_{12}H_{13}N_2O_2Br$, 297.0/299.0 (M+H). found 297.0/299.0.

d) 4-(4-Amino-3-cyclohex-1-enyl-phenyl)-1-methyl-piperidine-2,6-dione

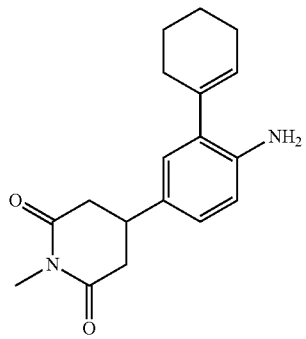 [SMILES: CN1C(=O)CC(c2ccc(N)c(C3=CCCCC3)c2)CC1=O]

A suspension of 265 mg (0.892 mmol) of 4-(4-amino-3-bromo-phenyl)-1-methyl-piperidine-2,6-dione (as prepared in the previous step) in toluene (15 mL) and dioxane (15 mL) was treated with 379 mg (1.78 mmol) of $K_3PO_4$, 146 mg (1.16 mmol) of cyclohex-1-enylboronic acid, and 125 mg (0.357 mmol) of 2-(dicyclohexylphosphino)-biphenyl. The mixture was degassed via sonication, placed under Ar, treated with 20.0 mg (0.00892 mmol) of $Pd(OAc)_2$, and heated to 80° C. for 2.5 h. The mixture was diluted with EtOAc (70 mL) and washed with water (2×50 mL). The combined organic layers were dried ($MgSO_4$) and concentrated in vacuo. Silica gel chromatography of the residue on a 50-g Varian MegaBond Elut SPE column with 25-50% EtOAc-hexane afforded 266 mg (100%) of the title compound as a tan solid: Mass spectrum (ESI, m/z): Calcd. for $C_{18}H_{22}N_2O_2$, 299.2 (M+H). found 299.1.

e) 4-Cyano-1-(2-trimethylsilanyl-ethoxymethyl)-1H-imidazole-2-carboxylic acid [2-cyclohex-1-enyl-4-(1-methyl-2,6-dioxo-piperidin-4-yl)-phenyl]-amide

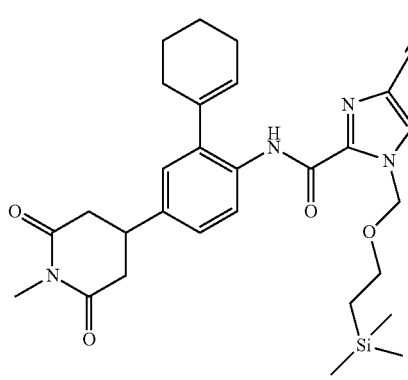

A solution of 266 mg (0.891 mmol) of 4-(4-amino-3-cyclohex-1-enyl-phenyl)-1-methyl-piperidine-2,6-dione (as prepared in the previous step) in $CH_2Cl_2$ (10 mL) was treated with 623 mg (1.34 mmol) of PyBroP, 300 mg (0.981 mmol) of 4-cyano-1-(2-trimethylsilanyl-ethoxymethyl)-1H-imidazole-2-carboxylate potassium salt (as prepared in Example 1, step (d)), and 466 µL (2.67 mmol) of DIEA at RT for 16 h. The mixture was diluted with $CH_2Cl_2$ (30 mL) and washed with saturated aqueous $NaHCO_3$ (1×30 mL). The organic layer was dried ($MgSO_4$) and concentrated in vacuo. Silica gel chromatography of the residue on a 50-g Varian MegaBond Elut SPE column with 25% EtOAc-hexane afforded 130 mg (27%) of the title compound as an off-white solid: Mass spectrum (ESI, m/z): Calcd. for $C_{29}H_{37}N_5O_4Si$, 548.3 (M+H). found 547.9.

f) 4-Cyano-1H-imidazole-2-carboxylic acid [2-cyclohex-1-enyl-4-(1-methyl-2,6-dioxo-piperidin-4-yl)-phenyl]-amide A solution of 130 mg (0.237 mmol) of 4-cyano-1-(2-trimethylsilanyl-ethoxymethyl)-1H-imidazole-2-carboxylic acid [2-cyclohex-1-enyl-4-(1-methyl-2,6-dioxo-piperidin-4-yl)-phenyl]-amide (as prepared in the previous step) in $CH_2Cl_2$ (10 mL) was treated with MeOH (200 µL) and TFA (3 mL) at RT for 1.25 h. MeOH (30 mL) was added, the mixture was concentrated to half volume, MeOH (20 mL) was added, and the solvents were removed completely in vacuo at <35° C. Silica gel chromatography of the residue on a 50-g Varian MegaBond Elut SPE column with 25-50% EtOAc-hexane and by RP-HPLC (C18) with 10-80% $CH_3CN$ in 0.1% TFA/$H_2O$ over 30 min afforded 8.0 mg (8%) of the title compound as a white solid: $^1$H-NMR ($CD_3OD$; 400 MHz): δ 8.19 (d, 1H, J=8.4 Hz), 8.03 (s, 1H), 7.24 (dd, 1H, J=8.4, 2.4 Hz), 7.16 (d, 1H, J=2.4 Hz), 5.87-5.82 (m, 1H), 3.47-3.37 (m, 1H), 3.16 (s, 3H), 2.96-2.91 (m, 4H), 2.33-2.25 (m, 4H), 1.92-1.77 (m, 4H). Mass spectrum (ESI, m/z): Calcd. for $C_{23}H_{23}N_5O_3$, 418.2 (M+H). found 418.1.

Example 15

4-Cyano-1H-imidazole-2-carboxylic acid [2-cyclohex-1-enyl-4-(2-oxo-[1,3]dioxan-5-yl)-phenyl]-amide

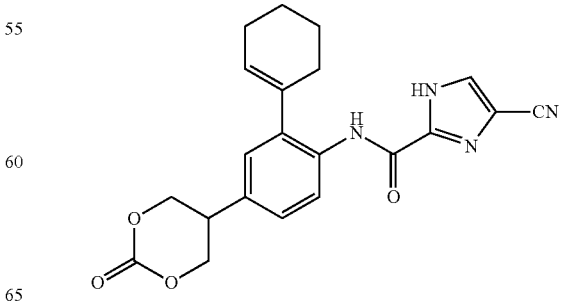

a) 2-(3-Bromo-4-nitro-phenyl)-malonic acid dimethyl ester

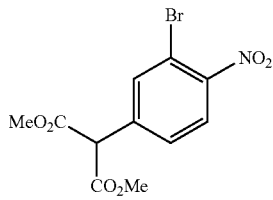 [SMILES: COC(=O)C(C(=O)OC)c1ccc([N+](=O)[O-])c(Br)c1]

To a suspension of NaH (364 mg, 9.08 mmol) in 10 mL of DMF at 0° C. was added malonic acid dimethyl ester (519 μL, 4.54 mmol). The resulting mixture was warmed to RT and stirred for 0.5 h under Ar. 2-Bromo-4-fluoro-1-nitro-benzene (500 mg, 2.27 mmol) was added to the mixture and the reaction was stirred at RT for 16 h under Ar. The mixture was then treated with 2 mL of satd aq $NH_4Cl$ followed by 10 mL of $H_2O$ and extracted with DCM (3×10 mL). The combined extracts were washed with water (10 mL), brine (5 mL) and dried ($Na_2SO_4$). Removal of the solvent in vacuo followed by flash chromatography of the residue on silica gel (1:4 hexane-DCM) gave 604 mg (80%) of a yellow-green oil containing the pure title compound as a mixture of di-ester (A) and its enol tautomer (B): ($CD_3OD$; 400 MHz): A: δ 8.48 (d, 1H, J=2.5 Hz), 8.21 (dd, 1H, J=8.8, 2.5 Hz), 7.85 (d, 1H, J=8.8 Hz), 5.34 (s, 1H), 3.81 (s, 6H). B: δ 7.85 (d, 1H, J=8.4 Hz), 7.82 (d, 1H, J=1.9 Hz), 7.54 (dd, 1H, J=8.4, 1.9 Hz), 4.68 (s, 1H), 3.80 (s, 6H).

b) 2-(3-Cyclohex-1-enyl-4-nitro-phenyl)-malonic acid dimethyl ester

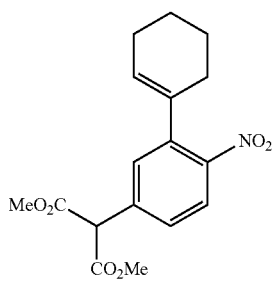 [SMILES: COC(=O)C(C(=O)OC)c1ccc([N+](=O)[O-])c(C2=CCCCC2)c1]

To a mixture of 2-(3-bromo-4-nitro-phenyl)-malonic acid dimethyl ester (as prepared in the previous step, 300 mg, 0.903 mmol), cyclohexane-1-enyl boronic acid (125 mg, 0.994 mmol) and dichloro[1,1'-bis(diphenylphosphino)ferrocene]palladium (II) dichloromethane adduct (Pd(dppf)$Cl_2$—$CH_2Cl_2$) (66.0 mg, 0.0903 mmol) in 5 mL of DMF was added $K_3PO_4$ (765 mg, 3.61 mmol). The resulting mixture was stirred at 60° C. for 9 h under Ar. After cooling to RT, the mixture was treated with 50 mL of EtOAc, washed with $H_2O$ (3×10 mL) and brine (10 mL). The organic layer was dried ($Na_2SO_4$) and concentrated in vacuo. The residue was purified by flash chromatography on silica gel with 10% EtOAc-hexane to afford 210 mg (70%) of the title compound as a yellow oil: Mass spectrum (ESI, m/z): Calcd. for $C_{17}H_{19}NO_6$, 334.1 (M+H). found 334.0.

c) 2-(4-Amino-3-cyclohex-1-enyl-phenyl)-malonic acid dimethyl ester

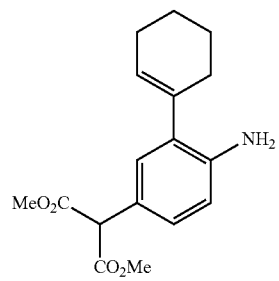

A mixture of 2-(3-cyclohex-1-enyl-4-nitro-phenyl)-malonic acid dimethyl ester (as prepared in the previous step, 200 mg, 0.600 mmol), iron powder (168 mg, 3.00 mmol) and $NH_4Cl$ (321 mg, 6.00 mmol) in 6 mL of ethanol was stirred at 80° C. for 16 h. After cooling to RT, the mixture was treated with 30 mL of $H_2O$ and extracted with EtOAc (3×20 mL). The combined organic layers were dried ($Na_2SO_4$) and concentrated in vacuo. The residue was purified by flash chromatography on silica gel (30% EtOAc-hexane) to give 129 mg (71%) of the title compound as a faint yellow oil: Mass spectrum (ESI, m/z): Calcd. for $C_{17}H_{21}NO_4$, 304.2 (M+H). found 304.1.

d) 2-(4-{[4-Cyano-1-(2-trimethylsilanyl-ethoxymethyl)-1H-imidazole-2-carbonyl]-amino}-3-cyclohex-1-enyl-phenyl)-malonic acid dimethyl ester

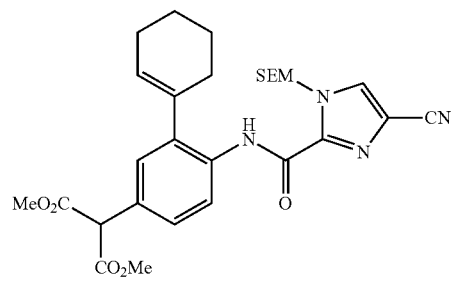 [SMILES: COC(=O)C(C(=O)OC)c1ccc(NC(=O)c2nc(C#N)cn2COCC[Si](C)(C)C)c(C2=CCCCC2)c1]

To a mixture of 2-(4-amino-3-cyclohex-1-enyl-phenyl)-malonic acid dimethyl ester (as prepared in the previous step, 100 mg, 0.330 mmol), potassium 4-cyano-1-(2-trimethylsilanyl-ethoxymethyl)-1H-imidazole-2-carboxylate (as prepared in Example 1, step (d), 106 mg, 0.346 mmol) and bromotripyrrolidinophosphonium hexafluoro-phosphate (PyBroP) (154 mg, 0.330 mmol) in 3 mL of DMF was added N,N-diisopropylethylamine (DIEA) (0.172 mL, 0.990 mmol). After stirring at RT for 16 h, the mixture was treated with 50 mL of EtOAc and washed with $H_2O$ (2×15 mL), brine (15 mL) and dried ($Na_2SO_4$). The organic solvent was evaporated and the residue was purified by flash chromatography on silica gel (5-10% EtOAc-hexane) to give 118 mg (85%) of the title compound as a colorless oil: Mass spectrum (ESI, m/z): Calcd. for $C_{28}H_{36}N_4O_6Si$, 553.2 (M+H). found 552.6.

e) 2-{4-[(4-Cyano-1H-imidazole-2-carbonyl)-amino]-3-cyclohex-1-enyl-phenyl}-malonic acid dimethyl ester

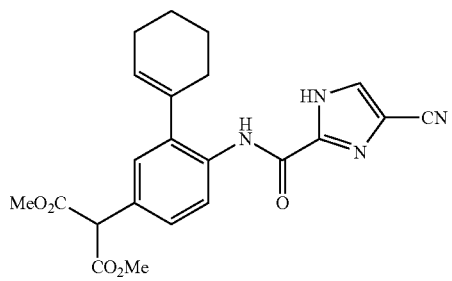 [SMILES: COC(=O)C(C(=O)OC)c1ccc(NC(=O)c2nc(C#N)c[nH]2)c(C2=CCCCC2)c1]

To a solution of 2-(4-{[4-cyano-1-(2-trimethylsilanyl-ethoxymethyl)-1H-imidazole-2-carbonyl]-amino}-3-cyclohex-1-enyl-phenyl)-malonic acid dimethyl ester (as prepared in the previous step, 145 mg, 0.262 mmol) in 1.0 mL of DCM ($CH_2Cl_2$) was added 1.0 mL of TFA. After stirring at RT for 4 h, the mixture was concentrated in vacuo. The residue was purified by flash chromatography on silica gel (20-30% EtOAc-hexane) to give 93 mg (84%) of the title compound as a white solid: Mass spectrum (ESI, m/z): Calcd. for $C_{22}H_{22}N_4O_5$, 423.1 (M+H). found 422.8.

f) 4-Cyano-1H-imidazole-2-carboxylic acid [2-cyclohex-1-enyl-4-(2-hydroxy-1-hydroxymethyl-ethyl)-phenyl]-amide

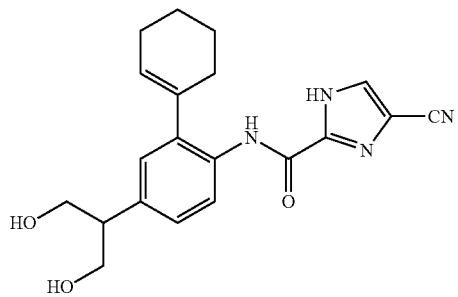 [SMILES: N#Cc1c[nH]c(C(=O)Nc2ccc(C(CO)CO)cc2C2=CCCCC2)n1]

To a mixture of 2-{4-[(4-cyano-1H-imidazole-2-carbonyl)-amino]-3-cyclohex-1-enyl-phenyl}-malonic acid dimethyl ester (as prepared in the previous step, 30.0 mg, 0.0710 mmol) and $NaBH_4$ (13.4 mg, 0.355 mmol) in 1 mL of tert-butyl alcohol (t-BuOH) at 80° C. was added MeOH (50 μL) over 5 min. The resulting mixture was stirred at 80° C. for 16 h under Ar. After cooling to RT, the mixture was treated with 10% aq citric acid to a pH of 7. The mixture was then treated with 30 mL of EtOAc, washed with $H_2O$ (5 mL) and brine (10 mL). The organic layer was dried ($Na_2SO_4$) and concentrated in vacuo. The residue was purified by flash chromatography on silica gel with 1-5% MeOH-DCM to afford 14.1 mg (61%) of the title compound as a white solid: $^1$H-NMR ($CD_3OD$; 400 MHz): δ 8.00 (s, 1H), 7.54 (dd, 1H, J=8.2, 2.3 Hz), 7.46 (d, 1H, J=2.3 Hz), 7.27 (d, 1H, J=8.2 Hz), 5.59 (m, 1H), 3.71-3.84 (m, 4H), 3.29 (m, 1H), 2.15-2.29 (m, 4H), 1.67-1.84 (m, 4H). Mass spectrum (ESI, m/z): Calcd. for $C_{20}H_{22}N_4O_3$, 367.2 (M+H). found 366.8.

g) 4-Cyano-1H-imidazole-2-carboxylic acid [2-cyclohex-1-enyl-4-(2-oxo-[1,3]dioxan-5-yl)-phenyl]-amide To a solution of 4-cyano-1H-imidazole-2-carboxylic acid [2-cyclohex-1-enyl-4-(2-hydroxy-1-hydroxymethyl-ethyl)-phenyl]-amide (as prepared in the previous step, 5.4 mg, 0.015 mmol) and pyridine (3.0 μL, 0.037 mmol) in 0.5 mL of THF at −78° C. was added a solution of triphosgene (1.8 mg, 0.0061 mmol) in 0.5 mL of DCM. The resulting mixture was warmed to RT and continued to stir for 1 h under Ar. Removal of the solvent under reduced pressure followed by flash chromatography of the residue on silica gel (1-2% MeOH-DCM) gave 2.8 mg (48%) of the title compound as a white solid: $^1$H-NMR ($CD_3OD$; 400 MHz): δ 8.01 (s, 1H), 7.66 (dd, 1H, J=8.6, 2.3 Hz), 7.59 (d, 1H, J=2.3 Hz), 7.29 (d, 1H, J=8.6 Hz), 5.66 (m, 1H), 4.65 (dd, 2H, J=10.9, 10.9 Hz), 4.45 (dd, 2H, J=10.9, 4.9 Hz), 3.72 (m, 1H), 2.24 (m, 4H), 1.70-1.88 (m, 4H). Mass spectrum (ESI, m/z): Calcd. for $C_{21}H_{20}N_4O_4$, 393.2 (M+H). found 393.1.

The following examples are produced according to procedures of previous examples with the corresponding reagents as indicated in the table below:

| Example No. | Name | Structure | Procedure Reference | Reagents |
|---|---|---|---|---|
| 16 | 4-Cyano-1H-imidazole-2-carboxylic acid {4-[1,3-bis-(2-hydroxy-ethyl)-2-oxo-hexahydro-pyrimidin-5-yl]-2-cyclohex-1-enyl-phenyl}-amide | 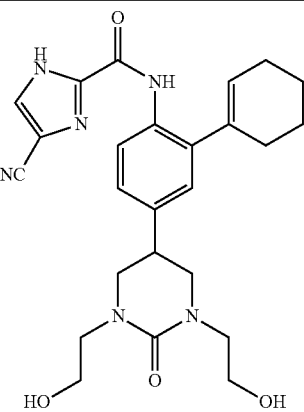 | Ex. 4, steps (a)-(c); Ex 7 | Br(CH$_2$)$_2$OSi-t-BuMe$_2$ (Aldrich Chemical Co.) |
| 17 | 4-Cyano-1H-imidazole-2-carboxylic acid [4-(1,3-diethyl-2-oxo-hexahydro-pyrimidin-5-yl)-2-(4,4-dimethyl-cyclohex-1-enyl)-phenyl]-amide | 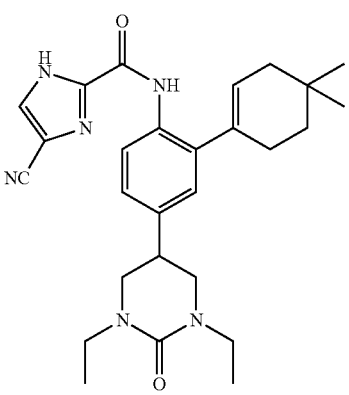 [SMILES: CCN1CC(c2ccc(NC(=O)c3nc(C#N)c[nH]3)c(C3=CCC(C)(C)CC3)c2)CN(CC)C1=O] | Ex. 4, steps (a)-(c); Ex 7 | EtI; 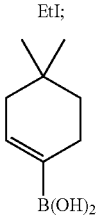 (Combi-Blocks, Inc.) |
| 18 | 4-Cyano-1H-imidazole-2-carboxylic acid [2-(4,4-diethyl-cyclohex-1-enyl)-4-(1,3-dimethyl-2-oxo-hexahydro-pyrimidin-5-yl)-phenyl]-amide | 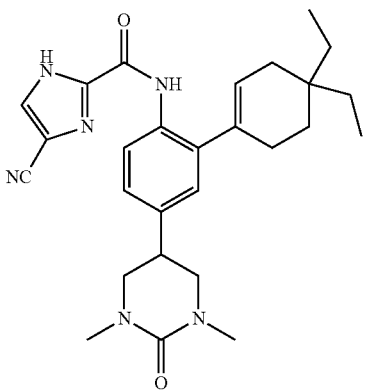 [SMILES: CCC1(CC)CC=C(c2cc(C3CN(C)C(=O)N(C)C3)ccc2NC(=O)c2nc(C#N)c[nH]2)CC1] | Ex. 4, steps (a)-(c); Ex 7 | 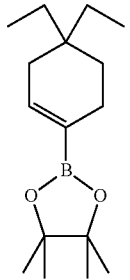 (WO 2005063705) |
| 19 | 4-Cyano-1H-imidazole-2-carboxylic acid [4-(1,1-dioxo-1λ$^6$-[1,2,6]thiadiazinan-4-yl)-2-(4-ethyl-cyclohex-1-enyl)-phenyl]-amide | 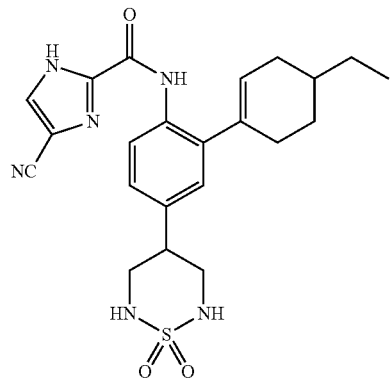 [SMILES: CCC1CC=C(c2cc(C3CNS(=O)(=O)NC3)ccc2NC(=O)c2nc(C#N)c[nH]2)CC1] | Ex. 4, steps (a)-(b); Ex 5 | 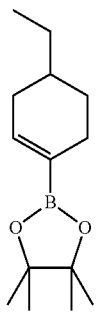 (WO 2005063705) |

| Example No. | Name | Structure | Procedure Reference | Reagents |
|---|---|---|---|---|
| 20 | 4-Cyano-1H-imidazole-2-carboxylic acid [4-(2,6-dimethyl-1,1dioxo-1$\lambda^6$-[1,2,6]thiadiazinan-4-yl)-2-spiro[4.5]dec-7-en-8-yl-phenyl]-amide | 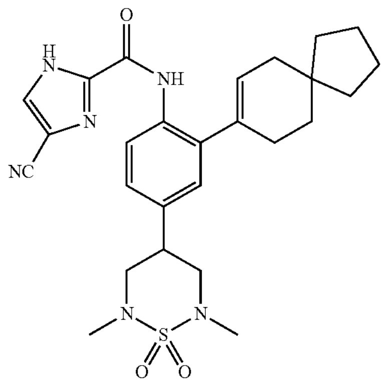 [SMILES: CN1CC(c2ccc(NC(=O)c3nc(C#N)c[nH]3)c(C3=CCC4(CCCC4)CC3)c2)CN(C)S1(=O)=O] | Ex. 4, steps (a)-(b); Ex. 5, step (a); Ex. 11 | (WO 2005063705) |
| 21 | 4-Cyano-1H-pyrrole-2-carboxylic acid [2-cyclohex-1-enyl-4-(2,6-dimethyl-1,1-dioxo-1$\lambda^6$[1,2,6]thiadiazinan-4-yl)-phenyl]-amide | 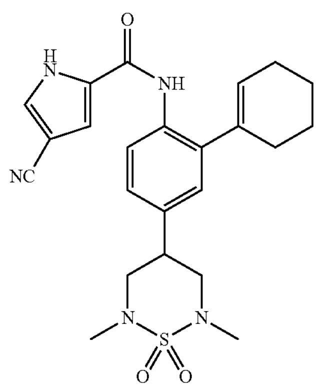 [SMILES: CN1CC(c2ccc(NC(=O)c3cc(C#N)c[nH]3)c(C3=CCCCC3)c2)CN(C)S1(=O)=O] | Ex. 11 | (Canadian J. Chem. 59, 2673 (1981)) |
| 22 | 4-Cyano-1H-imidazole-2-carboxylic acid [4-(2,6-dimethyl-1,1-dioxo-1$\lambda^6$-[1,2,6]thiadiazinan-4-yl)-2-spiro[2.5]oct-5-en-6-yl-phenyl]-amide | 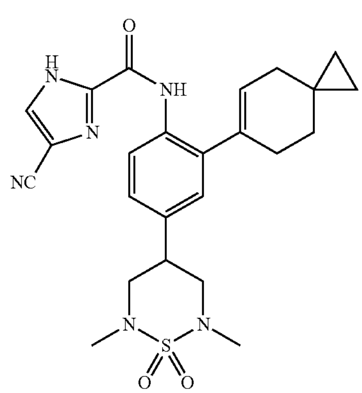 [SMILES: CN1CC(c2ccc(NC(=O)c3nc(C#N)c[nH]3)c(C3=CCC4(CC3)CC4)c2)CN(C)S1(=O)=O] | Ex. 4, steps (a)-(b); Ex. 5, step (a); Ex. 11 | (WO 2005063705) |

-continued

| Example No. | Name | Structure | Procedure Reference | Reagents |
|---|---|---|---|---|
| 23 | 4-Chloro-1H-imidazole-2-carboxylic acid [4-(2,6-dioxo-piperidin-4-yl)-2-spiro[3.5]non-6-en-7-yl-phenyl]-amide | 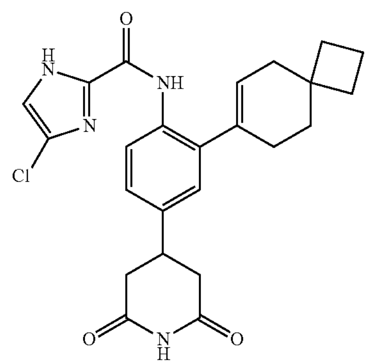 [SMILES: O=C1CC(c2ccc(NC(=O)c3nc(Cl)c[nH]3)c(C3=CCC4(CCC4)CC3)c2)CC(=O)N1] | Ex. 2 | (WO 2005063705); (Example 44, step (b)) |
| 24 | 5-Cyano-furan-2-carboxylic acid {2-(4,4-dimethyl-cyclohex-1-enyl)-4-[1-(2-hydroxy-ethyl)-2,6-dioxo-piperidin-4-yl]-phenyl}-amide | 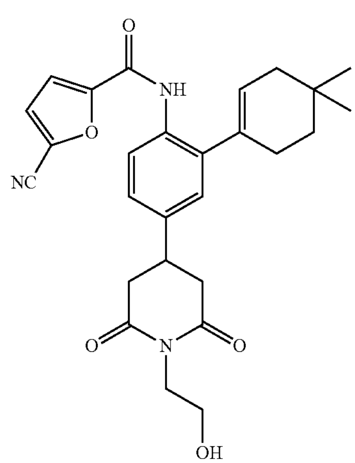 [SMILES: CC1(C)CC=C(c2cc(C3CC(=O)N(CCO)C(=O)C3)ccc2NC(=O)c2ccc(C#N)o2)CC1] | Ex. 15 | $H_2N(CH_2)_2OH$; (Combi-Blocks, Inc.); (WO 2004096795 A2) |

Example 25

5-Cyano-1H-imidazole-2-carboxylic acid [2-(4,4-dimethyl-cyclohex-1-enyl)-4-(2-methyl-1,1,3,3-tetraoxo-1$\lambda^6$, 3$\lambda^6$-[1,3,2]dithiazinan-5-yl)-phenyl]-amide

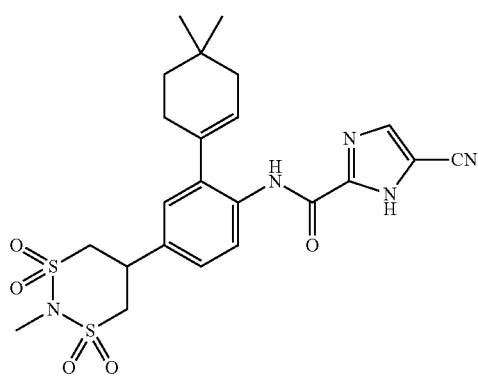 [SMILES: CN1S(=O)(=O)CC(c2ccc(NC(=O)c3ncc(C#N)[nH]3)c(C3=CCC(C)(C)CC3)c2)CS1(=O)=O]

b) 2-Phenyl-propane-1,3-disulfonic acid

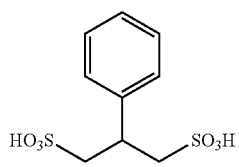 [SMILES: O=S(=O)(O)CC(CS(=O)(=O)O)c1ccccc1]

To 2-phenyl-propene-1,3-disulfonic acid (J. Amer. Chem. Soc., 66, 1105-9 (1944)) in THF-water (1:1) is added 10 wt % of 5% palladium on carbon and the mixture hydrogenated on a Parr shaker under 15 lb hydrogen pressure until the reaction is complete by thin layer chromatography (TLC). The mixture is filtered (Celite) and concentrated in vacuo to afford the title compound.

c) 2-(4-Nitro-phenyl)-propane-1,3-disulfonic acid

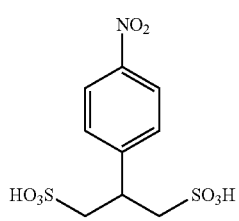 [SMILES: O=[N+]([O-])c1ccc(C(CS(=O)(=O)O)CS(=O)(=O)O)cc1]

2-Phenyl-propane-1,3-disulfonic acid (as prepared in the previous step) is treated with concentrated $H_2SO_4$ and fuming $HNO_3$ according to the procedure of Example 2, step (a) to afford the title compound.

c) 4-(4-Nitro-phenyl)-[1,2,6]oxadithiane 2,2,6,6-tetraoxide

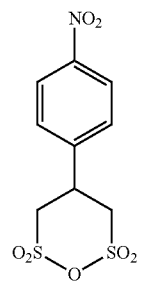

2-(4-Nitro-phenyl)-propane-1,3-disulfonic acid (as prepared in the previous step) is treated with POCl$_3$ as described in Chem. Berichte., 91, 1512-15 (1958) and the title compound is isolated and used in the following step without further purification.

d) 2-(4-Methoxy-benzyl)-5-(4-nitro-phenyl)-[1,3,2]dithiazinane 1,1,3,3-tetraoxide

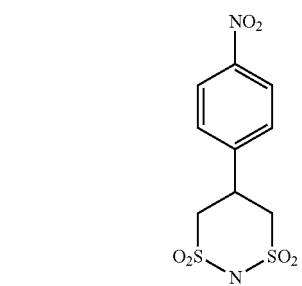 [SMILES: O=[N+]([O-])c1ccc(C2CS(=O)(=O)OS(=O)(=O)C2)cc1]

A solution of 4-(4-nitro-phenyl)-[1,2,6]oxadithiane 2,2,6,6-tetraoxide (as prepared in the previous step) is treated with 4-methoxy-benzylamine according to the procedure of Example 2, step (c) to afford the title compound.

e) 5-(4-Nitro-phenyl)-[1,3,2]dithiazinane 1,1,3,3-tetraoxide

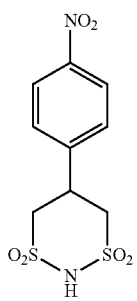 [SMILES: O=[N+]([O-])c1ccc(C2CS(=O)(=O)NS(=O)(=O)C2)cc1]

2-(4-Methoxy-benzyl)-5-(4-nitro-phenyl)-[1,3,2]dithiazinane 1,1,3,3-tetraoxide (as prepared in the previous step) is treated with ceric ammonium nitrate (CAN) according to the procedure of Example 2, step (d) to afford the title compound.

f) 5-Cyano-1H-imidazole-2-carboxylic acid [2-(4,4-dimethyl-cyclohex-1-enyl)-4-(2-methyl-1,1,3,3-tetraoxo-1$\lambda^6$, 3$\lambda^6$-[1,3,2]dithiazinan-5-yl)-phenyl]-amide The title compound is prepared from 5-(4-nitro-phenyl)-[1,3,2]dithiazinane 1,1,3,3-tetraoxide (as prepared in the previous step) using procedures similar to those found in Example 1, steps (i)-(m).

The following compounds are prepared by methods similar to previous examples and with the corresponding reagents as indicated in the table.

| | | | | |
|---|---|---|---|---|
| 26 | 4-Methyl-1H-imidazole-2-carboxylic acid [2-cyclohex-1-enyl-4-(2-ethyl-1,1,3,3-tetraoxo-1$\lambda^6$,3$\lambda^6$-[1,3,2]dithiazinan-5-yl)-phenyl]-amide | 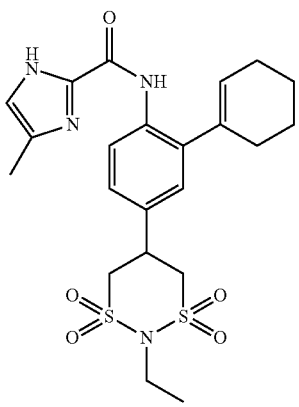 [SMILES: CCN1S(=O)(=O)CC(c2ccc(NC(=O)c3nc(C)c[nH]3)c(C3=CCCCC3)c2)CS1(=O)=O] | Ex. 25 above, steps (a)-(c), (e)-(f) | EtNH2; 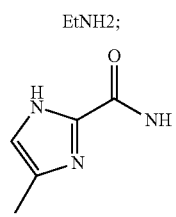 (Example 28, step (c)) |
| 27 | 4-Cyano-1H-pyrrole-2-carboxylic acid [2-spiro[5.5]undec-2-en-3-yl-4-(1,1,3,3-tetraoxo-1$\lambda^6$,3$\lambda^6$-[1,3,2]dithiazinan-5-yl)-phenyl]-amide | 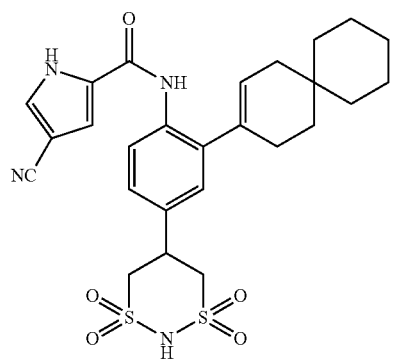 [SMILES: N#Cc1c[nH]c(C(=O)Nc2ccc(C3CS(=O)(=O)NS(=O)(=O)C3)cc2C2=CCC3(CCCCC3)CC2)c1] | Ex. 25 above | 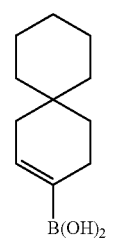 (WO 2005063705); 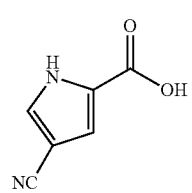 (*Canadian J. Chem.* 59, 2673 (1981)) |

Example 28

4-Methyl-1H-imidazole-2-carboxylic acid [4-(2,6-diethyl-1,1-dioxo-1λ⁶-[1,2,6]thiadiazinan-4-yl)-2-(4-methyl-piperidin-1-yl)-phenyl]-amide

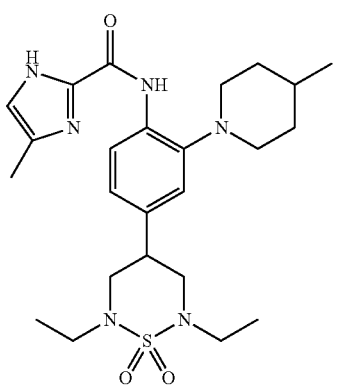 [SMILES: CCN1CC(c2ccc(NC(=O)c3nc(C)c[nH]3)c(N3CCC(C)CC3)c2)CN(CC)S1(=O)=O]

a) 5-Methyl-1-(2-trimethylsilanyl-ethoxymethyl)-1H-imidazole

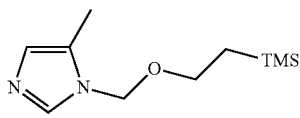

To a solution of 4-methylimidazole (2.70 g, 33.0 mmol) in 10 mL of acetonitrile at 0° C. was added triethylamine (NEt₃) (4.00 g, 39.6 mmol) and acetyl chloride (2.80 g, 36.3 mmol). The mixture was allowed to attain RT then filtered to remove the ppt and the filtrate was concentrated to give 1-(4-methyl-imidazol-1-yl)-ethanone, which was used without further purification in the next step. To a solution of 1-(4-methyl-imidazol-1-yl)-ethanone (4.10 g, 33.0 mmol) in 15 mL acetonitrile was added SEM-Cl (5.80 g, 35.0 mmol) and the solution was stirred at 25° C. for 10 h. The solvents were removed by evaporation and to the residue was added 100 mL of 2.5 M NaOH and the mixture was stirred at 25° C. for 1 h. The reaction mixture was then extracted with ether (3×100 mL), dried over Na₂SO₄ and concentrated. The title compound was purified by chromatography on silica gel eluting with 75% EtOAc/hexanes to give 4.30 g (61%) of a colorless oil: Mass spectrum (ESI, m/z): Calcd. for $C_{10}H_{20}N_2O_4Si$, 213.1 (M+H). found 213.1.

b) 5-Methyl-1-(2-trimethylsilanyl-ethoxymethyl)-1H-imidazole-2-carboxylic acid ethyl ester

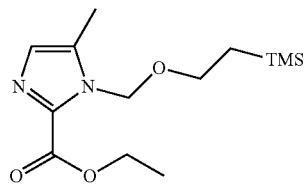 [SMILES: CCOC(=O)c1ncc(C)n1COCC[Si](C)(C)C]

To a solution of 5-methyl-1-(2-trimethylsilanyl-ethoxymethyl)-1H-imidazole (as prepared in the previous step, 0.320 g, 1.50 mmol) in 5 mL of THF at −78° C. was added n-BuLi (0.80 mL, 2 M in cyclohexane) and the mixture was allowed to attain RT and stirred for 30 min. The mixture was cooled to −78° C. and ethyl cyanoformate (0.160 g, 1.65 mmol) was added and the mixture allowed to stir for 10 h at RT. The reaction was diluted with 15 mL of EtOAc and washed with NaHCO₃ (2×15 mL) and brine (15 mL). The title compound was eluted from a 20-g SPE with 50% EtOAc/hexanes to give 0.160 g (38%) of a light brown oil: Mass spectrum (ESI, m/z): Calcd. for $C_{13}H_{24}N_2O_3Si$, 285.2 (M+H). found 284.9.

c) 5-Methyl-1-(2-trimethylsilanyl-ethoxymethyl)-1H-imidazole-2-carboxylic acid potassium salt

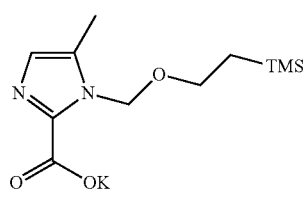

To a solution of 5-methyl-1-(2-trimethylsilanyl-ethoxymethyl)-1H-imidazole-2-carboxylic acid ethyl ester (as prepared in the previous step, 0.090 g, 0.32 mmol) in 2 mL of ethyl alcohol (EtOH) at RT was added 0.16 mL of 2N KOH. The mixture was stirred for 1 h and then concentrated and d) [4-(2,6-Diethyl-1,1-dioxo-1λ$^6$-[1,2,6]thiadiazinan-4-yl)-phenyl]-carbamic acid tert-butyl ester

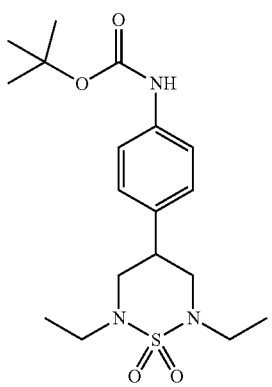 [SMILES: CCN1CC(c2ccc(NC(=O)OC(C)(C)C)cc2)CN(CC)S1(=O)=O]

The title compound is prepared from N-[4-(1,1-dioxo-1λ$^6$-[1,2,6]thiadiazinan-4-yl)-phenyl]-acetamide (as prepared in Example 5, step (a)) and EtI following the procedure of Example 11, step (a).

e) [2-Bromo-4-(2,6-diethyl-1,1-dioxo-1λ$^6$-[1,2,6]thiadiazinan-4-yl)-phenyl]-carbamic acid tert-butyl ester

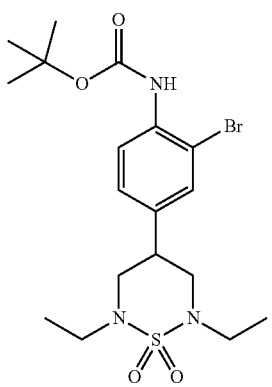 [SMILES: CCN1CC(c2ccc(NC(=O)OC(C)(C)C)c(Br)c2)CN(CC)S1(=O)=O]

The title compound is prepared from [4-(2,6-diethyl-1,1-dioxo-1λ$^6$-[1,2,6]thiadiazinan-4-yl)-phenyl]-carbamic acid tert-butyl ester (as prepared in the previous step) following the procedure of Example 11, step (b).

f) 4-(2,6-Diethyl-1,1-dioxo-1λ$^6$-[1,2,6]thiadiazinan-4-yl)-2-(4-methyl-piperidin-1-yl)-phenylamine

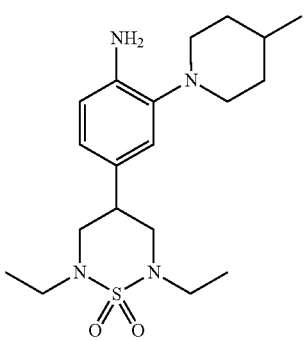 [SMILES: CCN1CC(c2ccc(N)c(N3CCC(C)CC3)c2)CN(CC)S1(=O)=O]

The title compound is prepared from [2-bromo-4-(2,6-diethyl-1,1-dioxo-1λ$^6$-[1,2,6]thiadiazinan-4-yl)-phenyl]-carbamic acid tert-butyl ester (as prepared in the previous step) and 4-methylpiperidine following the literature procedure of Buchwald (*Org. Lett.*, 4, 2885-8 (2002)). The residue obtained is purified by silica gel chromatography with an appropriate solvent mixture. After isolation, removal of the BOC protecting group from the resulting intermediate is carried out by stirring at RT in TFA-DCM (1:2), monitoring by TLC for completion, and then concentration in vacuo.

g) 4-Methyl-1H-imidazole-2-carboxylic acid [4-(2,6-diethyl-1,1-dioxo-1λ$^6$-[1,2,6]thiadiazinan-4-yl)-2-(4-methyl-piperidin-1-yl)-phenyl]-amide The title compound is prepared from 4-(2,6-diethyl-1,1-dioxo-1λ$^6$-[1,2,6]thiadiazinan-4-yl)-2-(4-methyl-piperidin-1-yl)-phenylamine (as prepared in the previous step) and 5-methyl-1-(2-trimethylsilanyl-ethoxymethyl)-1H-imidazole-2-carboxylic acid potassium salt (as prepared above in this example, step (c)) following the procedure of Example 11, steps (d)-(e).

The following compounds are prepared by methods similar to the previous example, with or without additional procedures, and with the corresponding reagents as indicated in the table.

| Example No. | Name | Structure | Procedure Reference | Reagents |
|---|---|---|---|---|
| 29 | 4-Cyano-1H-imidazole-2-carboxylic acid [4-(1,3-dimethyl-2-oxo-hexahydro-pyrimidin-5-yl)-2-(4-methyl-piperidin-1-yl)-phenyl]-amide | 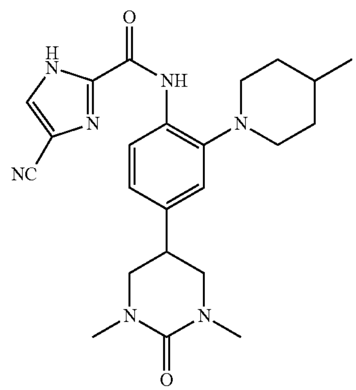 [SMILES: CC1CCN(c2cc(C3CN(C)C(=O)N(C)C3)ccc2NC(=O)c2nc(C#N)c[nH]2)CC1] | Example 7, step (a); Example 4, step (b); Example 7, step (d); Example 28, steps (e)-(f) | (Example 7, step (a)) |
| 30 | 5-Cyano-furan-2-carboxylic acid [4-(1,3-dimethyl-2-oxo-hexahydro-pyrimidin-5-yl)-2-(4,4-dimethyl-piperidin-1-yl)-phenyl]-amide | 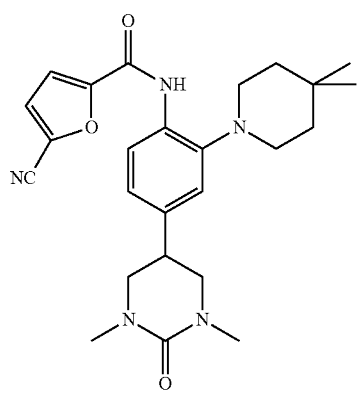 [SMILES: CN1CC(c2ccc(NC(=O)c3ccc(C#N)o3)c(N3CCC(C)(C)CC3)c2)CN(C)C1=O] | Example 29 | (US 2003236247); (WO 2004096795 A2) |
| 31 | 4-Cyano-1H-pyrrole-2-carboxylic acid [4-(1,3-dimethyl-2-oxo-hexahydro-pyrimidin-5-yl)-2-(4,4-dimethyl-piperidin-1-yl)-phenyl]-amide | 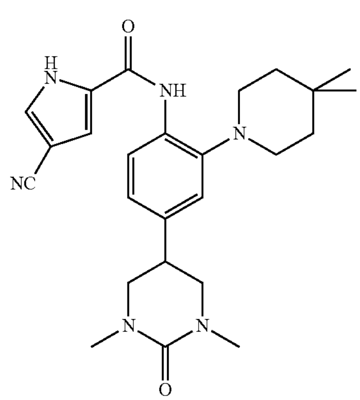 [SMILES: CN1CC(c2ccc(NC(=O)c3cc(C#N)c[nH]3)c(N3CCC(C)(C)CC3)c2)CN(C)C1=O] | Example 29 | (US 2003236247) (Canadian J. Chem. 59, 2673 (1981)) |

| Example No. | Name | Structure | Procedure Reference | Reagents |
|---|---|---|---|---|
| 32 | 5-Cyano-2H-[1,2,4]triazole-3-carboxylic acid [2-(8-aza-spiro[4.5]dec-8-yl)-4-(1,3-dimethyl-2-oxo-hexahydro-pyrimidin-5-yl)-phenyl]-amide | 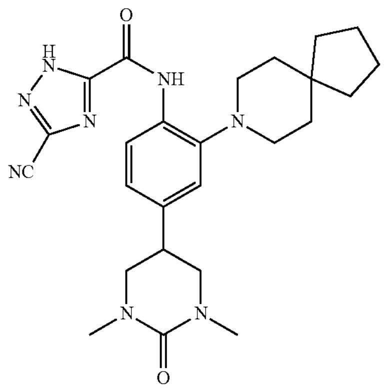 [SMILES: CN1CC(c2ccc(NC(=O)c3nc(C#N)n[nH]3)c(N3CCC4(CCCC4)CC3)c2)CN(C)C1=O] | Example 29 | (J. Med. Chem., 8, 766-76 (1965)); (Hecheng Huaxue, 11(4), 351-353 (2003)) |
| 33 | 4-Cyano-1H-imidazole-2-carboxylic acid [4-(2,6-dimethyl-1,1-dioxo-1$\lambda^6$-[1,2,6]thiadiazinan-4-yl)-2-(4,4-dimethyl-piperidin-1-yl)-phenyl]-amide | 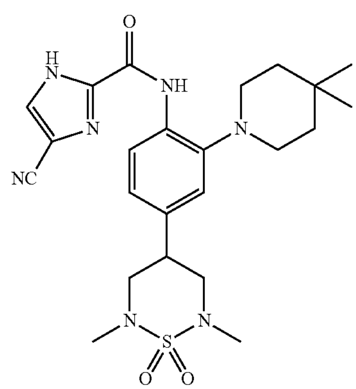 [SMILES: CN1CC(c2ccc(NC(=O)c3nc(C#N)c[nH]3)c(N3CCC(C)(C)CC3)c2)CN(C)S1(=O)=O] | Example 28 | (US 2003236247) |
| 34 | 4-Hydroxy-1H-imidazole-2-carboxylic acid {4-(2,6-dimethyl-1,1-dioxo-1$\lambda^6$-[1,2,6]thiadiazinan-4-yl)-2-[4-(2-hydroxy-ethyl)-piperidin-1-yl]-phenyl}-amide | 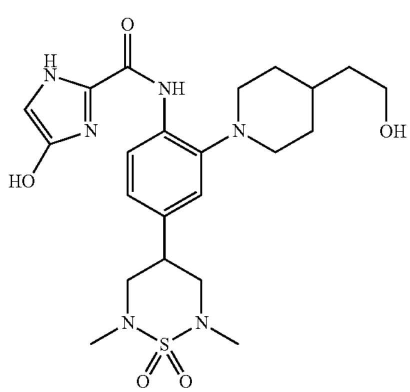 [SMILES: CN1CC(c2ccc(NC(=O)c3nc(O)c[nH]3)c(N3CCC(CCO)CC3)c2)CN(C)S1(=O)=O] | Example 28 | (WO 9811086 A1); (Berichte, 58B, 1346-53 (1925)) |

The following compounds are prepared by methods similar to previous examples with additional procedures and with the corresponding reagents as indicated in the table.

| Example No. | Name | Structure | Procedure Reference | Reagents |
|---|---|---|---|---|
| 35 | 4-Cyano-1H-imidazole-2-carboxylic acid [4-(2,6-dioxo-piperidin-4-yl)-2-piperidin-1-yl-phenyl]-amide | 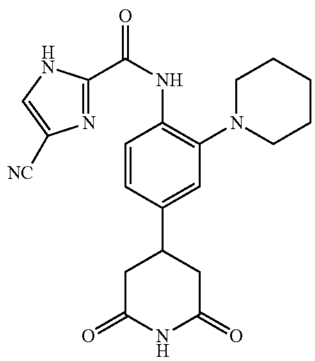 [SMILES: N#Cc1c[nH]c(C(=O)Nc2ccc(C3CC(=O)NC(=O)C3)cc2N2CCCCC2)n1] | Example 1, steps (a)-(j); Example 28, step (e); Example 1, steps (l)-(m) | |
| 36 | 4-Cyano-1H-imidazole-2-carboxylic acid [4-(2,6-dioxo-piperidin-4-yl)-2-(4-methyl-piperidin-1-yl)-phenyl]-amide | 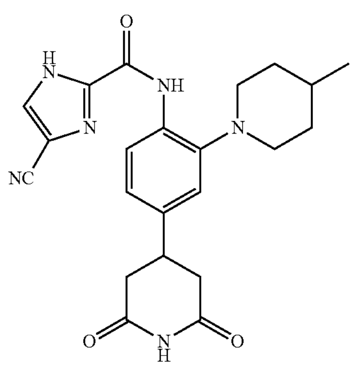 [SMILES: CC1CCN(c2cc(C3CC(=O)NC(=O)C3)ccc2NC(=O)c2nc(C#N)c[nH]2)CC1] | Example 1, steps (a)-(j); Example 28, step (e); Example 1, steps (l)-(m) | |
| 37 | 4-Cyano-1H-pyrrole-2-carboxylic acid [4-(2,6-dioxo-piperidin-4-yl)-2-(4-methyl-piperidin-1-yl)-phenyl]-amide | 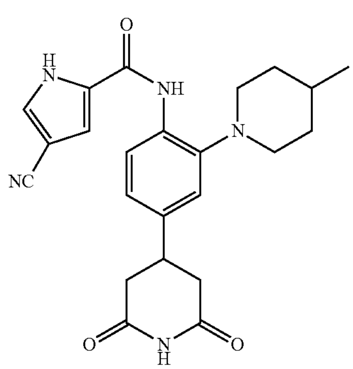 [SMILES: CC1CCN(c2cc(C3CC(=O)NC(=O)C3)ccc2NC(=O)c2cc(C#N)c[nH]2)CC1] | Example 1, steps (a)-(j); Example 28, step (e); Example 1, steps (l)-(m) | (Canadian J. Chem. 59, 2673 (1981)) |

-continued

| Example No. | Name | Structure | Procedure Reference | Reagents |
|---|---|---|---|---|
| 38 | 5-Cyano-furan-2-carboxylic acid [2-(4,4-dimethyl-piperidin-1-yl)-4-(1-methyl-2,6-dioxo-piperidin-4-yl)-phenyl]-amide | 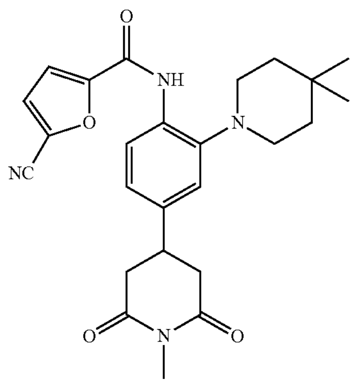 [SMILES: CN1C(=O)CC(c2ccc(NC(=O)c3ccc(C#N)o3)c(N3CCC(C)(C)CC3)c2)CC1=O] | Example 15, (a)-(b); Example 4, (a) and (d); Example 28, step (e); Example 1, steps (l)-(m) | MeNH$_2$; (US 2003236247); (WO 2004096795 A2) |
| 39 | 5-Cyano-1H-imidazole-2-carboxylic acid [2-(4-methyl-piperidin-1-yl)-4-(2-methyl-1,1,3,3-tetraoxo-1λ$^6$,3λ$^6$-[1,3,2]dithiazinan-5-yl)-phenyl]-amide | 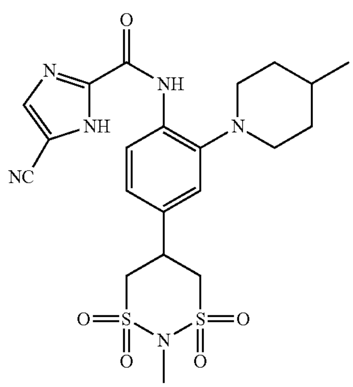 [SMILES: CC1CCN(c2cc(C3CS(=O)(=O)N(C)S(=O)(=O)C3)ccc2NC(=O)c2ncc(C#N)[nH]2)CC1] | Example 25, steps (a)-(d); Example 1, step (i); Example 43, step (c); Example 4, step (d); Example 28, step (e); Example 1, steps (l)-(m) | MeNH$_2$ |
| 40 | 5-Cyano-4H-[1,2,4]triazole-3-carboxylic acid [2-(8-aza-spiro[4.5]dec-8-yl)-4-(1,1,3,3-tetraoxo-1λ$^6$,3λ$^6$-[1,3,2]dithiazinan-5-yl)-phenyl]-amide | 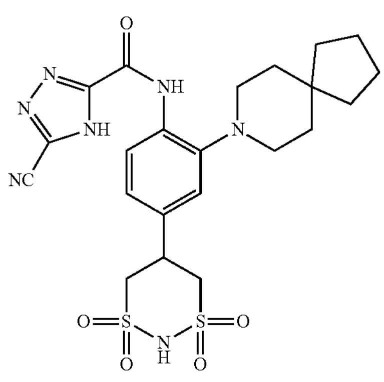 [SMILES: N#Cc1nnc(C(=O)Nc2ccc(C3CS(=O)(=O)NS(=O)(=O)C3)cc2N2CCC3(CCCC3)CC2)[nH]1] | Example 25, steps (a)-(d); Example 15, step (c); Example 43, step (c); Example 4, steps (a) and (d); Example 28, step (e); Example 1, steps (l)-(m); Example 2, step (d) | (J. Med. Chem., 8, 766-76 (1965)); (Hecheng Huaxue, 11(4), 351-353 (2003)) |

The following compound is prepared by methods similar to previous examples with additional procedures and with the corresponding reagents as indicated in the table.

| Example No. | Name | Structure | Procedure Reference | Reagents |
|---|---|---|---|---|
| 41 | 4-Cyano-1H-imidazole-2-carboxylic acid [6-(4,4-dimethyl-cyclohex-1-enyl)-2',6'-dioxo-1',2',3',4',5',6'-hexahydro-[2,4']bipyridinyl-5-yl]-amide | 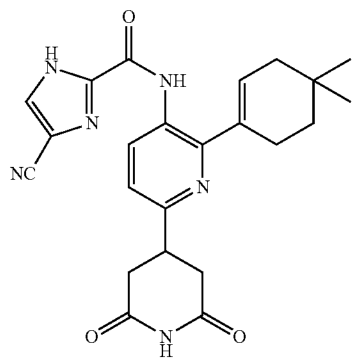 [SMILES: CC1(C)CC=C(c2nc(C3CC(=O)NC(=O)C3)ccc2NC(=O)c2nc(C#N)c[nH]2)CC1] | Example 2 | (WO 9737979 A1); (Combi-Blocks, Inc.) |

The following compound is prepared by methods similar to previous examples with additional procedures and with the corresponding reagents as indicated in the table.

| Example No. | Name | Structure | Procedure Reference | Reagents |
|---|---|---|---|---|
| 42 | 4-Cyano-1H-imidazole-2-carboxylic acid (4-methyl-2'',6''-dioxo-3,4,5,6,1'',2'',3'',4'',5'',6''-decahydro-2H-[1,2';6',4'']terpyridin-3'-yl)-amide | 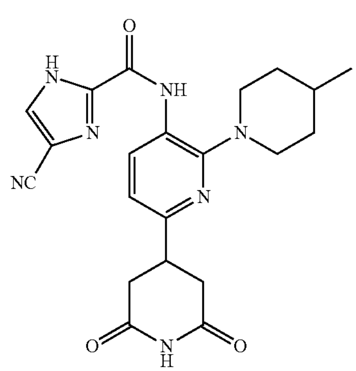 [SMILES: CC1CCN(c2nc(C3CC(=O)NC(=O)C3)ccc2NC(=O)c2nc(C#N)c[nH]2)CC1] | Example 2, steps (a)-(d); Example 1, steps (i); Example 4, step (a); Example 43, step (h); Example 1, steps (l)-(m) | (WO 9737979 A1); |

Example 43

4-Cyano-1H-imidazole-2-carboxylic acid [6'-(1,3-dimethyl-2-oxo-hexahydro-pyrimidin-5-yl)-4,4-dimethyl-3,4,5,6-tetrahydro-2H-[1,2']bipyridinyl-3'-yl]-amide

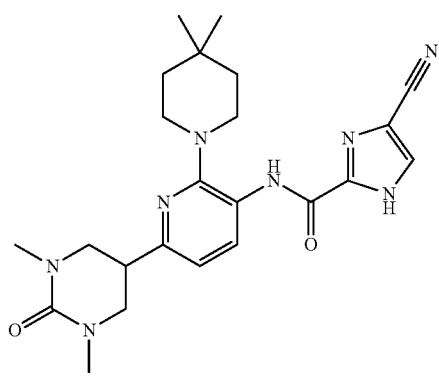 [SMILES: CN1CC(c2ccc(NC(=O)c3nc(C#N)c[nH]3)c(N3CCC(C)(C)CC3)n2)CN(C)C1=O]

a) 2-(5-Nitro-pyridin-2-yl)-propane-1,3-diol

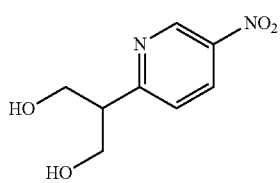 [SMILES: O=[N+]([O-])c1ccc(C(CO)CO)nc1]

The title compound is prepared from 2-pyridin-2-yl-propane-1,3-diol (*Tetrahedron: Asymmetry* 8(13), 2175-2187 (1997)) according to the procedure in Example 2, step (a).

b) 2-(5-Amino-pyridin-2-yl)-propane-1,3-diol

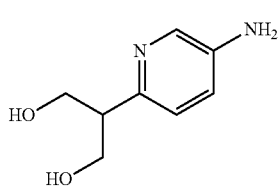

The title compound is prepared from 2-(5-nitro-pyridin-2-yl)-propane-1,3-diol (as prepared in the previous step) according to the procedure in Example 1, step (i).

c) [6-(2-Hydroxy-1-hydroxymethyl-ethyl)-pyridin-3-yl]-carbamic acid tert-butyl ester

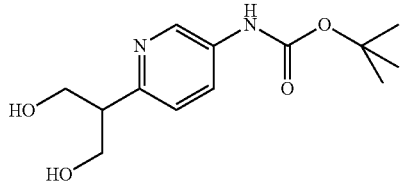 [SMILES: CC(C)(C)OC(=O)Nc1ccc(C(CO)CO)nc1]

The title compound is prepared from 2-(5-amino-pyridin-2-yl)-propane-1,3-diol (as prepared in the previous step) and (BOC)$_2$O according to standard procedures found in "Protective Groups in Organic Synthesis", by Theodora W. Greene and Peter G. M. Wuts, John Wiley & Sons, Inc. NY, (1999).

d) [6-(2-Amino-1-aminomethyl-ethyl)-pyridin-3-yl]-carbamic acid tert-butyl ester

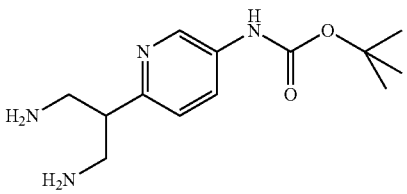 [SMILES: CC(C)(C)OC(=O)Nc1ccc(C(CN)CN)nc1]

The title compound is prepared from [6-(2-hydroxy-1-hydroxymethyl-ethyl)-pyridin-3-yl]-carbamic acid tert-butyl ester (as prepared in the previous step) according to the procedure in Example 4, step (b).

e) [6-(2-Oxo-hexahydro-pyrimidin-5-yl)-pyridin-3-yl]-carbamic acid tert-butyl ester

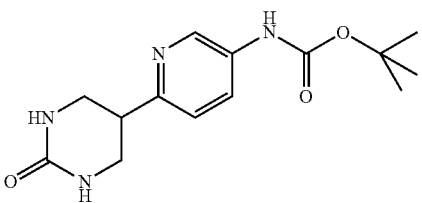 [SMILES: CC(C)(C)OC(=O)Nc1ccc(C2CNC(=O)NC2)nc1]

The title compound is prepared from [6-(2-amino-1-aminomethyl-ethyl)-pyridin-3-yl]-carbamic acid tert-butyl ester (as prepared in the previous step) according to the procedure in Example 4, step (c).

f) [6-(1,3-Dimethyl-2-oxo-hexahydro-pyrimidin-5-yl)-pyridin-3-yl]-carbamic acid tert-butyl ester

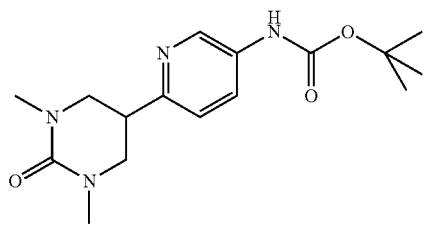 [SMILES: CN1CC(c2ccc(NC(=O)OC(C)(C)C)cn2)CN(C)C1=O]

The title compound is prepared from [6-(2-oxo-hexahydro-pyrimidin-5-yl)-pyridin-3-yl]-carbamic acid tert-butyl ester (as prepared in the previous step) according to the procedure in Example 7, step (a).

g) [2-Bromo-6-(1,3-dimethyl-2-oxo-hexahydro-pyrimidin-5-yl)-pyridin-3-yl]-carbamic acid tert-butyl ester

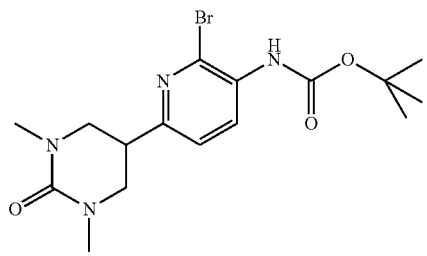 [SMILES: CN1CC(c2ccc(NC(=O)OC(C)(C)C)c(Br)n2)CN(C)C1=O]

The title compound is prepared from [6-(1,3-dimethyl-2-oxo-hexahydro-pyrimidin-5-yl)-pyridin-3-yl]-carbamic acid tert-butyl ester (as prepared in the previous step) according the procedure in Example 4, step (d).

h) 5-(3'-Amino-4,4-dimethyl-3,4,5,6-tetrahydro-2H-[1,2']bipyridinyl-6'-yl)-1,3-dimethyl-tetrahydro-pyrimidin-2-one

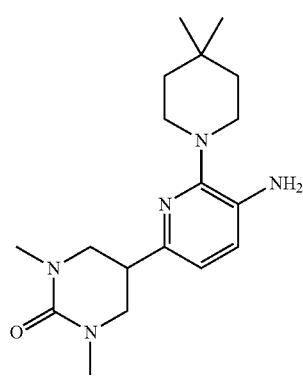 [SMILES: CN1CC(c2ccc(N)c(N3CCC(C)(C)CC3)n2)CN(C)C1=O]

The title compound is prepared from [2-bromo-6-(1,3-dimethyl-2-oxo-hexahydro-pyrimidin-5-yl)-pyridin-3-yl]-carbamic acid tert-butyl ester (as prepared in the previous step) and 4,4-dimethylpiperidine (US 2003236247) following the literature procedure of Buchwald (*Org. Lett.*, 4, 2885-8 (2002)). The residue obtained is purified by silica gel chromatography with an appropriate solvent mixture. After isolation, removal of the BOC protecting group from the resulting intermediate is carried out by stirring at RT in TFA-DCM (1:2), monitoring by TLC for completion, and then concentration in vacuo.

i) 4-Cyano-1H-imidazole-2-carboxylic acid [6'-(1,3-dimethyl-2-oxo-hexahydro-pyrimidin-5-yl)-4,4-dimethyl-3,4,5,6-tetrahydro-2H-[1,2']bipyridinyl-3'-yl]-amide The title compound is prepared from 5-(3'-amino-4,4-dimethyl-3,4,5,6-tetrahydro-2H-[1,2']bipyridinyl-6'-yl)-1,3-dimethyl-tetrahydro-pyrimidin-2-one (as prepared in the previous step) according to the procedures in Example 1, steps (l) and (m).

Example 44

4-Chloro-1H-imidazole-2-carboxylic acid [6'-(2,6-diethyl-1,1-dioxo-1$\lambda^6$-[1,2,6]thiadiazinan-4-yl)-4-methyl-3,4,5,6-tetrahydro-2H-[1,2']bipyridinyl-3'-yl]-amide

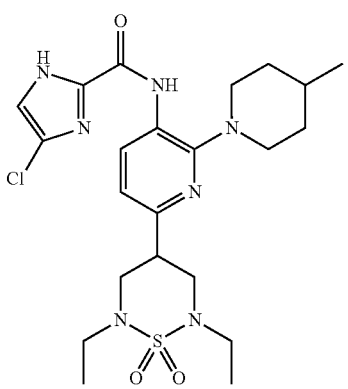 [SMILES: CCN1CC(c2ccc(NC(=O)c3nc(Cl)c[nH]3)c(N3CCC(C)CC3)n2)CN(CC)S1(=O)=O]

a) 4-Chloro-1-(2-trimethylsilanyl-ethoxymethyl)-1H-imidazole-2-carboxylic acid ethyl ester

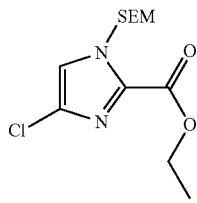

The title compound was prepared according to the procedure of Example 51, step (b) substituting N-chlorosuccinimide (NCS) for NBS. Mass spectrum (ESI, m/z): Calcd. for $C_{12}H_{21}ClN_2O_3Si$, 305.1 (M+H). found 304.7.

b) 4-Chloro-1-(2-trimethylsilanyl-ethoxymethyl)-1H-imidazole-2-carboxylate potassium salt

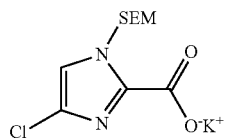

The title compound was prepared from 4-chloro-1-(2-trimethylsilanyl-ethoxymethyl)-1H-imidazole-2-carboxylic acid ethyl ester (prepared in the previous step) according to the procedure in Example 1, step(d). Mass spectrum (ESI, m/z): Calcd. for $C_{10}H_{16}ClKN_2O_3Si$, 277.1 (M+H—K). found 276.7.

c) 6'-(2,6-Diethyl-1,1-dioxo-1$\lambda^6$-[1,2,6]thiadiazinan-4-yl)-4-methyl-3,4,5,6-tetrahydro-2H-[1,2']bipyridinyl-3'-ylamine

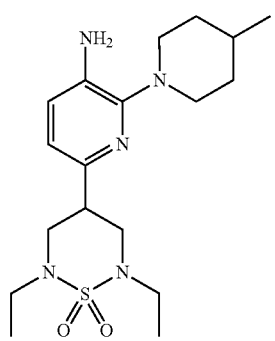 [SMILES: CCN1CC(c2ccc(N)c(N3CCC(C)CC3)n2)CN(CC)S1(=O)=O]

The title compound is prepared from 4-chloro-1-(2-trimethylsilanyl-ethoxymethyl)-1H-imidazole-2-carboxylic acid ethyl ester (prepared in the previous step) according to the procedure in Example 1, steps (a)-(h) substituting EtI for $Me_2SO_4$.

d) 4-Chloro-1H-imidazole-2-carboxylic acid [6'-(2,6-diethyl-1,1-dioxo-1$^6$-[1,2,6]thiadiazinan-4-yl)-4-methyl-3,4,5,6-tetrahydro-2H-[1,2']bipyridinyl-3'-yl]-amide The title compound is prepared from 6'-(2,6-diethyl-1,1-dioxo-1$\lambda^6$-[1,2,6]thiadiazinan-4-yl)-4-methyl-3,4,5,6-tetrahydro-2H-[1,2]bipyridinyl-3'-ylamine (as prepared in the previous step) and 4-chloro-1-(2-trimethylsilanyl-ethoxymethyl)-1H-imidazole-2-carboxylate potassium salt (as prepared in this example, step (b) following the procedure of Example 1, step (l)) followed by the procedure of Example 1, step (m).

The following compounds are prepared by methods similar to the previous example with the corresponding reagents as indicated in the table.

| Example No. | Name | Structure | Procedure Reference | Reagents |
|---|---|---|---|---|
| 45 | 4-Cyano-1H-imidazole-2-carboxylic acid [6'-(1,3-dimethyl-2-oxo-hexahydro-pyrimidin-5-yl)-4,4-dimethyl-3,4,5,6-tetrahydro-2H-[1,2']bipyridinyl-3'-yl]-amide | 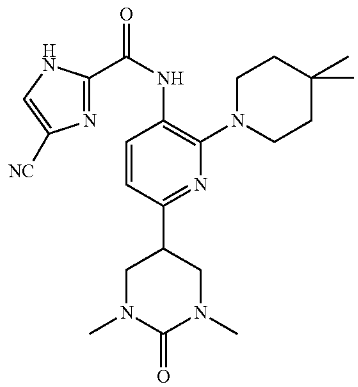 [SMILES: CN1CC(c2ccc(NC(=O)c3nc(C#N)c[nH]3)c(N3CCC(C)(C)CC3)n2)CN(C)C1=O] | Example 44 | (US 2003236247); (Example 1, step (d)) |
| 46 | 5-Cyano-2H-[1,2,4]triazole-3-carboxylic acid [6'-(2,6-dimethyl-1,1-dioxo-1$\lambda^6$-[1,2,6]thiadiazinan-4-yl)-4-methyl-3,4,5,6-tetrahydro-2H-[1,2']bipyridinyl-3'-yl]-amide | 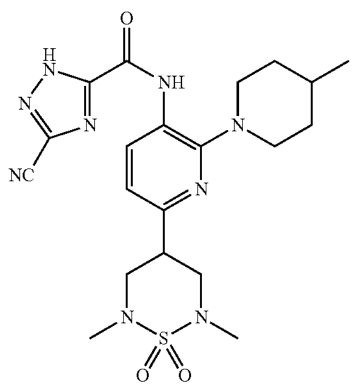 [SMILES: CC1CCN(c2nc(C3CN(C)S(=O)(=O)N(C)C3)ccc2NC(=O)c2nc(C#N)n[nH]2)CC1] | Example 44 | (Hecheng Huaxue, 11(4), 351-353 (2003)) |

The following compounds are prepared by methods similar to the previous examples with modifications and with the corresponding reagents as indicated in the table.

| Example No. | Name | Structure | Procedure Reference | Reagents |
|---|---|---|---|---|
| 47 | 4-Cyano-1H-imidazole-2-carboxylic acid [2-(4,4-dimethyl-cyclohex-1-enyl)-6-(1,3-dimethyl-2-oxo-hexahydro-pyrimidin-5-yl)-pyridin-3-yl]-amide | 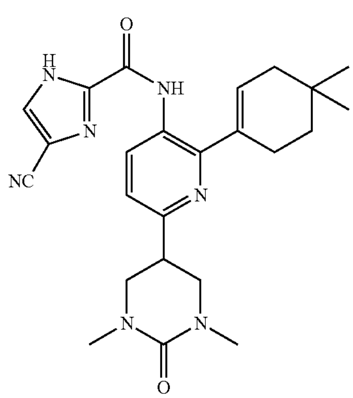 [SMILES: CN1CC(c2ccc(NC(=O)c3nc(C#N)c[nH]3)c(C3=CCC(C)(C)CC3)n2)CN(C)C1=O] | Example 43, steps (a)-(g); Example 3, step (a) and (c); Example 1, step (l)-(m) | (Combi-Blocks, Inc.) |

-continued

| Example No. | Name | Structure | Procedure Reference | Reagents |
|---|---|---|---|---|
| 48 | 5-Cyano-furan-2-carboxylic acid [6-(1,3-dimethyl-2-oxo-hexahydro-pyrimidin-5-yl)-2-spiro[4.5]dec-7-en-8-yl-pyridin-3-yl]-amide | 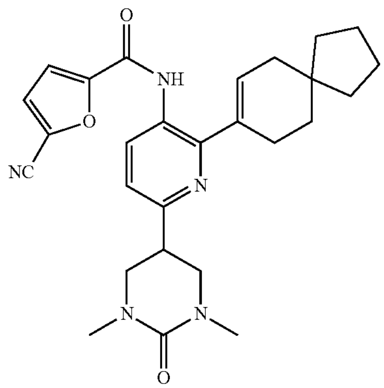 [SMILES: CN1CC(c2ccc(NC(=O)c3ccc(C#N)o3)c(C3=CCC4(CCCC4)CC3)n2)CN(C)C1=O] | Example 43, steps (a)-(g); Example 3, step (a) and (c); Example 1, step (l)-(m) | (WO 2005063705); (WO 2004096795 A2) |
| 49 | 4-Cyano-1H-pyrrole-2-carboxylic acid [2-(4,4-dimethyl-cyclohex-1-enyl)-6-(2,6-dimethyl-1,1-dioxo-1$\lambda^6$-[1,2,6]thiadiazinan-4-yl)-pyridin-3-yl]-amide | 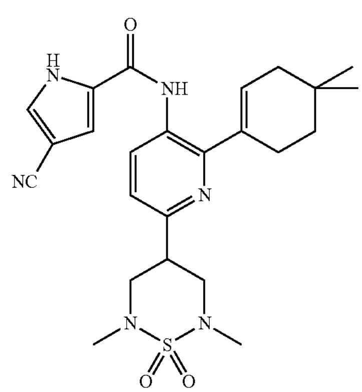 [SMILES: CN1CC(c2ccc(NC(=O)c3cc(C#N)c[nH]3)c(C3=CCC(C)(C)CC3)n2)CN(C)S1(=O)=O] | Example 43, steps (a)-(d); Example 5, step (a); Example 11, steps (a)-(d) | (Combi-Blocks, Inc.); (Canadian J. Chem. 59, 2673 (1981)) |

-continued

| Example No. | Name | Structure | Procedure Reference | Reagents |
|---|---|---|---|---|
| 50 | 4-Cyano-1H-imidazole-2-carboxylic acid [2-(4,4-dimethyl-cyclohex-1-enyl)-6-(2,6-dimethyl-1,1-dioxo-1λ⁶-[1,2,6]thiadiazinan-4-yl)-pyridin-3-yl]-amide | 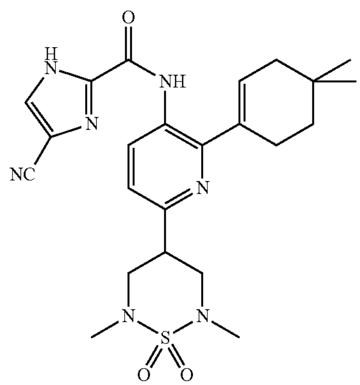 [SMILES: CN1CC(c2ccc(NC(=O)c3nc(C#N)c[nH]3)c(C3=CCC(C)(C)CC3)n2)CN(C)S1(=O)=O] | Example 43, steps (a)-(d); Example 5, step (a); Example 11, steps (a)-(e) | (Combi-Blocks, Inc.) |

Example 51

{5-[4-[(4-Bromo-1H-imidazole-2-carbonyl)-amino]-3-(4,4-dimethyl-cyclohex-1-enyl)-phenyl]-tetrahydro-pyrimidin-2-ylidene}-carbamic acid methyl ester

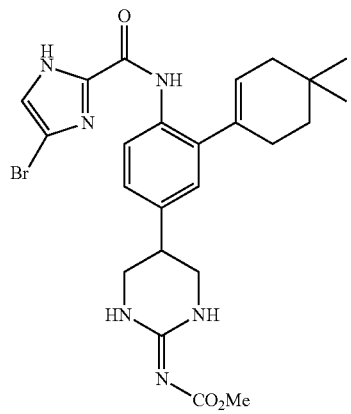 [SMILES: COC(=O)N=C1NCC(c2ccc(NC(=O)c3nc(Br)c[nH]3)c(C3=CCC(C)(C)CC3)c2)CN1]

a) 1-(2-Trimethylsilanyl-ethoxymethyl)-1H-imidazole-2-carboxylic acid ethyl ester

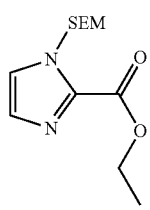 [SMILES: CCOC(=O)c1nccn1COCC[Si](C)(C)C]

A flask charged with 1H-imidazole-2-carboxylic acid ethyl ester (1.03 g, 7.36 mmol), $K_2CO_3$ (2.00 g, 14.5 mmol), SEM-Cl (1.56 mL, 8.89 mmol), and 20 mL of acetone was stirred for 10 h at RT. The reaction was diluted with EtOAc (100 mL), washed with $NaHCO_3$ (2×100 mL), brine (100 mL), and the organic layer dried over $Na_2SO_4$ and concentrated. The title compound was eluted from a 20-g SPE with 50% EtOAc/hexanes to give 1.50 g (76%) of a colorless oil. Mass spectrum (ESI, m/z): Calcd. for $C_{12}H_{22}N_3O_3Si$, 271.1 (M+H). found 271.1.

b) 4-Bromo-1-(2-trimethylsilanyl-ethoxymethyl)-1H-imidazole-2-carboxylic acid ethyl ester

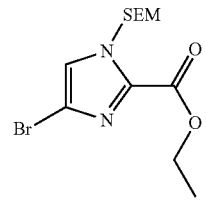 [SMILES: CCOC(=O)c1nc(Br)cn1COCC[Si](C)(C)C]

To a solution of 1-(2-trimethylsilanyl-ethoxymethyl)-1H-imidazole-2-carboxylic acid ethyl ester (0.20 g, 0.74 mmol) (prepared in the previous step) in 2 mL of $CH_3CN$ was added NBS (0.13 g, 0.74 mmol) and the mixture heated to 60° C. for 2 h. The mixture was concentrated and the title compound purified by elution from a 20-g SPE column with 20% EtOAc/hexanes to give 0.10 g (39%) of a colorless oil. Mass spectrum (ESI, m/z): Calcd. for $C_{12}H_{21}BrN_2O_3Si$, 349.0 (M+H). found 348.7.

c) 4-Bromo-1-(2-trimethylsilanyl-ethoxymethyl)-1H-imidazole-2-carboxylate potassium salt

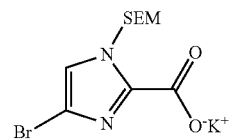

The title compound was prepared according to the procedure in Example 1, step (d). Mass spectrum (ESI, m/z): Calcd. for $C_{10}H_{16}BrKN_2O_3Si$, 322.0 (M+H—K). found 322.6.

d) {5-[4-[(4-Bromo-1H-imidazole-2-carbonyl)-amino]-3-(4,4-dimethyl-cyclohex-1-enyl)-phenyl]-tetrahydro-pyrimidin-2-ylidene}-carbamic acid methyl ester The title compound is prepared according to the procedures in Example 12 substituting 4-bromo-1-(2-trimethylsilanyl-ethoxymethyl)-1H-imidazole-2-carboxylate potassium salt (as prepared in this example, step (c)) for 4-cyano-1-(2-trimethylsilanyl-ethoxymethyl)-1H-imidazole-2-carboxylate potassium salt and substituting 4,4-dimethyl-cyclohex-1-enylboronic acid for cyclohex-1-enylboronic acid.

Examples 52 and 53 are prepared by methods similar to the previous example with the corresponding reagents as indicated in the table.

| Example No. | Name | Structure | Procedure Reference | Reagents |
|---|---|---|---|---|
| 52 | 4-Cyano-1H-imidazole-2-carboxylic acid [4-(2-nitroimino-hexahydro-pyrimidin-5-yl)-2-(4,4-dimethyl-cyclohex-1-enyl)-phenyl]-amide | 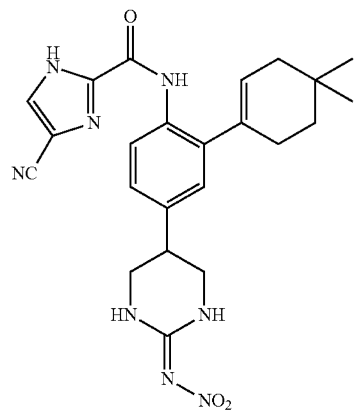 [SMILES: CC1(C)CC=C(c2cc(C3CNC(=N[N+](=O)[O-])NC3)ccc2NC(=O)c2nc(C#N)c[nH]2)CC1] | Example 51 | B(OH)$_2$ (Combi-Blocks, Inc.); H$_2$N-C(=N-NO$_2$)-NH$_2$ (Aldrich Chemical Co., Inc.); imidazole-CO$_2$K with NC (Example 1, step (d)) |
| 53 | {5-[4-[(4-Cyano-1H-imidazole-2-carbonyl)-amino]-3-(4,4-dimethyl-cyclohex-1-enyl)-phenyl]-tetrahydro-pyrimidin-2-ylidene}-carbamic acid methyl ester | 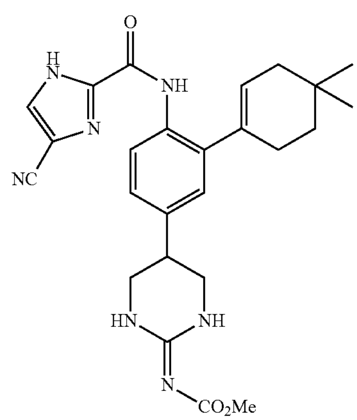 [SMILES: COC(=O)N=C1NCC(c2ccc(NC(=O)c3nc(C#N)c[nH]3)c(C3=CCC(C)(C)CC3)c2)CN1] | Example 51 | B(OH)$_2$ (Combi-Blocks, Inc.); H$_2$N-C(=N-CO$_2$Me)-NH$_2$ (Helv. Chim. Acta, 35, 1005-20 (1952)); imidazole-CO$_2$K with NC (Example 1, step (d)) |

Example 54

4-Cyano-1H-imidazole-2-carboxylic acid [4-(2-cyanoimino-1,3-dimethyl-hexahydro-pyrimidin-5-yl)-2-(4,4-dimethyl-cyclohex-1-enyl)-phenyl]-amide trifluoroacetic acid salt

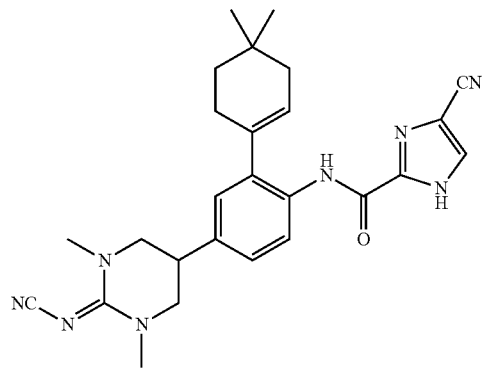

a.) 5-(4-Bromo-phenyl)-tetrahydro-pyrimidin-2-ylidene-cyanamide

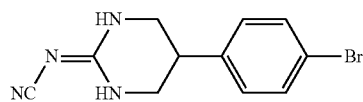

To a stirred suspension of 2-(4-bromo-phenyl)-propane-1,3-diol (462 mg, 2.00 mmol, JACS, 125(46), 13948) in DCM (50 mL) and Et$_3$N (0.7 mL, 5 mmol) was added MsCl (0.3 mL, 4.0 mmol) at 0° C. The resulting mixture was allowed to warm to RT and stirred for 4 h and treated with satd NaHCO$_3$ (50 mL). The DCM layer was separated and the aq layer was extracted twice with DCM (2×20 mL). The organic layers were combined, dried (Na$_2$SO$_4$) and concentrated in vacuo. The resulting bismesylate was dried under high vacuum for 2 h and redissolved in DMF (5 mL) To this mixture NaN$_3$ (0.52 g, 8.0 mmol) was added. The resulting mixture was heated at 70° C. over night. The reaction mixture was allowed to cool to RT and treated with water (10 mL). The product was then extracted with EtOAc (3×10 mL). The organic layers were combined, dried (Na$_2$SO$_4$) and concentrated in vacuo. The resulting diazide was dried under high vacuum for 2 h and used in next step without further purification. The diazide (280 mg, 1 mmol) was dissolved in MeOH (5 mL) and Et$_3$N (1.4 mL, 10 mmol) and the resulting solution was placed under N$_2$. To this solution propanedithiol (1.0 mL, 10 mmol) was added. The resulting mixture was stirred at RT overnight and concentrated to obtain a viscous oil which was dried under high vacuum for 2 h, dissolved in ether (20 mL) and treated with 2M HCl in ether (10 mL, 20 mmol). The resulting suspension was sonicated for 5 min and stirred for 5 h. The precipitate formed was collected by suction filtration and dried in vacuo to obtain 2-(4-bromo-phenyl)-propane-1,3-diamine dihydrochloride which was directly used in next step without further purification. The dihydrochloride salt (302 mg, 1 mmol) was added to a solution of Et$_3$N (0.7 mL, 5 mmol) and dimethyl N-cyanodithioiminocarbonate (146 mg, 1.00 mmol) in EtOH (10 mL). The resulting mixture was heated at 80° C. overnight. The reaction mixture was allowed to cool to RT and stirred for another 2 h. The precipitate formed was collected by suction filtration to obtain 92 mg (33%) of the title compound. Mass spectrum (ESI, m/z): Calcd. for $C_{11}H_{11}BrN_4$, 279.0 (M+H). found 279.1.

b) 5-(4-Bromo-phenyl)-1,3-dimethyl-tetrahydro-pyrimidin-2-ylidene-cyanamide

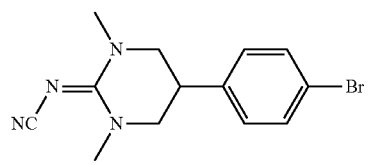 [SMILES: CN1CC(c2ccc(Br)cc2)CN(C)C1=NC#N]

To a suspension of NaH (80 mg, 2 mmol) in dry DMF (10 mL), 5-(4-bromo-phenyl)-tetrahydro-pyrimidin-2-ylidene-cyanamide (279 mg, 1.00 mmol, as prepared in the previous step) in DMF (5 mL) was added dropwise at 0° C. The resulting mixture was stirred at RT for 30 min and cooled back to 0° C. and treated with MeI (0.24 mL, 4.0 mmol). The mixture was allowed to warm to RT, stirred for 2 h and diluted with water (10 mL) and extracted with DCM (3×20 mL). The DCM layers were combined, dried (Na$_2$SO$_4$) and concentrated. The solid obtained was suspended in hexane and sonicated for 5 min and the precipitate was collected by suction filtration 173 mg, 62%. Mass spectrum (ESI, m/z): Calcd. for $C_{13}H_{15}BrN_4$, 307.0 (M+H). found 307.4.

c) 5-(4-Amino-phenyl)-1,3-dimethyl-tetrahydro-pyrimidin-2-ylidene-cyanamide

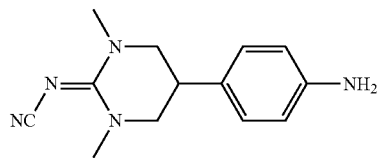 [SMILES: CN1CC(c2ccc(N)cc2)CN(C)C1=NC#N]

To a screw-capped vial containing tri-tert-butylphosphine (5.0 mg, 0.025 mmol), Pd$_2$(dba)$_3$ (14.3 mg, 0.0250 mmol), Zn[N(SiMe$_3$)$_2$]$_2$ (116 mg, 0.300 mmol) and LiCl (12.6 mg, 0.300 mmol) under Ar was added 5-(4-bromo-phenyl)-1,3-dimethyl-tetrahydro-pyrimidin-2-ylidene-cyanamide (153 mg, 0.500 mmol, as prepared in the previous step) in THF (1 mL). The reaction mixture was then stirred at 60° C. overnight and allowed to cool to RT and treated with 1 N HCl (0.2 mL). The reaction mixture was then transferred to a separatory funnel, diluted with DCM (10 mL) and washed with 1N NaOH (5 mL). The DCM layers were combined, dried (Na$_2$SO$_4$) and concentrated. The solid obtained was purified on silica (50%-100% EtOAc/hexane) to obtain 40 mg, 33% of the title compound. Mass spectrum (ESI, m/z): Calcd. for $C_{13}H_{17}N_5$, 244.10 (M+H), found 244.2.

d) 5-(4-Amino-3-bromo-phenyl)-1,3-dimethyl-tetrahydro-pyrimidin-2-ylidene-cyanamide

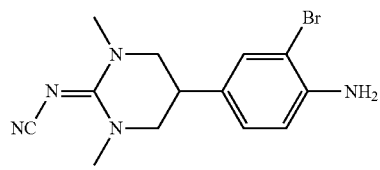 [SMILES: CN1CC(c2ccc(N)c(Br)c2)CN(C)C1=NC#N]

The title compound was prepared according to the bromination procedure of Example 1, step (j), using 5-(4-aminophenyl)-1,3-dimethyl-tetrahydro-pyrimidin-2-ylidene-cyanamide as the starting material: Mass spectrum (ESI, m/z): Calcd. for $C_{13}H_{16}BrN_5$, 322.1 (M+H). found 322.2.

e) 5-[4-Amino-3-(4,4-dimethyl-cyclohex-1-enyl)-phenyl]-1,3-dimethyl-tetrahydro-pyrimidin-2-ylidene-cyanamide

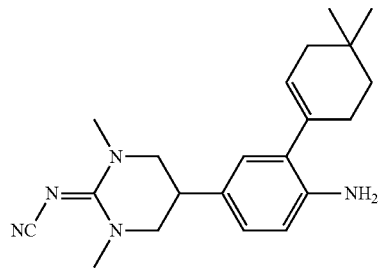 [SMILES: CN1CC(c2ccc(N)c(C3=CCC(C)(C)CC3)c2)CN(C)C1=NC#N]

The title compound was prepared according to the Suzuki coupling procedure of Example 3, step (a), using 4,4-dimethyl-cyclohex-1-enyl boronic acid and 5-(4-amino-3-bromo-phenyl)-1,3-dimethyl-tetrahydro-pyrimidin-2-ylidene-cyanamide Mass spectrum (ESI, m/z): Calcd. for $C_{21}H_{29}N_5$, 352.2 (M+H). found 352.4 f) 4-Cyano-1-(2-trimethylsilanyl-ethoxymethyl)-1H-imidazole-2-carboxylic acid [4-(2-cyanoimino-1,3-dimethyl-hexahydro-pyrimidin-5-yl)-2-(4,4-dimethyl-cyclohex-1-enyl)-phenyl]-amide

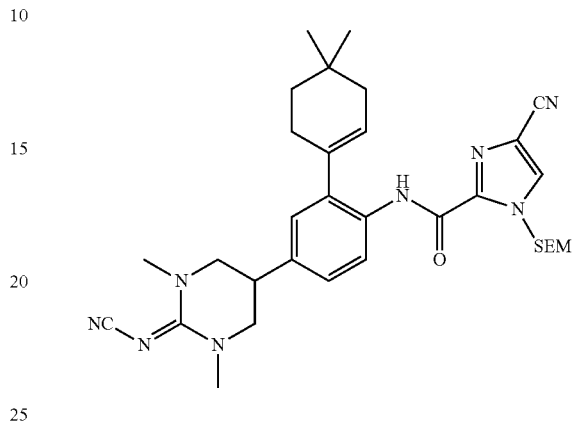

5-[4-Amino-3-(4,4-dimethyl-cyclohex-1-enyl)-phenyl]-1,3-dimethyl-tetrahydro-pyrimidin-2-ylidene-cyanamide (as prepared in the previous step) was coupled to 4-cyano-1-(2-trimethylsilanyl-ethoxymethyl)-1H-imidazole-2-carboxylic acid, potassium salt (as prepared in Example 1) as described in Example 1, step (l) to obtain the title compound: Mass spectrum (ESI, m/z): Calcd. for $C_{32}H_{44}N_8O_2Si$, 601.3 (M+H). found 601.3.

g) 4-Cyano-1H-imidazole-2-carboxylic acid [4-(2-cyanoimino-1,3-dimethyl-hexahydro-pyrimidin-5-yl)-2-(4,4-dimethyl-cyclohex-1-enyl)-phenyl]-amide trifluoroacetic acid salt The title compound was synthesized from 4-cyano-1-(2-trimethylsilanyl-ethoxymethyl)-1H-imidazole-2-carboxylic acid [4-(2-cyanoimino-1,3-dimethyl-hexahydro-pyrimidin-5-yl)-2-(4,4-dimethyl-cyclohex-1-enyl)-phenyl]-amide (as prepared in the previous step) as described in Example 7, step (e): $^1$H-NMR (CD$_3$OD; 400 MHz): δ 8.22 (d, 1H, J=8.4 Hz), 8.01 (s, 1H), 7.25 (dd, 1H, J=8.4, 2.1 Hz), 7.08 (d, 1H, J=2.1 Hz), 5.82 (br s, 1H), 3.4-3.6 (m, 4H), 3.25 (s, 6H), 3.1-3.2 (m, 1H), 2.38 (m, 2H), 2.15 (m, 2H), 1.62 (m, 2H), 1.15 (s, 6H); Mass spectrum (ESI, m/z): Calcd. for $C_{26}H_{30}N_8O$, 471.2 (M+H), found 471.3.

IV. Results

Fluorescence Polarization Competition Immunoassay

A fluorescence polarization competition immunoassay was used to measure compound inhibition of CSF-1R phosphorylation of tyrosine on a synthetic CSF-1R$_{555-568}$ peptide (SYEGNSYTFIDPTQ) (SEQ ID NO: 1). The assay was performed in black 96-well microplates (Cat # 42-000-0117, Molecular Devices, Sunnyvale, CA). To each well, 5 μL of compound (in 4% DMSO) were mixed with 2 μL of 3.5 nM CSF-1R, 25 mM MgCl$_2$ in assay buffer (100 mM HEPES, pH 7.5, 1 mM DTT, 0.01% Tween-20), and 2 μL of 1540 μM peptide in assay buffer. The kinase reaction was initiated by adding 1 μL of 10 mM ATP in assay buffer. The final concentrations in the 10 uL reaction mixture were 100 mM HEPES, pH 7.5, 1 mM DTT, 0.01% Tween-20, 2% DMSO, 308 μM SYEGNSYTFIDPTQ (SEQ ID NO: 1), 1 mM ATP, 5 mM MgCl$_2$, and 0.7 nM CSF-1R. Positive and negative control wells were included on each plate, where 4% DMSO in assay buffer was substituted for the compound; in addition, positive control wells received 1.2 µL of 50 mM EDTA before the start of the reaction.

The plates were covered and incubated at room temperature for 80 min. Reactions were stopped by addition of 1.2 µL of 50 mM EDTA. Each well then received 10 µL of a 1:1:3 mixture of 10× anti-phosphotyrosine antibody, 10×PTK green tracer, and FP dilution buffer, respectively (Cat. # P2837, Invitrogen, Carlsbad, Calif.). The plates were covered, incubated for 30 min at room temperature, and the fluorescence polarization was read on an Analyst plate reader (Molecular Devices). Instrument settings were: 485 nm excitation, 530 nm emission, with a 505 nm cut-off filter; Z height: middle of well; G factor: 0.93. Under these conditions, the fluorescence polarization values for positive and negative controls were approximately 290 and 160, respectively, and were used to define 100% and 0% inhibition of the CSF-1R reaction. Reported $IC_{50}$ values are the mean of three of at least three determinations.

CSF-1-Driven Mouse Bone-Marrow Derived Macrophages Assay

Macrophages are derived by culturing mouse bone marrow in alpha-MEM supplemented with 10% FCS (fetal calf serum) and 50 ng/ml recombinant mouse CSF-1 in bacteriologic dishes. On the sixth day, macrophages are detached from dishes, washed, and resuspended to 0.1 million cells/ml in alpha-MEM containing 10% FCS. One hundred ul of cell suspension are distributed per well into 96 well culture plates. Wells are further supplemented with the addition of 50 ul media containing 15 ng/ml CSF-1, 3 uM Indomethacin, and 3× of a dilution series of test compounds. The cells are cultured for 30 hrs at 37° C. and 5% $CO_2$. During the final six hours, cultures are supplemented with an additional 30 ul of media containing a 1:500 dilution of bromodeoxyuridine (BrDU). At the end of the culture period, the media is removed and replaced with 200 of fixative solution for 30' @ room temperature. The fixative is then dispelled from the plates and the plates allowed to air dry. Incorporation of BrDU into the fixed, dried cells is quantified using a specific ELISA (Cat X1327K) from Exalpha Corporation (Watertown Mass.). Background values are determined from wells without BrDU reagent. IC50 values are calculated based on signal from CSF-1 stimulated cells without compound present.

Table 1 lists the assay results for representative compounds of the invention.

TABLE 1

| Example Number | IC50 (µM) | mCSF driven proliferation BMDM (Mouse) (µM) |
|---|---|---|
| 1 | 0.001 | 0.01 |
| 3 | 0.001 | 0.007 |
| 4 | 0.003 | 0.07 |
| 5 | 0.003 | 0.06 |
| 6 | 0.01 | 0.06 |
| 7 | 0.001 | 0.01 |
| 8 | 0.0004 | 0.003 |
| 9 | 0.001 | 0.005 |
| 10 | N/A | 0.1 |
| 11 | 0.002 | 0.002 |
| 12 | 0.003 | 0.04 |
| 13 | 0.002 | 0.1 |
| 14 | 0.001 | 0.004 |
| 15 | >0.3 | N/A |
| 54 | 0.00042 | 0.039 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The claimed invention is:

1. A compound of Formula I:

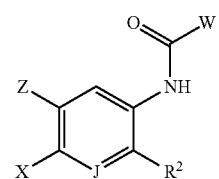

wherein:

W is

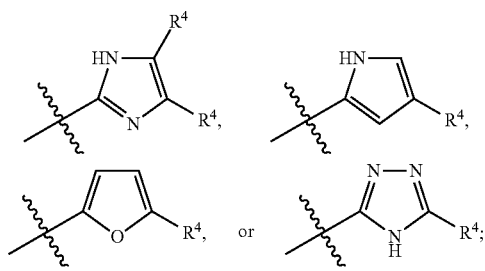

wherein R⁴=H, F, Cl, Br, I, OH, OCH₃, OCH₂CH₃, —C₍₁₋₃₎alkyl, —CO₂R⁵, CONR⁶R⁷, C≡CR⁸, or CN;
wherein R⁵=H, or —C₍₁₋₃₎alkyl;
R⁶=H, or —C₍₁₋₃₎alkyl;
R⁷=H, or —C₍₁₋₃₎alkyl; and
R⁸=H, —CH₂OH, or —CH₂CH₂OH;

R² is cycloalkyl, spiro-substituted cycloalkenyl, heterocyclyl, spiro-substituted piperidinyl, thiophenyl, dihydrosulfonopyranyl, phenyl, furanyl, tetrahydropyridyl, or dihydropyranyl, any of which is optionally independently substituted with one or two of each of the following: chloro, fluoro, hydroxy C₍₁₋₃₎alkyl, or C₍₁₋₄₎alkyl;

X is

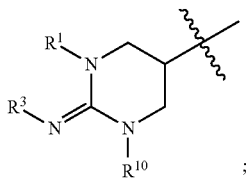

wherein R¹ and R¹⁰ are independently H, —CH₃, or —C₂—C₅alkyl, optionally substituted with one or two of: Me, Et, OH, NH₂, NHMe, NMe₂, NHEt, NEt₂, pyrrolidinyl, pyridyl, morpholino, CONH₂, or COOH and such that when any two heteroatoms are attached to said C₂ to C₅ alkyl group there exists at least two carbon atoms between them, R³ is —SO₂Me, SO₂Et, —CO₂R⁹, —NO₂, or —CN;
wherein R⁹ is H, or C₍₁₋₃₎alkyl;

Z is H, F, Cl, Br, C₁—C₃ alkyl or —CH₂OH; and

J is CH or N; or a solvate, hydrate, tautomer or pharmaceutically acceptable salt thereof.

2. The compound of claim 1, wherein:

R² is selected from the group consisting of:
cyclohexenyl, 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, 4-tert-butyl cyclohexenyl, cycloheptenyl, spiro[2.5]oct-5-enyl, spiro[3.5]non-6-enyl, spiro[4.5]dec-7-enyl, spiro[5.5]undec-2-enyl, 3-aza-spiro[5.5]undecanyl, 8-aza-spiro[4.5]decanyl, 4-methyl piperidinyl, 4-ethyl piperidinyl, 4-(1'hydroxyeth-2'yl)piperidinyl, and 4,4 dimethyl piperidinyl thiophenyl, dihydrosulfonopyranyl, phenyl, furanyl, tetrahydropyridyl, and dihydropyranyl.

3. The compound of claim 1, wherein:

W is

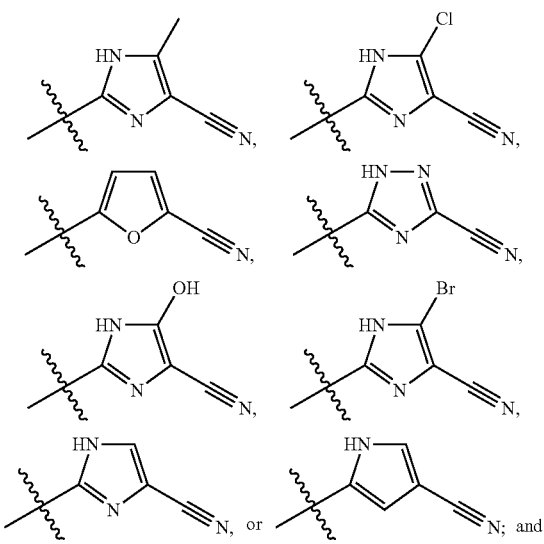

R² is

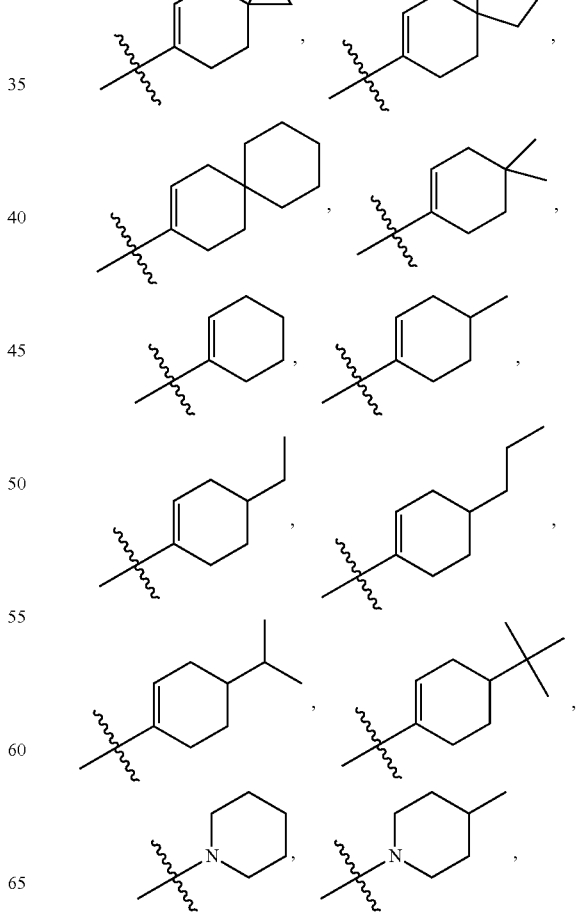

-continued
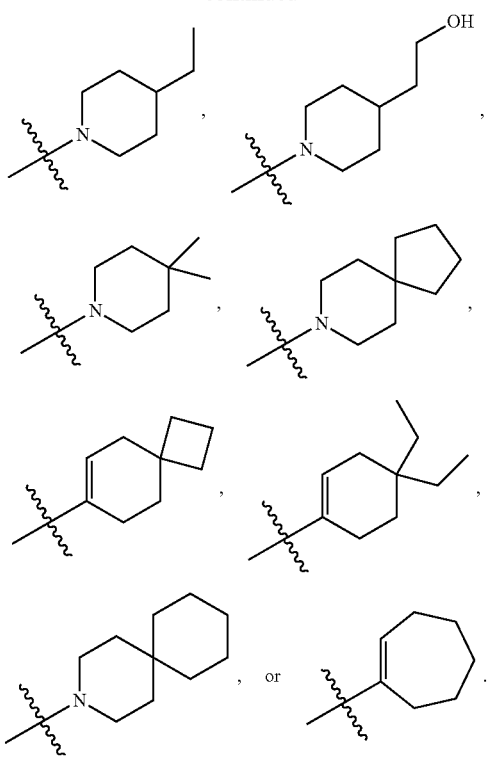
4. The compound of claim 3, wherein:
R² is
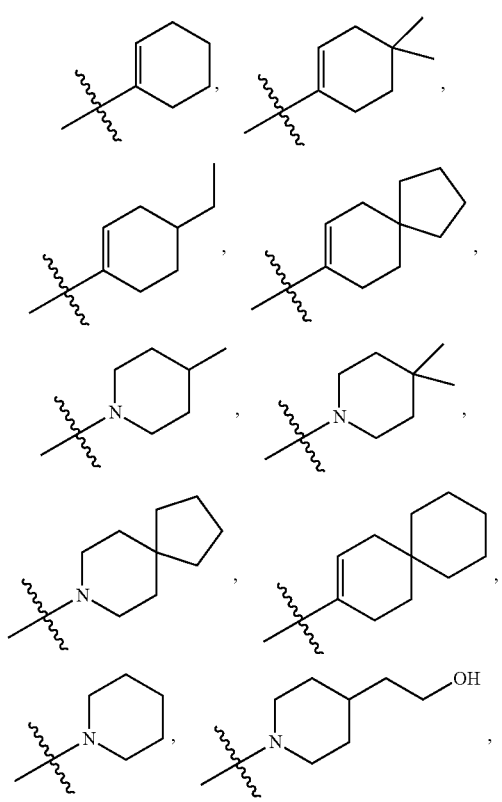
-continued
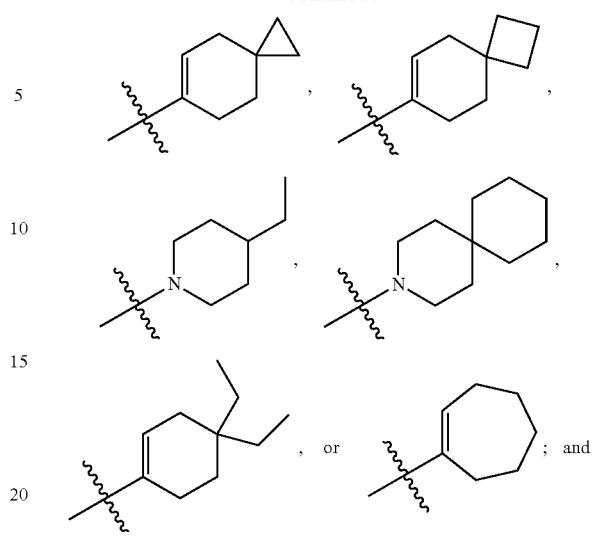
Z is H, C₁—C₃ alkyl or —CH₂OH.
5. The compound of claim 4, wherein:
R² is
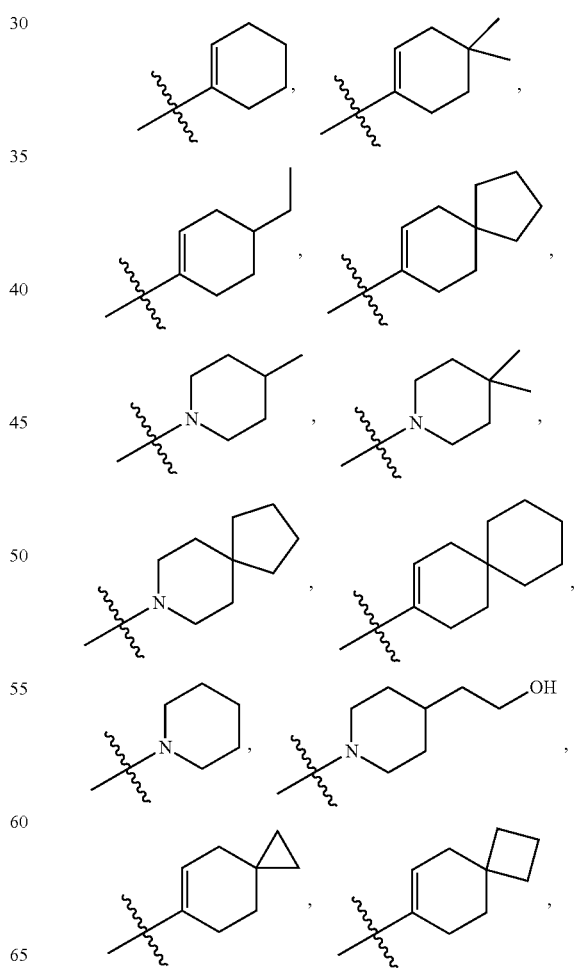

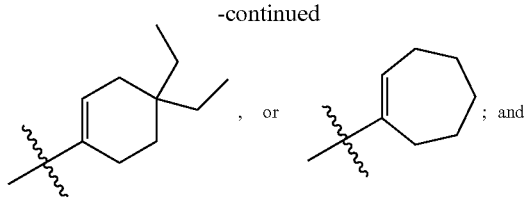
Z is H or —CH$_2$OH.
6. The compound of claim 5, wherein:
W is
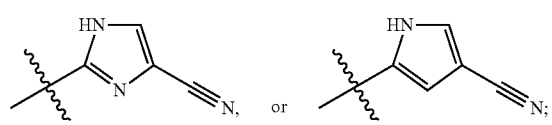 [SMILES: *c1nc(C#N)c[nH]1 ; "or" ; *c1cc(C#N)c[nH]1]
R$^2$ is
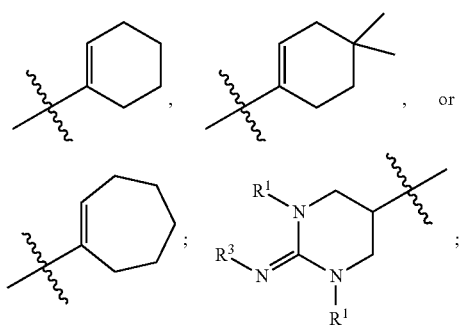
X is
wherein R$^1$ is H, or —CH$_3$; and
R$^3$ is —SO$_2$CH$_3$, or —CN.
7. A compound selected from the group consisting of:
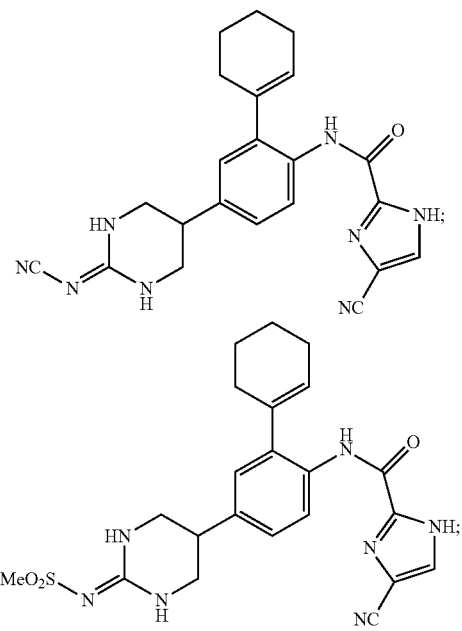
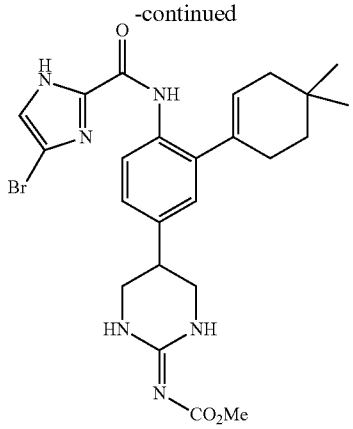
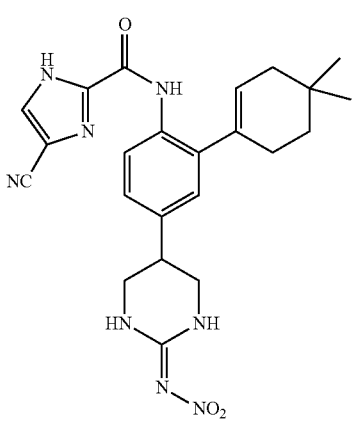
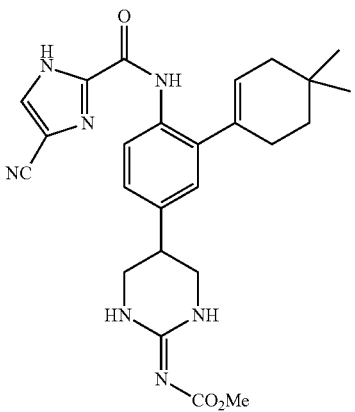
or a solvate, hydrate, tautomer or pharmaceutically acceptable salt thereof.

8. The compound of claim 7 selected from the group consisting of:

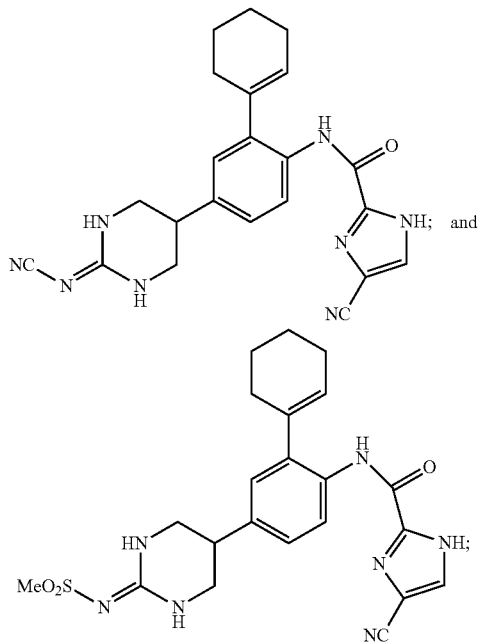

or a solvate, hydrate, tautomer or pharmaceutically acceptable salt thereof.

9. A compound which is

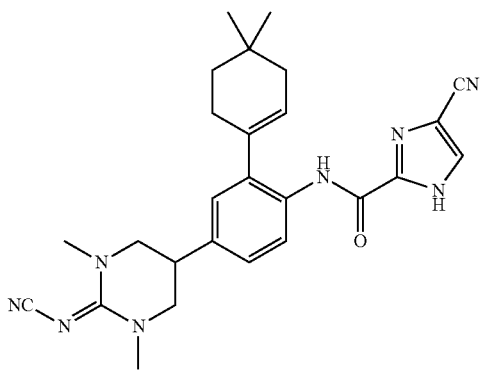 [SMILES: CN1CC(c2ccc(NC(=O)c3nc(C#N)c[nH]3)c(C3=CCC(C)(C)CC3)c2)CN(C)C1=NC#N]

or a solvate, hydrate, tautomer, or pharmaceutically acceptable salt thereof.

10. A pharmaceutical composition, comprising a compound of claim 1 and a pharmaceutically acceptable carrier.

11. A pharmaceutical dosage form comprising a pharmaceutically acceptable carrier and from about 0.5 mg to about 10 g of at least one compound of claim 1.

12. A dosage form according to claim 10 adapted for parenteral or oral administration.

13. A method of inhibiting inflammation in a mammal in need thereof, comprising administering to the mammal a therapeutically effective amount of at least one compound of claim 1.

14. A method of treating a disease with an inflammatory component in a mammal, wherein the disease is selected from the group consisting of glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia and Alzheimer's dementia, comprising administering to a mammal a therapeutically effective amount of at least one compound of claim 1.

15. A method of treating pain selected from the group consisting of skeletal pain caused by tumor metastasis or osteoarthritis, visceral, inflammatory, and neurogenic pain, in a mammal, comprising administering to a mammal in need of such treatment a therapeutically effective amount of at least one compound of claim 1.

16. A method of treating osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone, comprising administering to a mammal in need of such treatment a therapeutically effective amount of at least one compound of claim 1.

17. A method of treating metastasis from ovarian cancer, uterine cancer, breast cancer, prostate cancer, lung cancer, colon cancer, stomach cancer, and hairy cell leukemia in a mammal, comprising administering to a mammal in need of such treatment a therapeutically effective amount of at least one compound of claim 1.

18. A method of treating an autoimmune disease selected from the group consisiting of: systemic lupus erythematosus, rheumatoid arthritis, and other forms of inflammatory arthritis, psoriasis, Sjogren's syndrome, multiple sclerosis, and uveitis in a mammal, comprising administering to a mammal in need of such treatment a therapeutically effective amount of at least one compound of claim 1.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Glu Gly Asn Ser Tyr Thr Phe Ile Asp Pro Thr Gln
1               5                   10
```